(12) United States Patent
Nittoli et al.

(10) Patent No.: US 9,951,141 B2
(45) Date of Patent: Apr. 24, 2018

(54) ANTIBODY-DRUG CONJUGATES, THEIR PREPARATION AND THEIR THERAPEUTIC USE

(71) Applicant: REGENERON PHARMACEUTICALS, INC., Tarrytown, NY (US)

(72) Inventors: Thomas Nittoli, Pearl River, NY (US); Arthur Kunz, New City, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 15/314,909

(22) PCT Filed: Jun. 1, 2015

(86) PCT No.: PCT/US2015/033618
§ 371 (c)(1),
(2) Date: Nov. 29, 2016

(87) PCT Pub. No.: WO2015/187596
PCT Pub. Date: Dec. 10, 2015

(65) Prior Publication Data
US 2017/0121413 A1   May 4, 2017

Related U.S. Application Data

(60) Provisional application No. 62/006,816, filed on Jun. 2, 2014, provisional application No. 62/139,052, filed on Mar. 27, 2015.

(51) Int. Cl.
*A61K 39/395* (2006.01)
*C07K 16/28* (2006.01)
*C07K 16/30* (2006.01)
*A61K 47/48* (2006.01)

(52) U.S. Cl.
CPC .... *C07K 16/2866* (2013.01); *A61K 47/48384* (2013.01); *A61K 47/48438* (2013.01); *A61K 47/48561* (2013.01); *A61K 47/48569* (2013.01); *A61K 47/48715* (2013.01); *C07K 16/30* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,595,292 | B2 | 9/2009 | Brocchini et al. |
| 7,939,630 | B2 | 5/2011 | Brocchini et al. |
| 8,816,051 | B2 | 8/2014 | Brocchini et al. |
| 9,005,598 | B2 | 4/2015 | Godwin et al. |
| 2008/0171040 | A1 | 7/2008 | Ebens et al. |
| 2008/0305044 | A1 | 12/2008 | McDonagh et al. |
| 2014/0069960 | A1 | 3/2014 | Sannier et al. |
| 2014/0363454 | A1 | 12/2014 | Jackson et al. |
| 2015/0056222 | A1 | 2/2015 | Papadopoulos et al. |
| 2015/0125473 | A1 | 5/2015 | Burt et al. |
| 2015/0216994 | A1 | 8/2015 | Godwin et al. |
| 2015/0283259 | A1 | 10/2015 | Burt et al. |

FOREIGN PATENT DOCUMENTS

| | | |
|---|---|---|
| EP | 0 425 235 A2 | 5/1991 |
| WO | WO 2005/010151 A2 | 2/2005 |
| WO | WO 2013/085925 A1 | 6/2013 |
| WO | WO 2013/190272 A1 | 12/2013 |
| WO | WO 2013/190292 A2 | 12/2013 |
| WO | WO 2014/064424 A1 | 5/2014 |
| WO | WO 2014/145090 A1 | 9/2014 |
| WO | WO 2014/197849 A2 | 12/2014 |
| WO | WO 2014/197854 A1 | 12/2014 |
| WO | WO 2014/197866 A1 | 12/2014 |

OTHER PUBLICATIONS

George Badescu: Director Scientific Affairs—Bioconjugation & Protein Engineering, "Producing Better ADCs Using ThioBridge™ Conjugation", ABZENA—Enabling better biopharmaceuticals, World ADC Summit of Oct. 27, 2014, San Diego, 29 pages.
International Search Report and Written Opinion in PCT/US2015/033618, dated Dec. 21, 2015, 20 pages.
Badescu et al., "Bridging Disulfides for Stable and Defined Antibody Drug Conjugates", *Bioconjugate Chemistry*, May 3, 2014, vol. 25, No. 6, pp. 1124-1136, XP055165403.
Del Rosario et al., "Sulfhydryl Site-Specific Cross-Linking and Labeling of Monoclonal Antibodies by a Fluorescent Equilibrium Transfer Alkylation Cross-Link Reagent", *Bioconjugate Chemistry*, 1990, vol. 1, No. 1, pp. 51-59, XP002313938.
Sapra et al., "Monoclonal antibody-based therapies in cancer: Advances and Challenges" *Pharmacology & Therapeutics*, 2013, vol. 138, pp. 452-469.
Widdison et al., "Semisynthetic Maytansine Analogues for the Targeted Treatment of Cancer", *J. Med. Chem*, 2006, vol. 49, pp. 4392-4408, XP-002679529.

*Primary Examiner* — Sheela J. Huff
(74) *Attorney, Agent, or Firm* — Squire Patton Boggs (US) LLP

(57) ABSTRACT

The present disclosure relates to conjugates comprising biologically active molecules linked to a multimeric antigen-binding compound or a multimeric immunoglobulin via a linker. The disclosure further provides reagents and methods of manufacturing the conjugates and the linkers. The disclosure also provides compositions comprising the conjugates, methods of modifying abnormal cell growth and methods of treatment using the conjugates or the compositions.

54 Claims, 11 Drawing Sheets

| Lane | Sample Name |
|---|---|
| 1 | Mol. Wt. Markers (Kdaltons) |
| 2 | IgG1 Antibody |
| 3 | IgG1 Antibody-BrMethacrylate(1)+dhAA |
| 4 | blank |
| 5 | blank |
| 6 | IgG1 Antibody (reduced) |
| 7 | IgG1 Antibody-BrMethacrylate(1)+dhAA (reduced) |
| 8 | blank |
| 9 | blank |
| 10 | blank |
| 11 | blank |
| 12 | blank |

| Lane | Sample Name |
|---|---|
| 1 | Mol. Wt. Markers (Kdaltons) |
| 2 | Intact IgG1 Antibody |
| 3 | Compound 6 |
| 4 | Compound 9 |
| 5 | Compound 2 |
| 6 | Compound 1 |
| 7 | blank |
| 8 | Reduced IgG1 Antibody |
| 9 | Compound 6 |
| 10 | Compound 9 |
| 11 | Compound 2 |
| 12 | Compound 1 |

| Lane | Sample Name |
|---|---|
| 1 | Mol. Wt. Markers (Kdaltons) |
| 2 | Unmodified Antibody |
| 3 | Compound 28 |
| 4 | Compound 29 |
| 5 | Compound 26 |
| 6 | blank |
| 7 | blank |
| 8 | Unmodified Antibody |
| 9 | Compound 28 |
| 10 | Compound 29 |
| 11 | Compound 26 |
| 12 | blank |

US 9,951,141 B2

ANTIBODY-DRUG CONJUGATES, THEIR PREPARATION AND THEIR THERAPEUTIC USE

This application is a continuation of International Patent Application No. PCT/US2015/033618, filed Jun. 1, 2015, which claims priority to U.S. Provisional Patent Application No. 62/139,052, filed Mar. 27, 2015, and also claims priority to U.S. Provisional Patent Application No. 62/006,816, filed Jun. 2, 2014, the disclosures of which are herein incorporated by reference in their entirety for all purposes.

TECHNICAL FIELD

The disclosure relates to conjugates comprising biologically active molecules connected to a multimeric antigen-binding compound through a linker compound. The disclosure also provides reagents and methods for conjugating the biologically active molecules to the multimeric antigen-binding compound.

BACKGROUND

Antibody drug conjugate (ADC) are antibodies that are conjugated, via chemical linkers, to cytotoxic agents. ADCs leverage an antibody's binding specificity for its target to deliver cytotoxic agents to an abnormal cell. Traditional ADC technology involves chemically attaching a drug, through a linker, to particular amino acid residues of the antibody. For example, the linker can be attached to the antibody at the sulfhydryl groups of one or more cysteine residues within the antibody heavy and/or light chains. A recognized problem with conjugation at cysteine residues, however, is that the process requires disrupting one or more interchain disulfide bonds which ordinarily serve to maintain the structure and function of the antibody molecule. Cysteine-conjugated ADCs can have reduced stability, which potentially impedes the binding and therapeutic properties of the ADC. Thus, there is a need for techniques for conjugating an antibody at its cysteine residues that do not significantly impact the antibody's binding affinity, e.g., methods of conjugation that reconnect cysteine residues of an interchain disulfide bond cleaved during the conjugation process.

SUMMARY

Provided herein are chemical linkers that connect a biologically active compound, e.g., cytotoxic agent, to cysteine residues of a multimeric antigen-binding compound, e.g., antibody, as well as conjugates thereof, pharmaceutical compositions comprising the same, methods of preparing the same, and methods of treating disorders comprising administering the same.

DETAILED DESCRIPTION

Figure 1:
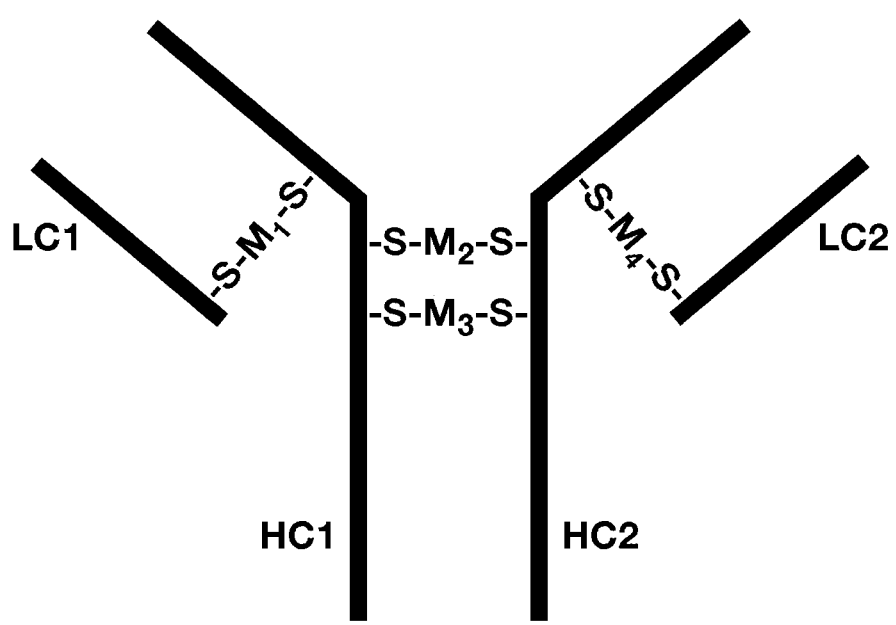
FIG. 1 shows a multimeric immunoglobulin conjugate.

The references to certain embodiments made in the following description are considered illustrative only of the principles of the disclosure. Further, since numerous modifications and changes will readily be apparent to those skilled in the art, it is not intended to limit the disclosure to the exact construction and process shown as described herein. Accordingly, all suitable modifications and equivalents may be resorted to as falling within the scope of the disclosure and as defined by the claims that follow.

I. DEFINITIONS

The words "comprise", "comprising", "include" and "including" when used in this specification and in the following claims are intended to specify the presence of the stated features, integers, components, or steps, but they do not preclude the presence or addition of one or more additional features, integers, components, or steps thereof.

General terms used in any of the embodiments herein can be defined as follows; however, the meaning stated should not be interpreted as limiting the scope of the term per se.

The symbol ⟿ denotes the points of attachment.

The term "conjugate" as used herein refers to compound having a multimeric antigen-binding compound or a multimeric immunoglobulin, a linker and a biologically active molecule. Illustrative examples include compounds of formula (I), and FIG. 1.

The term "spacer" as used herein refers to chemical building blocks of the linker used to spatially separate the multimeric antigen-binding compound or a multimeric immunoglobulin from the biologically active molecule and to allow for catabolism of the linker inside of cells. A spacer can be represented by $Z_1$ and $Z_2$.

The term "alkyl" as used herein refers to a hydrocarbon group having a general formula $C_nH_{2n+1}$. Examples of alkyl include, but are not limited to, methyl, ethyl, 1-propyl, 2-propyl, 1-butyl, and the like. Further exemplary alkyl groups include, but are not limited to, those that have from one to ten carbon atoms, one to nine carbon atoms, one to eight carbon atoms, one to seven carbon atoms, one to six carbon atoms, one to five carbon atoms, one to four carbon atoms, one to three carbon atoms, one to two carbon atoms or one carbon atom.

The term "aryl" as used herein refers to a monovalent or polycyclic aromatic hydrocarbon. Exemplary aryl groups include, but are not limited to, those having 6 to 18 carbon atoms. Exemplary aryl groups further include, but are not limited to, phenyl, substituted phenyl, naphthalenyl, anthracenyl, indenyl, tetrahydronapthyl and the like.

The term "alkenyl" as used herein refers to an aliphatic linear or branched monovalent hydrocarbon radical of two or more carbon atoms with at least one site of unsaturation. Examples of alkenyl groups include, but are not limited to, ethylenyl, vinyl, allyl, and the like.

The term "alkynyl" as used herein refers to a univalent aliphatic hydrocarbon radical containing at least one triple bond. Exemplary alkynyl groups include, but are not limited to, those having from two to twenty carbon atoms (and include at least one triple bond). Exemplary alkynyl groups also include, but are not limited to, ethynyl, propynyl, 1-butynyl, 2-butynyl, 1-pentynyl, hexynyl and the like.

The term "cycloalkyl" as used herein, refers to a monovalent saturated carbocyclic ring radical. Exemplary cycloalkyl groups include those having 3 to 7 ring carbon atoms. Exemplary cycloalkyl groups include, but are not limited to, cyclopropyl, cyclopentyl, and cyclohexyl.

The term "heteroaryl" as used herein, refers to a monovalent aromatic radical containing at least one heteroatom in its aromatic ring. Heteroaryl groups include, but are not limited to fused ring systems (at least one must be aromatic) that include up to 5 to 18 atoms, containing one or more heteroatoms independently selected from nitrogen, sulfur or oxygen. Illustrative heteroaryl groups further include, but are not limited to, pyridinyl, triazolyl, furyl, pyrazinyl, thienyl, isoxazolyl, indazolyl, furazanyl, benzothiazolyl, quinazolinyl, and furopyridinyl.

The term "heterocyclyl" as used herein refers to saturated or partially saturated carbocyclic radical, including, but not limited to those having 3 to 18 carbon atoms, in which at least one ring atom is a heteroatom selected from nitrogen, oxygen, phosphorous, and sulfur. A heterocycyl can be a monocycle or a bicycle, for example. Exemplary heterocyclyl groups include, but are not limited to, pyrolidinyl, tetrahydrofuranyl, dihydropyranyl, thioxanyl, 2H-pyranyl, dioxanyl, dithianyl, piperidino, and the like.

The phrase "pharmaceutically acceptable salt" as used herein refers to both organic and inorganic salts of the conjugate compounds described herein, e.g., compounds of formula (I), FIG. 1), formula (III). The salts are pharmaceutically acceptable and include: sulfate, citrate, nitrate, phosphate, ascorbate, chloride, bromide, gluconate, benzoate, oxalate, pantothenate, and the like. Note that pharmaceutically acceptable salts herein may include more than one charged atom in its structure as well as one or more counter ion. Preparation of conjugate compounds herein as pharmaceutically acceptable salts is well known to one of skill in the art.

The term "therapeutically effective amount" as used herein refers to an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

II. MULTIMERIC ANTIGEN-BINDING COMPOUND CONJUGATES

The present disclosure provides multimeric antigen-binding compound conjugates comprising the formula (I):

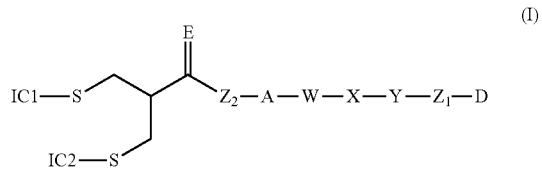

wherein:
IC1 is a first immunoglobulin chain, and
IC2 is a second immunoglobulin chain;
    further wherein IC1 and/or IC2, alone or together comprise at least one antigen-binding domain;
$Z_1$ and $Z_2$ are each independently absent or a spacer;
E is O, S, $NR_4$, or $CR_5R_6$;
D is a biologically active molecule;
A is absent, a natural or non-natural amino acid, or a peptide comprising 2-20 amino acids;
W is absent, —O—, —S—, —$CR_5R_6$—, or —$NR_4$—;
X is absent, aryl, heteroaryl, cycloalkyl, or heterocyclyl,
    wherein aryl, heteroaryl, cycloalkyl, and heterocyclyl are optionally substituted; and Y is absent,

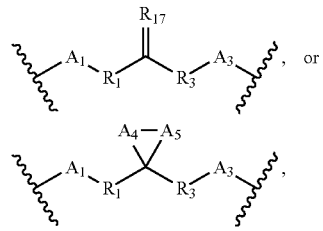

wherein:
$A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —$((CH_2)_{p2}$—O—$)_{p3}$—, —C(=S)—, —C(=S)—S—, —S—C(=S)—, —C(=S)—NH—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, or —O—C(=O)—$NR_4$—,
    wherein alkyl, alkynyl, alkenyl, cycloalkyl, aryl, heteroaryl, and heterocyclyl are optionally substituted;
$A_4$ and $A_5$ are each independently —O—, —S—, —$NR_{18}$—, or —$CR_5R_6$—;
$R_{17}$ is O, S, $NR_{18}$, or $CR_5R_6$;
$R_{18}$ is H, alkyl, alkynyl, alkenyl, cycloalkyl, aryl, heteroaryl, heterocyclyl, or acyl,
    wherein alkyl, alkynyl, alkenyl, cycloalkyl, aryl, heteroaryl, heterocyclyl, and acyl are optionally substituted;
$R_4$, $R_5$, $R_6$ and $R_8$ are each independently H or a substituted or unsubstituted: alkyl, alkenyl, alkynyl, aryl, heteroaryl, or heterocyclyl;
p1, p2 and p3 are each independently 0, or an integer from 1 to 100; and
x is 0, 1 or 2.

In one embodiment, multimeric immunoglobulin or antigen-binding compounds are any molecules capable of binding with some specificity to a given binding partner under physiological conditions. In some aspects the multimeric immunoglobulin or antigen-binding compound is capable of binding to a cell or cell population.

In an embodiment, the disclosure provides the antigen-binding compound-conjugate represented by formula (I), wherein IC1 is a first heavy chain of an antibody or antigen-binding portion thereof; and IC2 is a second heavy chain of the antibody or antigen-binding portion thereof. In certain sub-embodiments wherein IC1 and IC2 are antibody heavy chains, one or more of IC1 and/or IC2 may each be independently associated with or connected to an antibody light chain or antigen-binding portion thereof (e.g., forming a complete tetrameric antibody structure). In a further embodiment, the disclosure provides the antigen-binding compound-conjugate represented by formula (I), wherein the antigen-binding compound-conjugate is substantially stable under reducing conditions. In a further embodiment, the disclosure provides the antigen-binding compound-conjugate represented by formula (I), wherein D is a cytotoxic agent.

In an embodiment, the disclosure provides the antigen-binding compound-conjugate represented by formula (I), wherein IC1 is a heavy chain of an antibody or antigen-binding portion thereof; and IC2 is a light chain of the antibody or antigen-binding portion thereof. In certain sub-embodiments wherein IC1 is an antibody heavy chain and IC2 is an antibody light chain, the IC1/IC2 construct may be associated with or connected to another antibody heavy chain/light chain pair (e.g., forming a complete tetrameric antibody structure). In a further embodiment, the disclosure provides the antigen-binding compound-conjugate represented by formula (I), wherein the antigen-binding compound-conjugate is substantially stable under reducing conditions. In a further embodiment, the disclosure provides the antigen-binding compound-conjugate represented by formula (I), wherein D is a cytotoxic agent. In a further embodiment, the disclosure provides the antigen-binding compound-conjugate represented by formula (I), wherein the antigen-binding compound-conjugate specifically binds a tumor-associated antigen.

In an embodiment, the disclosure provides the antigen-binding compound-conjugate represented by formula (I), wherein the antigen-binding compound-conjugate is substantially stable under reducing conditions and/or in the presence of one or more reducing agents. Reducing agents, for the purpose of the present disclosure, include any agent that can rupture or disrupt a disulfide bond. Examples of suitable reducing agents include dithiothreitol (DTT), 2-mercaptoethanol (BME), 2-mercaptoethylamine (MEA), sodium methanethiolate, sodium 2-sulfanylethanesulfonate, cysteine, tris (2-carboxyethyl) phosphine (TCEP), and derivatives of any of the foregoing. Reducing conditions include incubation in the presence of, or treatment with, one or more reducing agents and/or high temperature. In a further embodiment, the disclosure provides the antigen-binding compound-conjugate represented by formula (I), wherein D is a cytotoxic agent. In a further embodiment, the disclosure provides the antigen-binding compound-conjugate represented by formula (I), wherein the antigen-binding compound-conjugate specifically binds a tumor-associated antigen.

In an embodiment, the disclosure provides the antigen-binding compound-conjugate represented by formula (I), wherein D is a cytotoxic agent (also referred to herein as "biologically active molecules"). As used herein, cytotoxic agents include any agent that is detrimental to the growth, viability or propagation of cells. Examples of cytotoxic agents that can be used in the context of the present disclosure include, e.g., 1-(2chloroethyl)-1,2-dimethanesulfonyl hydrazide, 1,8-dihydroxy-bicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins, camptothecin, carminomycins, carmustine, cemadotins, cisplatin, colchicin, combretastatins, cyclophosphamide, cytarabine, cytochalasin B, dactinomycin, daunorubicin, decarbazine, diacetoxypentyldoxorubicin, dibromomannitol, dihydroxy anthracin dione, disorazoles, dolastatin, doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, spliceostatin, amanatin, or calicheamicin and derivatives of any of the foregoing. According to certain embodiments, the cytotoxic agent is a maytansinoid such as DM1 or DM4, a tomaymycin derivative, or a dolastatin derivative. Other cytotoxic agents known in the art are contemplated within the scope of the present disclosure, including, e.g., protein toxins such as ricin, *C. difficile* toxin, pseudomonas exotoxin, ricin, diphtheria toxin, botulinum toxin, bryodin, saporin, pokeweed toxins (i.e., phytolaccatoxin and phytolaccigenin), and others such as those set forth in Sapra et al., *Pharmacol. & Therapeutics*, 2013, 138:452-469.

In an embodiment, the disclosure provides the antigen-binding compound-conjugate represented by formula (I), wherein the antigen-binding compound-conjugate specifically binds a tumor-associated antigen.

In one embodiment, the disclosure provides antigen-binding compound-conjugate represented by formula (I), wherein $Z_2$ is represented by the following structural formula:

$$-Z_{2A}-Z_{2B}-Z_{2C}-Z_{2D}-,$$

wherein:

$Z_{2A}$, $Z_{2B}$, $Z_{2C}$ and $Z_{2D}$ are each independently absent, an amino acid, a peptide having 2-20 amino acids, an alkyl, an alkynyl, an alkenyl, a cycloalkyl, an aryl, a heteroaryl, a heterocyclyl, $-CR_5R_6-$, $-O-$, $-C(=O)-$, $-O-C(=O)-$, $-C(=O)-O-$, $-O-C(=O)-O-$, $-C(=O)-(CH_x)_{p1}$, $-C(=O)-O-(CH_x)_{p1}$, $-(CH_x)_{p1}-C(=O)-$, $-(CH_x)_{p1}-C(=O)-O-$, $-(O-(CH_2)_{p2}-)_{p3}-$, $-((CH_2)_{p2}-O-)_{p3}-$, $-C(=S)-$, $-C(=S)-S-$, $-C(=S)-NH-$, $-S-C(=S)-$, $-S-C(=S)-S-$, $-S-$, $-SO-$, $-SO_2-$, $-NR_4-$, $-N(R_4)-C(=O)-N(R_8)-$, $-N(R_4)-C(=O)O-$, $-N(R_4)-C(=O)-$, $-C(=O)-N(R_4)-$, $-C(=O)-N(R_4)-C(=O)-$, $-O-C(=O)-N(R_4)$, $-O-C(=S)-N(R_4)-$, or $-C(=S)-N(R_4)-$, wherein alkyl, alkynyl, alkenyl, cycloalkyl, aryl, heteroaryl, and heterocyclyl are optionally substituted and $R_4$, $R_5$, $R_6$ and $R_8$ are each independently H or a substituted or unsubstituted: alkyl, alkenyl, alkynyl, aryl, heteroaryl, or heterocyclyl; and $Z_1$ is represented by the following structural formula:

$$-Z_{1A}-Z_{1B}-Z_{1C}-Z_{1D}-,$$

wherein:

$Z_{1A}$, $Z_{1B}$, $Z_{1C}$ and $Z_{1D}$ are each independently absent, an amino acid, a peptide having 2-20 amino acids, an alkyl, an alkynyl, an alkenyl, a cycloalkyl, an aryl, a heteroaryl, a heterocyclyl, $-CR_5R_6-$, $-O-$, $-C(=O)-$, $-O-C(=O)-$, $-C(=O)-O-$, $-O-C(=O)-O-$, $-C(=O)-(CH_x)_{p1}-$, $-C(=O)-O-(CH_x)_{p1}-$, $-(CH_x)_{p1}-C(=O)-$, $-(CH_x)_{p1}-C(=O)-O-$, $-(O-(CH_2)_{p2}-)_{p3}-$, $-((CH_2)_{p2}-O-)_{p3}-$, $-C(=S)-$, $-C(=S)-S-$, $-C(=S)-NH-$, $-S-C(=S)-$, $-S-C(=S)-S-$, $-S-$, $-SO-$, $-SO_2-$, $-NR_4-$, $-N(R_4)-C(=O)-N(R_8)-$, $-N(R_4)-C(=O)O-$, $-N(R_4)-C(=O)-$, $-C(=O)-N(R_4)-$, $C(=O)-N(R_4)-C(=O)-$, $-O-C(=O)-N(R_4)$, $-O-C(=S)-N(R_4)-$, or $-C(=S)-N(R_4)-$, wherein alkyl, alkynyl, alkenyl, cycloalkyl, aryl, heteroaryl, and heterocyclyl are optionally substituted and $R_4$, $R_5$, $R_6$ and $R_8$ are each independently H or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

Figure 9:
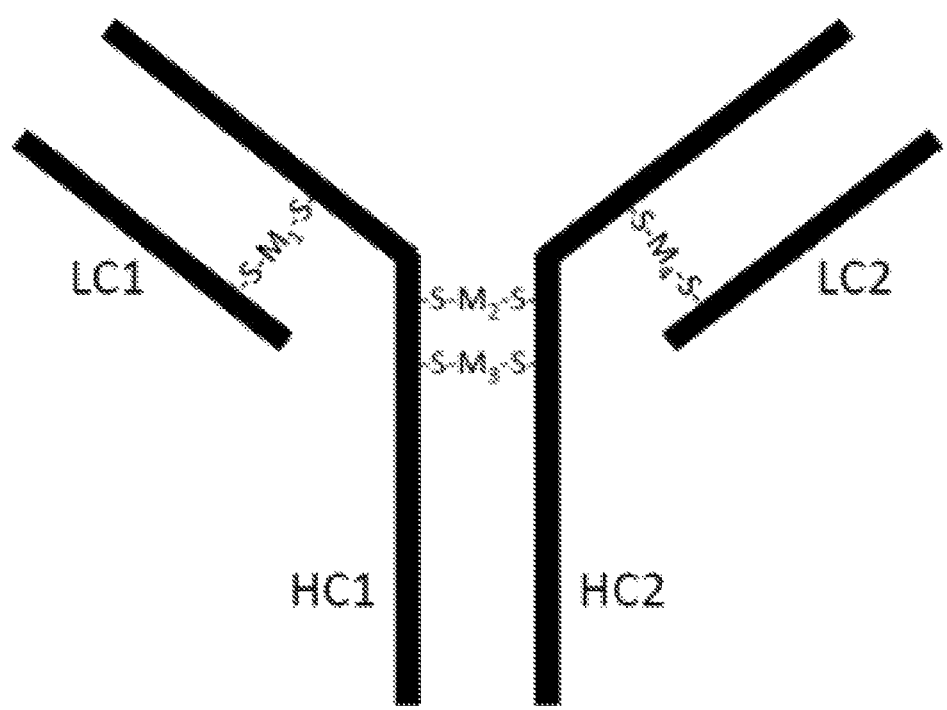
FIG. 9 provides a multimeric immunoglobulin conjugate.

The disclosure also provides a multimeric immunoglobulin conjugate having the structure as set forth in FIG. 9 wherein one or more M1, M2, M3, and/or M4 are each independently absent (i.e., the adjacent S atoms are directly connected to one another via a disulfide bond), or have the structure represented by formula (II)

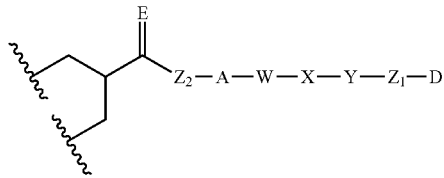

formula (II)

wherein

LC1 is a first antibody light chain,

LC2 is a second antibody light chain,

HC1 is a first antibody heavy chain, and

HC2 is a second antibody heavy chain;

wherein LC1, LC2, HC1 and/or HC2 comprise at least one antigen-binding domain;

E is O, S, $NR_4$, or $CR_5R_6$;

D is a biologically active molecule;

A is absent, a natural or non-natural amino acid, or a peptide comprising 2-20 amino acids;

W is absent, $-O-$, $-S-$, $-CR_5R_6-$, or $-NR_4-$;

X is absent, aryl, heteroaryl, cycloalkyl, heterocyclyl, wherein aryl, heteroaryl, cycloalkyl, and heterocyclyl are optionally substituted; and Y is absent,

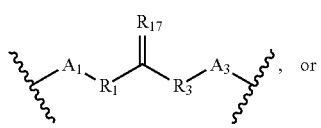, or

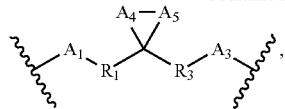, wherein $A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, $-CR_5R_6-$, $-O-$, $-C(=O)-$, $-O-C(=O)-$, $-C(=O)-O-$, $-O-C(=O)-O-$, $-C(=O)-(CH_x)_{p1}-$, $-C(=O)-O-(CH_x)_{p1}-$, $-(CH_x)_{p1}-C(=O)-$, $-(CH_x)_{p1}-C(=O)-O-$, $-(O-(CH_2)_{p2}-)_{p3}-$, $-((CH_2)_{p2}-O-)_{p3}-$, $-C(=S)-$, $-C(=S)-S-$, $-S-C(=S)-$, $-C(=S)-NH-$, $-S-C(=S)-S-$, $-S-$, $-SO-$, $-SO_2-$, $-NR_4-$, $-N(R_4)-C(=O)-N(R_8)-$, $-N(R_4)-C(=O)O-$, $-N(R_4)-C(=O)-$, $-C(=O)-N(R_4)-$, $-N(R_4)-C(=O)-$, $-C(=O)-N(R_4)-C(=O)-$, or $-O-C(=O)-NR_4-$, wherein alkyl, alkynyl, alkenyl, cycloalkyl, aryl, heteroaryl, and heterocyclyl are optionally substituted;

A4 and A5 are each independently $-O-$, $-S-$, $-NR_{18}-$, or $-CR_5R_6-$;

$R_{17}$ is O, S, $NR_{18}$, or $CR_5R_6$;

$R_{18}$ is H, alkyl, alkynyl, alkenyl, cycloalkyl, aryl, heteroaryl, heterocyclyl, or acyl, wherein alkyl, alkynyl, alkenyl, cycloalkyl, aryl, heteroaryl, heterocyclyl, and acyl are optionally substituted;

$R_4$, $R_5$, $R_6$ and $R_8$ are each independently H or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In an embodiment, the disclosure provides a multimeric immunoglobulin conjugate having the structure as set forth in FIG. 1), wherein $Z_2$ is represented by the following structural formula:

$$-Z_{2A}-Z_{2B}-Z_{2C}-Z_{2D}-,$$

wherein:

$Z_{2A}$, $Z_{2B}$, $Z_{2C}$ and $Z_{2D}$ are each independently absent, an amino acid, a peptide having 2-20 amino acids, an alkyl, an alkynyl, an alkenyl, a cycloalkyl, an aryl, a heteroaryl, a heterocyclyl, $-CR_5R_6-$, $-O-$, $-C(=O)-$, $-O-C(=O)-$, $-C(=O)-O-$, $-O-C(=O)-O-$, $-C(=O)-(CH_x)_{p1}-$, $-C(=O)-O-(CH_x)_{p1}-$, $-(CH_x)_{p1}-C(=O)-$, $-(CH_x)_{p1}-C(=O)-O-$, $-(O-(CH_2)_{p2}-)_{p3}-$, $-((CH_2)_{p2}-O-)_{p3}-$, $-C(=S)-$, $-C(=S)-S-$, $-C(=S)-NH-$, $-S-C(=S)-$, $-S-C(=S)-S-$, $-S-$, $-SO-$, $-SO_2-$, $-NR_4-$, $-N(R_4)-C(=O)-N(R_8)-$, $-N(R_4)-C(=O)O-$, $-N(R_4)-C(=O)-$, $-C(=O)-N(R_4)-$, $-C(=O)-N(R_4)-C(=O)-$, $-O-C(=O)-N(R_4)$, $-O-C(=S)-N(R_4)-$, or $-C(=S)-N(R_4)-$, wherein alkyl, alkynyl, alkenyl, cycloalkyl, aryl, heteroaryl, and heterocyclyl are optionally substituted and $R_4$, $R_5$, $R_6$ and $R_8$ are each independently H or a substituted or unsubstituted: alkyl, alkenyl, alkynyl, aryl, heteroaryl, or heterocyclyl; and $Z_1$ is represented by the following structural formula:

$$-Z_{1A}-Z_{1B}-Z_{1C}-Z_{1D}-,$$

wherein:

$Z_{1A}$, $Z_{1B}$, $Z_{1C}$ and $Z_{1D}$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(=O)—, —O—C(=O)—, —C(=O)—O—, —O—C(=O)—O—, —C(=O)—(CH$_x$)$_{p1}$—, —C(=O)—O—(CH$_x$)$_{p1}$—, —(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—S—, —C(=S)—NH—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, C(=O)—N(R$_4$)—C(=O)—, —O—C(=O)—N(R$_4$), —O—C(=S)—N(R$_4$)—, or —C(=S)—N(R$_4$)—,
- wherein alkyl, alkynyl, alkenyl, cycloalkyl, aryl, heteroaryl, and heterocyclyl are optionally substituted and R$_4$, R$_5$, R$_6$ and R$_8$ are each independently H or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In an embodiment, the disclosure provides a multimeric immunoglobulin conjugate having the structure as set forth in FIG. 1) wherein the conjugate is substantially stable under reducing conditions. In a further embodiment, the disclosure provides a multimeric immunoglobulin conjugate having the structure as set forth in FIG. 1) wherein the conjugate specifically binds a tumor-associated antigen.

In an embodiment, the disclosure provides a multimeric immunoglobulin conjugate having the structure as set forth in FIG. 1) wherein the conjugate specifically binds a tumor-associated antigen.

A. Antibodies and Multimeric Antigen-Binding Compounds

In certain embodiments, a multimeric immunoglobulin or an antigen-binding compound for use herein include antibodies. The term "antibody", as used herein, means any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or V$_H$) and a heavy chain constant region. The heavy chain constant region comprises three domains, C$_H$1, C$_H$2 and C$_H$3. Each light chain comprises a light chain variable region (abbreviated herein as LCVR or V$_L$) and a light chain constant region. The light chain constant region comprises one domain (C$_L$1). The V$_H$ and V$_L$ regions can be further subdivided into regions of hypervariability, termed complementarity determining regions (CDRs), interspersed with regions that are more conserved, termed framework regions (FR). Each V$_H$ and V$_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of an antibody may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a V$_H$ domain associated with a V$_L$ domain, the V$_H$ and V$_L$ domains may be situated relative to one another in any suitable arrangement. For example, the variable region may be dimeric and contain V$_H$-V$_H$, V$_H$-V$_L$ or V$_L$-V$_L$ dimers. Alternatively, the antigen-binding fragment of an antibody may contain a monomeric V$_H$ or V$_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) V$_H$-C$_H$1; (ii) V$_H$-C$_H$2; (iii) V$_H$-C$_H$3; (iv) V$_H$-C$_H$1-C$_H$2; (v) V$_H$-C$_H$-C$_H$2-C$_H$3; (vi) V$_H$-C$_H$2-C$_H$3; (vii) V$_H$-C$_L$; (viii) V$_L$-C$_H$1; (ix) V$_L$-C$_H$2; (x) V$_L$-C$_H$3; (xi) V$_L$-C$_H$2; (xii) V$_L$-C$_H$1-C$_H$2-C$_H$3; (xiii) V$_L$-C$_H$2-C$_H$3; and (xiv) V$_L$-C$_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antigen-binding fragment of an antibody of the present disclosure using routine techniques available in the art.

In certain embodiments of the disclosure, the antibodies of the disclosure are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the disclosure may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

In embodiments in which the multimeric immunoglobulin or antigen-binding compound for use herein is an antibody or antigen-binding fragment thereof, the antibody or antigen-binding fragment binds to one or more antigen binding partner. The antigen-binding partner may be a polypeptide such as a transmembrane molecule (e.g., receptor) or a growth factor. Exemplary antigens include, but are not limited to, molecules such as renin; a growth hormone, including human growth hormone and bovine growth hormone; growth hormone releasing factor; parathyroid hormone; thyroid stimulating hormone; lipoproteins; alpha1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-I-alpha); a serum albumin, such as human serum albumin; Muellerian-inhibiting substance; relaxin A-chain; relaxin B-chain; prorelaxin; mouse gonadotropin-associated peptide; a microbial protein, such as betalactamase; DNase; 19E; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like growth factor-1 and -II (IGF-1 and IGF-II); des(I-3)-IGF-1 (brain IGF-1), insulin-like growth factor binding proteins, EpCAM, GD3, FLT3, PSMA, PSCA, MUCI, MUCI6, STEAP, CEA, TENB2, EphA receptors, EphB receptors, folate receptor, FOLRI, mesothelin, cripto, alphavbeta6, integrins, VEGF, VEGFR, EGFR, transferrin receptor, 1RTAI, 1RTA2, 1RTA3, 1RTA4, 1RTA5; CD proteins such as CD2, CD3, CD4, CD5, CD6, CD8, CDII, CDI4, CDI9, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CDI52, or an antibody which binds to one or more tumor-associated antigens or cell-surface receptors disclosed in US Publication No. 2008/0171040 or US Publication No. 2008/0305044 and incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CDI8, an ICAM, VLA-4 and VCAM; a tumor associated antigen such as AFP, ALK, B7H4, BAGE proteins, β-catenin, brc-abl, BRCA1, BORIS, CA9 (carbonic anhydrase IX), caspase-8, CD20, CD40, CD123, CDK4, CEA, CLEC12A, c-kit, cMET, CTLA4, cyclin-B1, CYP1B1, EGFR, EGFRvIII, endoglin, Epcam, EphA2, ErbB2/Her2, ErbB3/Her3, ErbB4/Her4, ETV6-AML, Fra-1, FOLR1, GAGE proteins (e.g., GAGE-1, -2), GD2, GD3, GloboH, glypican-3, GM3, gp100, Her2, HLA/B-raf, HLA/EBNA1, HLA/k-ras, HLA/MAGE-A3, hTERT, IGF1R, LGR5, LMP2, MAGE proteins (e.g., MAGE-1, -2, -3, -4, -6, and -12), MART-1, mesothelin, ML-IAP, Muc1, Muc16 (CA-125), MUM1, NA17, NGEP, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSCA, PSGR, PSMA (FOLH1), RAGE proteins, Ras, RGS5, Rho, SART-1, SART-3, Steap-1, Steap-2, STn, survivin, TAG-72, TGF-β, TMPRSS2, Tn, TNFRSF17, TRP-1, TRP-2, tyrosinase, and uroplakin-3, and fragments of any of the above-listed polypeptides.

In some embodiments, the anti-body is an anti-PRLR antibody, e.g., those disclosed in U.S. Patent Publication No. 2015/0056222 A1.

Embodiments herein are target specific for therapeutic use. In one embodiment, multimeric immunoglobulin or antigen-binding compound are prepared to interact with and bind to antigens defined as tumor antigens, which include antigens specific for a type of tumor or antigens that are shared, overexpressed or modified on a particular type of tumor. Illustrative examples include: alpha-actinin-4 with lung cancer, ARTC1 with melanoma, BCR-ABL fusion protein with chronic myeloid leukemia, B-RAF, CLPP or Cdc27 with melanoma, CASP-8 with squamous cell carcinoma, and hsp70-2 with renal cell carcinoma as well as the following shared tumor-specific antigens, for example: BAGE-1, GAGE, GnTV, KK-LC-1, MAGE-A2, NA88-A, TRP2-INT2.

B. Biologically Active Molecules

Biologically active molecules herein (also referred to herein as "drugs," "toxins," "cytotoxic agents," "chemotherapeutic agents," and the like) include any molecules that have a therapeutic use in a mammal when targeted to a specific cell, cell type, or tissue. In typical embodiments the molecule is beneficially delivered to a target within the mammal and in particular is beneficially delivered to and then within a cell (e.g., endocytosis) as compared to molecules released into the vascular or lymphatic systems.

In one aspect, biologically active molecules are compounds that result in the inhibition, retardation, reduction, and/or prevention of cell growth. Biologically active molecules can also result in cell death via necrosis or apoptosis. Illustrative biologically active molecules for use in conjugate compounds described herein include: maytansinoids (e.g., DM1, DM4, or derivative thereof, etc.), auristatins (e.g., MMAE, MMAD, MMAF, etc.), duocarmycin (e.g., MGBA), dolastatin, toxoids, and other chemotherapeutically effective drugs. In some embodiments, biologically active molecule (D) has the following structure:

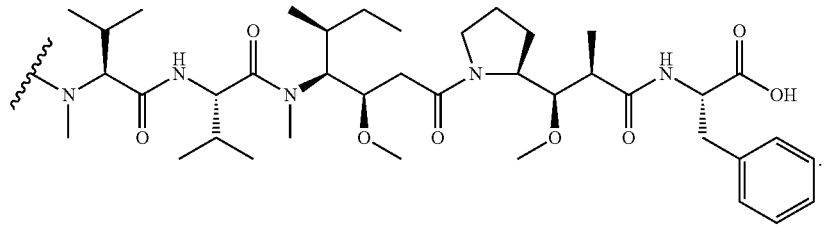 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

Other specific examples of biologically active molecules that can be used in the context of the present disclosure include, e.g., 1-dehydrotestosterone, 2-pyrrolinodoxorubicin, 5-fluorouracil, 6-mercaptopurine, 6-thioguanine, amanitin, actinomycin D, anthracycline (e.g., PNU-159682), anthramycin (AMC), bleomycin, busulfan, calicheamicins, carmustine cisplatin, colchicin, cyanomorpholino-doxorubicin, cyclophosphamide, cytarabine, cytochalasin B, dactinomycin, daunorubicin, decarbazine, dibromomannitol, dihydroxy anthracin dione, doxorubicin, emetine, epirubicin, ethidium bromide, etoposide, gramicidin D, glucocorticoids, lidocaine, lomustine (CCNU), mechlorethamine, melphalan, methotrexate, mithramycin, mitomycin, mitoxantrone, morpholino-doxorubicin, procaine, propranolol, puromycin, pyrrolobenzodiazapines, sibiromycin, streptozotocin, taxol, tenoposide, tetracaine, thioepa chlorambucil, trichothecenes, tubulysin, vincristine, and stereoisomers, isosteres, analogs or derivatives of any of the foregoing.

In one embodiment the biologically active molecule is a maytansinoid or a maytansinoid analog. Exemplary maytansinoids for use herein are described in Widdison et al., J. Med. Chem., 2006, 49, 4392-4408, incorporated by reference herein for all purposes. In some embodiments, the biologically active molecule is a maytansinoid described in WO 2014/145090A1.

Examples of cytotoxic agents that can be used in the context of the present disclosure also include, but are not limited to, 1-(2chloroethyl)-1,2-dimethanesulfonyl hydrazide, 1,8-dihydroxy-bicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins, camptothecin, carminomycins, carmustine, cemadotins, cisplatin, colchicin, combretastatins, cyclophosphamide, cytarabine, cytochalasin B, dactinomycin, daunorubicin, decarbazine, diacetoxypentyldoxorubicin, dibromomannitol, dihydroxy anthracin dione, disorazoles, dolastatin, doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vinca alkyloids, vindesine, vinorelbines, spliceostatin, amanatin, or calicheamicin and derivatives of any of the foregoing. According to certain embodiments, the cytotoxic agent is a maytansinoid such as DM1 or DM4, a tomaymycin derivative, or a dolastatin derivative. Other cytotoxic agents known in the art are contemplated within the scope of the present disclosure, including, e.g., protein toxins such ricin, *C. difficile* toxin, pseudomonas exotoxin, ricin, diphtheria toxin, botulinum toxin, bryodin, saporin, pokeweed toxins (i.e., phytolaccatoxin and phytolaccigenin), and others such as those set forth in Sapra et al., *Pharmacol. & Therapeutics*, 2013, 138:452-469.

In an embodiment, the present disclosure relates to conjugates, e.g., compounds of formula (I), formula (II), or formula (III), wherein the biologically active molecule (D) is a cytotoxic biologically active macrolide. In a further embodiment, the present disclosure provides maytansinoid as represented by formula (I)(a) as biologically active macrolide:

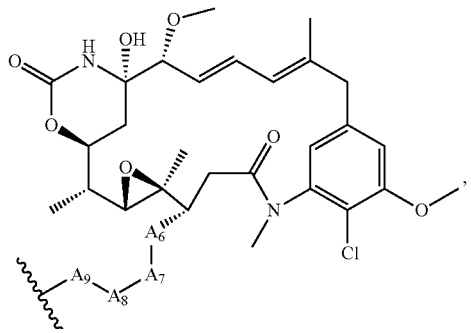

(I)(a)

wherein $A_6$, $A_7$, $A_8$, $A_9$ are each independently absent, an amino acid, N-alkyl amino acid, a peptide having 2-20 amino acids, an alkyl, an alkenyl, an alkynyl, a cycloalkyl, an aryl, a heteroaryl, a heterocyclyl, —$CR_5R_6$—, —O—, —C(=O)—, —O—, —C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—)$_{p3}$—, —(($CH_2)_{p2}$—O—)$_{p3}$—, —C(=S)—, —C(=S)—NH—, —C(=S)—S—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, —O—C(=O)—$NR_4$, further wherein alkyl, alkynyl, alkenyl, cycloalkyl, aryl, heteroaryl, and heterocyclyl are optionally substituted; and $R_4$, $R_5$, $R_6$ and $R_8$ are each independently H, or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In some embodiments, the biologically active molecule (D) has the following structure:

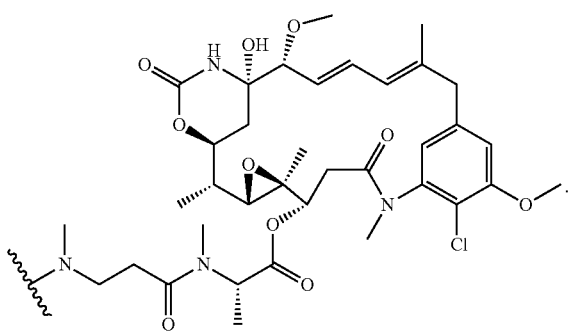 [SMILES: *N(C)CCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In a further embodiment, the maytansinoid is represented by the following structural formula (II)(a):

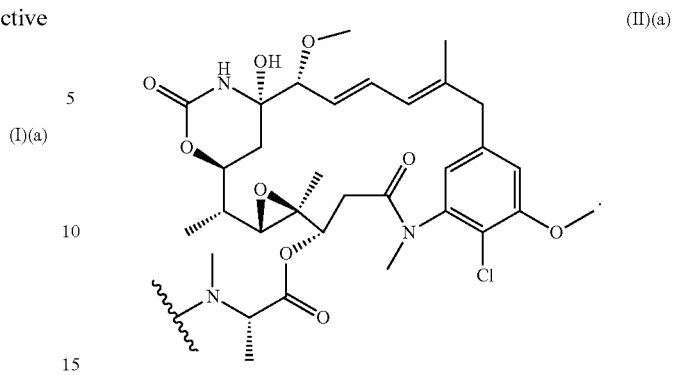

(II)(a)

C. Linkers

The linkers provided herein covalently connect a biologically active compound (e.g., cytotoxic agent) to sulfhydryl groups (e.g., of cysteine residues) of a multimeric antigen-binding compound (e.g., antibody). In certain aspects, the linkers connect two sulfhydryl groups via 3-carbon bridge. Such linkers can serve to reconnect cysteine residues of an antibody disulfide that is cleaved during the conjugation process.

In an embodiment, the disclosure provides linker represented by formula (IV):

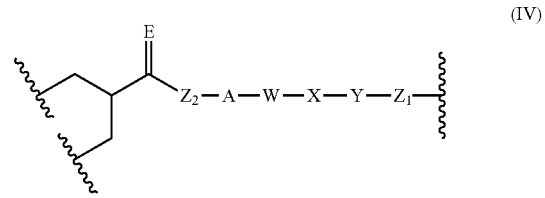

(IV)

wherein:

$Z_2$ and $Z_1$ are each independently absent or a spacer;

A is absent, a natural or non-natural amino acid, or a peptide comprising 2-20 amino acids;

W is absent, —O—, —S—, —$CR_5R_6$—, or —$NR_4$—;

X is absent, aryl, heteroaryl, cycloalkyl, heterocyclyl, wherein aryl, heteroaryl, cycloalkyl, and heterocyclyl are optionally substituted;

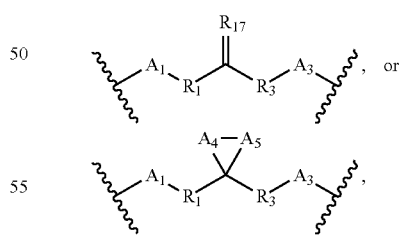

, or

Y is absent, wherein $A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—)$_{p3}$—

$-((CH_2)_{p2}-O-)_{p3}-$, $-C(=S)-$, $-C(=S)-S-$, $-C(=S)-NH-$, $-S-C(=S)-$, $-S-C(=S)-S-$, $-S-$, $-SO-$, $-SO_2-$, $-NR_4-$, $-N(R_4)-C(=O)-N(R_8)-$, $-N(R_4)-C(=O)O-$, $-N(R_4)-C(=O)-$, $-C(=O)-N(R_4)-$, $-C(=O)-N(R_4)-C(=O)-$, or $-O-C(=O)-NR_4-$, wherein alkyl, alkynyl, alkenyl, cycloalkyl, aryl, heteroaryl, and heterocyclyl are optionally substituted;

$A_4$ and $A_5$ are each independently $-O-$, $-S-$, $-NR_{18}-$, or $-CR_5R_6-$;

$R_{17}$ is O, S, $NR_{18}$, or $CR_5R_6$;

$R_{18}$ is H, alkyl, alkynyl, alkenyl, cycloalkyl, aryl, heteroaryl, heterocyclyl, or acyl, wherein alkyl, alkynyl, alkenyl, cycloalkyl, aryl, heteroaryl, heterocyclyl, and acyl are optionally substituted;

$R_4$, $R_5$, $R_6$ and $R_8$ are each independently H or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In a further embodiment, the disclosure provides linker represented by formula (IV) wherein $Z_2$ is represented by the following structural formula:

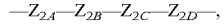
$-Z_{2A}-Z_{2B}-Z_{2C}-Z_{2D}-$, wherein:

$Z_{2A}$, $Z_{2B}$, $Z_{2C}$ and $Z_{2D}$ are each independently absent, an amino acid, a peptide having 2-20 amino acids, an alkyl, an alkynyl, an alkenyl, a cycloalkyl, an aryl, a heteroaryl, a heterocyclyl, $-CR_5R_6-$, $-O-$, $-C(=O)-$, $-O-C(=O)-$, $-C(=O)-O-$, $-O-C(=O)-O-$, $-C(=O)-(CH_x)_{p1}-$, $-C(=O)-O-(CH_x)_{p1}-$, $-(CH_x)_{p1}-C(=O)-$, $-(CH_x)_{p1}-C(=O)-O-$, $-(O-(CH_2)_{p2}-)_{p3}-$, $-((CH_2)_{p2}-O-)_{p3}-$, $-C(=S)-$, $-C(=S)-S-$, $-C(=S)-NH-$, $-S-C(=S)-$, $-S-C(=S)-S-$, $-S-$, $-SO-$, $-SO_2-$, $-NR_4-$, $-N(R_4)-C(=O)-N(R_8)-$, $-N(R_4)-C(=O)O-$, $-N(R_4)-C(=O)-$, $-C(=O)-N(R_4)-$, $-C(=O)-N(R_4)-C(=O)-$, $-O-C(=O)-N(R_4)$, $-O-C(=S)-N(R_4)-$, or $-C(=S)-N(R_4)-$, wherein alkyl, alkynyl, alkenyl, cycloalkyl, aryl, heteroaryl, and heterocyclyl are optionally substituted and $R_4$, $R_5$, $R_6$ and $R_8$ are each independently H, or a substituted or unsubstituted: alkyl, alkenyl, alkynyl, aryl, heteroaryl, or heterocyclyl; and wherein $Z_1$ is represented by the following structural formula:

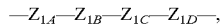
$-Z_{1A}-Z_{1B}-Z_{1C}-Z_{1D}-$, wherein:

$Z_{1A}$, $Z_{1B}$, $Z_{1C}$ and $Z_{1D}$ are each independently absent, an amino acid, a peptide having 2-20 amino acids, an alkyl, an alkynyl, an alkenyl, a cycloalkyl, an aryl, a heteroaryl, a heterocyclyl, $-CR_5R_6-$, $-O-$, $-C(=O)-$, $-O-C(=O)-$, $-C(=O)-O-$, $-O-C(=O)-O-$, $-C(=O)-(CH_x)_{p1}-$, $-C(=O)-O-(CH_x)_{p1}-$, $-(CH_x)_{p1}-C(=O)-$, $-(CH_x)_{p1}-C(=O)-O-$, $-(O-(CH_2)_{p2}-)_{p3}-$, $-((CH_2)_{p2}-O-)_{p3}-$, $-C(=S)-$, $-C(=S)-S-$, $-C(=S)-NH-$, $-S-C(=S)-$, $-S-C(=S)-S-$, $-S-$, $-SO-$, $-SO_2-$, $-NR_4-$, $-N(R_4)-C(=O)-N(R_8)-$, $-N(R_4)-C(=O)O-$, $-N(R_4)-C(=O)-$, $-C(=O)-N(R_4)-$, $-C(=O)-N(R_4)-C(=O)-$, $-O-C(=O)-N(R_4)$, $-O-C(=S)-N(R_4)-$, or $-C(=S)-N(R_4)-$, wherein alkyl, alkynyl, alkenyl, cycloalkyl, aryl, heteroaryl, and heterocyclyl are optionally substituted and $R_4$, $R_5$, $R_6$ and $R_8$ are each independently H, or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In an embodiment, the maytansinoid provides part of the linker.

In an embodiment, the disclosure provides compounds of formula (I), formula (II), formula (III), or formula (IV), wherein A is an amino acid selected from the group consisting of alanine, aspartic acid, glutamic acid, phenylalanine, glycine, histidine, isoleucine, lysine, leucine, methionine, asparagine, proline, glutamine, arginine, serine, threonine, valine, tryptophan, tyrosine, cysteine, and citrulline.

In an embodiment, the disclosure provides compounds of formula (I), formula (II), formula (III), or formula (IV), wherein A is a peptide selected from the group consisting of valine-citrulline, citrulline-valine, lysine-phenylalanine, phenylalanine-lysine, valine-asparagine, asparagine-valine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, asparagine-alanine.

In an embodiment, the disclosure provides compounds of formula (I), formula (II), formula (III), or formula (IV), wherein X is an aryl selected from the group consisting of

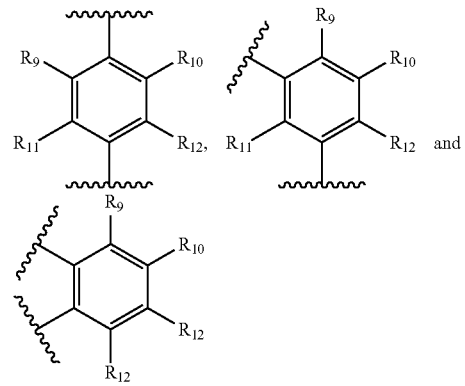

wherein $R_9$, $R_{10}$, $R_{11}$, and $R_{12}$ are each independently H, an alkyl, cycloalkyl, aryl, heteroaryl, heterocyclyl, halogen, $NR_{13}R_{14}$, nitro, cyano, $-OH$, $-O-C(=O)-R_{15}$, $-C(=O)-R_{15}$, $-C(=O)-O-R_{15}$, $-C(=O)-NR_{13}R_{14}$; and further wherein, alkyl, cycloalkyl, aryl, heteroaryl, and heterocyclyl are optionally substituted; and $R_{13}$ and $R_{14}$ are each independently H or an optionally substituted alkyl; and $R_{15}$ is an optionally substituted alkyl.

In one aspect, the linkers are useful to covalently link ligands with therapeutic agents and markers. In another aspect, the linkers improve chemical and/or systemic stability of the attached moieties. In another aspect, the linkers reduce in vivo toxicity of the attached moieties. In another aspect, the linkers improve pharmacokinetics, pharmacodynamics, and/or bioavailability of the attached moieties. In one aspect, the linkers are cleavable linkers, i.e., the linkers can be cleaved and release a biologically active molecule at a site in or near a target cell or a cell population in a pharmacologically effective form. In another aspect, the linkers are non-cleavable, but the antibody-drug conjugate can be degraded to release its attached moieties in a pharmacologically effective form.

D. Exemplary Conjugates

In one aspect, the disclosure provides a multimeric antigen-binding compound-conjugate having the formula (I)

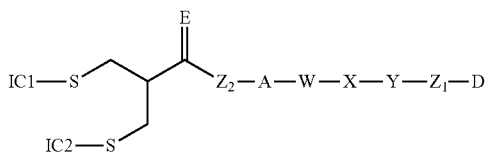

wherein:

IC1 is a first immunoglobulin chain, and IC2 is a second immunoglobulin chain; further wherein IC1 and/or IC2 comprise at least one antigen-binding domain;

$Z_1$ and $Z_2$ are each independently absent or a spacer;

E is O, S, $NR_4$, or $CR_5R_6$;

D is a biologically active molecule;

A is absent or a natural or non-natural amino acid, or a peptide comprising 2-20 amino acids;

W is absent, —O—, —S—, —$CR_5R_6$—, —$NR_4$—;

X is absent, aryl, heteroaryl, cycloalkyl, heterocyclyl,
    wherein aryl, heteroaryl, cycloalkyl, and heterocyclyl are optionally substituted; and Y is absent,

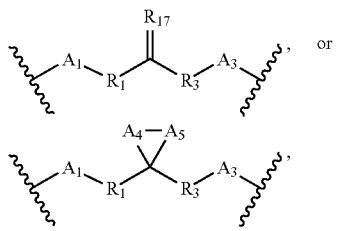

wherein $A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, $((CH_2)_{p2}$—O—$)_{p3}$—, —C(=S)—, —C(=S)—S—, —S—C(=S)—, —C(=S)—NH—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, or —O—C(=O)—$NR_4$—,
    wherein alkyl, alkynyl, alkenyl, cycloalkyl, aryl, heteroaryl, and heterocyclyl are optionally substituted;

$A_4$ and $A_5$ are each independently —O—, —S—, —$NR_{18}$—, —$CR_5R_6$—;

$R_{17}$ is O, S, $NR_{18}$, or $CR_5R_6$;

$R_{18}$ is H, alkyl, alkynyl, alkenyl, cycloalkyl, aryl, heteroaryl, heterocyclyl, or acyl,
    wherein alkyl, alkynyl, alkenyl, cycloalkyl, aryl, heteroaryl, heterocyclyl, and acyl are optionally substituted;

$R_4$, $R_5$, $R_6$ and $R_8$ are each independently H, or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In an embodiment, the disclosure provides the antigen-binding compound-conjugate represented by formula (I), wherein IC1 is a first heavy chain of an antibody or antigen-binding portion thereof; and IC2 is a second heavy chain of the antibody or antigen-binding portion thereof. In certain sub-embodiments wherein IC1 and IC2 are antibody heavy chains, one or more of IC1 and/or IC2 may each be independently associated with or connected to an antibody light chain or antigen-binding portion thereof (e.g., forming a complete tetrameric antibody structure). In a further embodiment, the disclosure provides the antigen-binding compound-conjugate represented by formula (I), wherein the antigen-binding compound-conjugate is substantially stable under reducing conditions. In a further embodiment, the disclosure provides the antigen-binding compound-conjugate represented by formula (I), wherein D is a cytotoxic agent.

In an embodiment, the disclosure provides the antigen-binding compound-conjugate represented by formula (I), wherein IC1 is a heavy chain of an antibody or antigen-binding portion thereof; and IC2 is a light chain of the antibody or antigen-binding portion thereof. In certain sub-embodiments wherein IC1 is an antibody heavy chain and IC2 is an antibody light chain, the IC1/IC2 construct may be associated with or connected to another antibody heavy chain/light chain pair (e.g., forming a complete tetrameric antibody structure). In a further embodiment, the disclosure provides the antigen-binding compound-conjugate represented by formula (I), wherein the antigen-binding compound-conjugate is substantially stable under reducing conditions. As used herein, the expression "substantially stable," when used in the context of an antibody or other multimeric immunoglobulin means that the re-joined disulfide linking two separate polypeptide chains can hold the antibody or immunoglobulin substantially intact under reducing conditions such as the reducing environment of an SDS-PAGE gel, or in the presence of serum (e.g., human, monkey, bovine, mouse, rat, etc.) at 37° C., or at temperatures greater than 90° C., etc. In a further embodiment, the disclosure provides the antigen-binding compound-conjugate represented by formula (I), wherein D is a cytotoxic agent. In a further embodiment, the disclosure provides the antigen-binding compound-conjugate represented by formula (I), wherein the antigen-binding compound-conjugate specifically binds a tumor-associated antigen.

In an embodiment, the disclosure provides the antigen-binding compound-conjugate represented by formula (I), wherein the antigen-binding compound-conjugate is substantially stable under reducing conditions. In a further embodiment, the disclosure provides the antigen-binding compound-conjugate represented by formula (I), wherein D is a cytotoxic agent. In a further embodiment, the disclosure provides the antigen-binding compound-conjugate represented by formula (I), wherein the antigen-binding compound-conjugate specifically binds a tumor-associated antigen.

In an embodiment, the disclosure provides the antigen-binding compound-conjugate represented by formula (I), wherein D is a cytotoxic agent, including, e.g., any cytotoxic agent as set forth elsewhere herein.

In an embodiment, the disclosure provides the antigen-binding compound-conjugate represented by formula (I), wherein the antigen-binding compound-conjugate specifically binds a tumor-associated antigen.

In some embodiments, the carbon of —C(=E)- is not directly bonded to an aryl group. In some embodiments, the carbon of —C(=E)- is not directly bonded to a phenyl group.

In one embodiment, the disclosure provides antigen-binding compound-conjugate represented by formula (I), $R_4$, $R_5$, $R_6$ and $R_8$ are each independently H or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In an embodiment, the disclosure provides a compound of formula (I) represented by the following structure (I)(b):

(I)(b).

In an embodiment, the disclosure provides the antigen-binding compound-conjugate represented by formula (I)(b), wherein IC1 is a first heavy chain of an antibody or antigen-binding portion thereof; and IC2 is a second heavy chain of the antibody or antigen-binding portion thereof. In a further embodiment, the disclosure provides the antigen-binding compound-conjugate represented by formula (I)(b), wherein the antigen-binding compound-conjugate is substantially stable under reducing conditions.

In an embodiment, the disclosure provides the antigen-binding compound-conjugate represented by formula (I)(b), wherein IC1 is a heavy chain of an antibody or antigen-binding portion thereof; and IC2 is a light chain of the antibody or antigen-binding portion thereof. In a further embodiment, the disclosure provides the antigen-binding compound-conjugate represented by formula (I)(b), wherein the antigen-binding compound-conjugate is substantially stable under reducing conditions.

Figure 10:
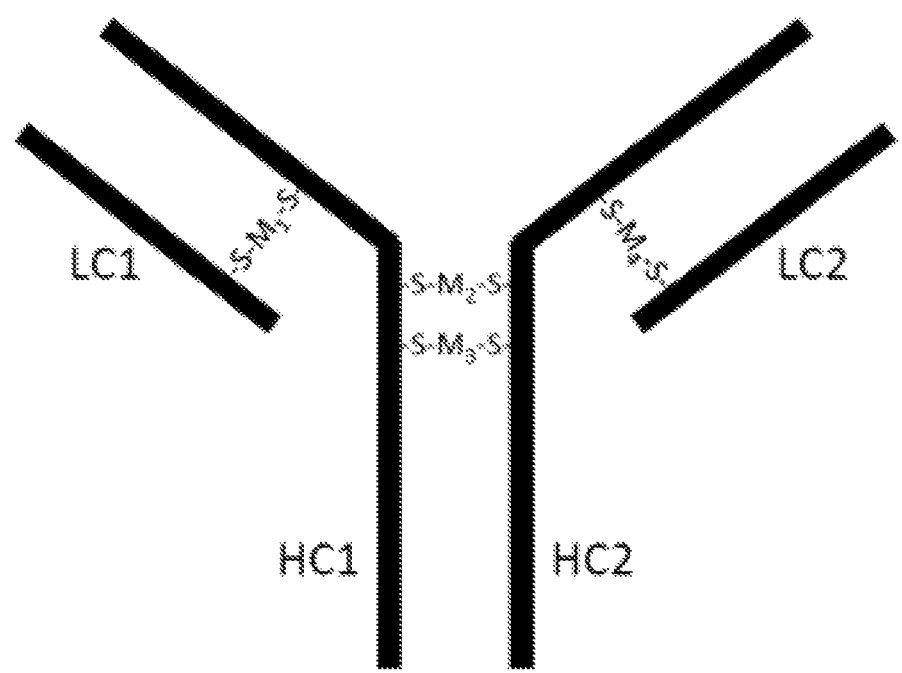
FIG. 10 provides a multimeric immunoglobulin conjugate.

In an aspect, the disclosure also provides a multimeric immunoglobulin conjugate having the structure as set forth in FIG. 10 wherein one or more M1, M2, M3, and/or M4 are each independently absent (i.e., the adjacent S atoms are directly connected to one another via a disulfide bond), or have the structure represented by formula (II)

wherein $Z_2$ is represented by the following structural formula:

—$Z_{2A}$—$Z_{2B}$—$Z_{2C}$—$Z_{2D}$—, wherein:

$Z_{2A}$, $Z_{2B}$, $Z_{2C}$ and $Z_{2D}$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —($(CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —N($R_4$)—C(=O)—N($R_8$)—, —N($R_4$)—C(=O)O—, —N($R_4$)—C(=O)—, —C(=O)—N($R_4$)—, —C(=O)—N($R_4$)—C(=O)—, —O—C(=O)—N($R_4$), —O—C(=S)—N($R_4$)—, or —C(=S)—N($R_4$)—, wherein alkyl, alkynyl, alkenyl, cycloalkyl, aryl, heteroaryl, and heterocyclyl are optionally substituted and $R_4$, $R_5$, $R_6$ and $R_8$ are each independently H or a substituted or unsubstituted: alkyl, alkenyl, alkynyl, aryl, heteroaryl, or heterocyclyl;

and $Z_1$ is represented by the following structural formula:

—$Z_{1A}$—$Z_{1B}$—$Z_{1C}$—$Z_{1D}$—, wherein:

$Z_{1A}$, $Z_{1B}$, $Z_{1C}$ and $Z_{1D}$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —($(CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —N($R_4$)—C(=O)—N($R_8$)—, —N($R_4$)—C(=O)O—, —N($R_4$)—C(=O)—, —C(=O)—N($R_4$)—, —C(=O)—N($R_4$)—C(=O)—, —O—C(=O)—N($R_4$), —O—C(=S)—N($R_4$)—, or —C(=S)—N($R_4$)—, wherein alkyl, alkynyl, alkenyl, cycloalkyl, aryl, heteroaryl, and heterocyclyl are optionally substituted and formula (II)

wherein

LC1 is a first antibody light chain,

LC2 is a second antibody light chain,

HC2 is a first antibody heavy chain, and

HC2 is a second antibody heavy chain;

wherein LC1, LC2, HC1 and/or HC2 comprise at least one antigen-binding domain; and E is O, S, $NR_4$, or $CR_5R_6$;
D is a biologically active molecule;
A is absent, a natural or non-natural amino acid, or a peptide comprising 2-20 amino acids;
W is absent, —O—, —S—, —$CR_5R_6$—, or —$NR_4$—;
X is absent, aryl, heteroaryl, cycloalkyl, heterocyclyl,
 wherein aryl, heteroaryl, cycloalkyl, and heterocyclyl are optionally substituted; and
Y is absent,

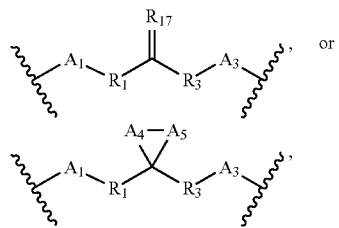

, or wherein $A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —$((CH_2)_{p2}$—O—$)_{p3}$—, —C(=S)—, —C(=S)—S—, —S—C(=S)—, —C(=S)—NH—, —S—C(=S)—S—, —S—, —SO—, —$SO_2$—, —$NR_4$—, —$N(R_4)$—C(=O)—N(R)—, —$N(R_4)$—C(=O)O—, —$N(R_4)$—C(=O)—, —C(=O)—$N(R_4)$—, —C(=O)—$N(R_4)$—C(=O)—, —O—C(=O)—$NR_4$—,
 wherein alkyl, alkynyl, alkenyl, cycloalkyl, aryl, heteroaryl, and heterocyclyl are optionally substituted;
$A_4$ and $A_5$ are each independently —O—, —S—, —$NR_{18}$—, or —$CR_5R_6$—;
$R_{17}$ is O, S, $NR_{18}$, or $CR_5R_6$;
$R_{18}$ is H, alkyl, alkynyl, alkenyl, cycloalkyl, heteroaryl, heterocyclyl, or acyl,
 wherein alkyl, alkynyl, alkenyl, cycloalkyl, heteroaryl, heterocyclyl, and acyl are optionally substituted;
$R_4$, $R_5$, $R_6$ and $R_8$ are each independently H, or a substituted or unsubstituted: alkyl, alkenyl, alkynyl, aryl, heteroaryl, or heterocyclyl;
p1, p2 and p3 are each independently 0, or an integer from 1 to 100; and
x is 0, 1 or 2.

In an embodiment, the disclosure provides a multimeric immunoglobulin conjugate having the structure as set forth in FIG. 1), wherein $Z_2$ is represented by the following structural formula:

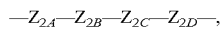

wherein:
$Z_{2A}$, $Z_{2B}$, $Z_{2C}$ and $Z_{2D}$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —C(=O)—, —$(CH_x)_{p1}$—C(=O)—O—, —(O—$(CH_2)_{p2}$—$)_{p3}$—, —$((CH_2)_{p2}$—O—$)_{p3}$—, —C(=S)—, —C(=S)—S—, —S—C(=S)—, —C(=S)—NH—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)—O—, —$N(R_4)$—C(=O)—, —C(=O)—$N(R_4)$—, —O—C(=O)—$N(R_4)$, —O—C(=S)—$N(R_4)$—, or —C(=S)—$N(R_4)$—,
 wherein alkyl, alkynyl, alkenyl, cycloalkyl, aryl, heteroaryl, and heterocyclyl are optionally substituted and $R_4$, $R_5$, $R_6$ and $R_8$ are each independently H, or a substituted or unsubstituted: alkyl, alkenyl, alkynyl, aryl, heteroaryl, or heterocyclyl; and
$Z_1$ is represented by the following structural formula:

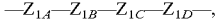

wherein:
$Z_{1A}$, $Z_{1B}$, $Z_{1C}$ and $Z_{1D}$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —O—$(CH_2)_{p2}$—$)_{p3}$—, —$((CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, C(=O)—$N(R_4)$—C(=O)—, —O—C(=O)—$N(R_4)$, —O—C(=S)—$N(R_4)$—, or —C(=S)—$N(R_4)$—,
 wherein alkyl, alkynyl, alkenyl, cycloalkyl, aryl, heteroaryl, and heterocyclyl are optionally substituted and $R_4$, $R_5$, $R_6$ and $R_8$ are each independently H or a substituted or unsubstituted: alkyl, alkenyl, alkynyl, aryl, heteroaryl, or heterocyclyl;
p1, p2 and p3 are each independently 0, or an integer from 1 to 100; and
x is 0, 1 or 2.

In an embodiment, the disclosure provides a multimeric immunoglobulin conjugate having the structure as set forth in FIG. 1) wherein the conjugate is substantially stable under reducing conditions. In a further embodiment, the disclosure provides a multimeric immunoglobulin conjugate having the structure as set forth in FIG. 1) wherein the conjugate specifically binds a tumor-associated antigen.

In an embodiment, the disclosure provides a multimeric immunoglobulin conjugate having the structure as set forth in FIG. 1) wherein the conjugate specifically binds a tumor-associated antigen.

In an embodiment, the formula (II) is represented by the following structure (II)(b):

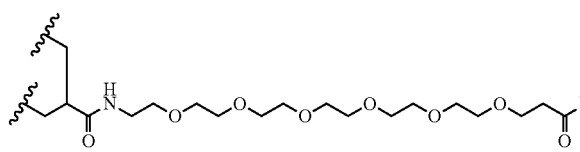

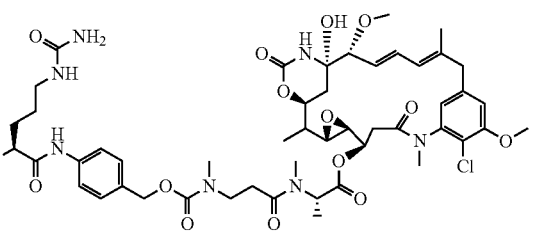

Provided herein are compounds of the following formula:

IG(SP$^A$-A-W-X-Y-Z$_1$-D)$_x$ wherein:
IG is an antigen-binding immunoglobulin;
x is an integer from 1 to 4;
SP$^A$ is:

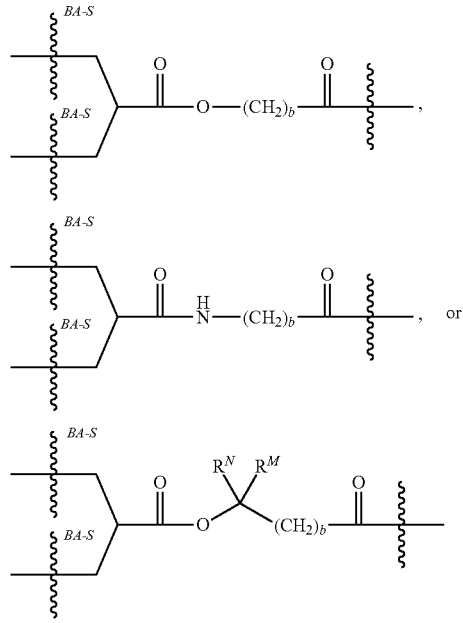

wherein:
R$^N$ is a hydrogen atom or alkyl;
R$^M$ is alkyl;
the two bonds represented by

are bonds to cysteines of the immunoglobulin and
b is an integer from 2 to 8;
and A, W, X, Y, Z$_1$, and D are as defined herein.

In some embodiments, the compound has the following structure:

IG(SP$^A$-A-D)$_x$ wherein:
IG is an antigen-binding immunoglobulin;
x is an integer from 1 to 4;
SP$^A$ is:

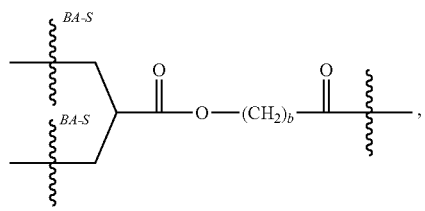

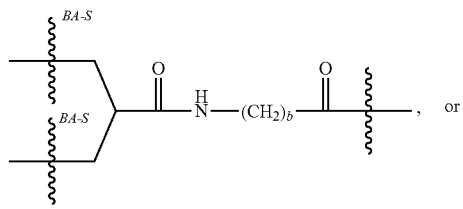

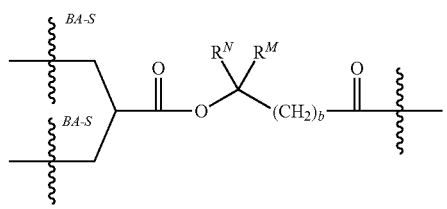

wherein:
R$^N$ is a hydrogen atom or alkyl;
R$^M$ is alkyl;
the two bonds represented by

are bonds to cysteines of the immunoglobulin; and
b is an integer from 2 to 8; and
A is as defined elsewhere herein.

In some embodiments, A is a dipeptide.
In some embodiments, SP$^A$ is:

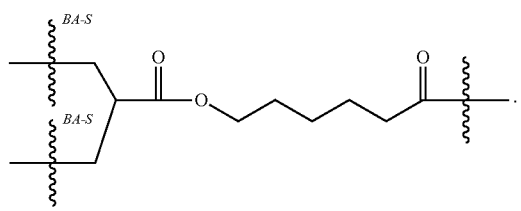

In some embodiments, SP$^A$ is:

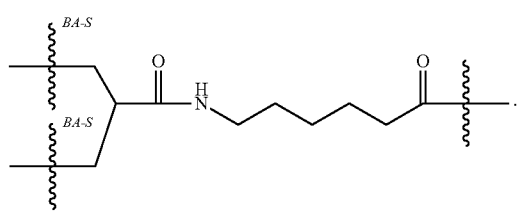

In some embodiments, SP$^A$ is:

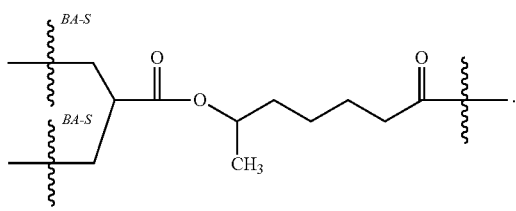

In some embodiments, SP$^A$ is:

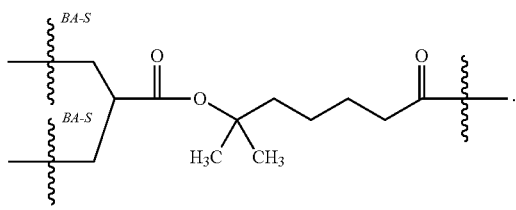 [SMILES: *CC(C*)C(=O)OC(C)(C)CCCCC(*)=O]

In some embodiments, SP$^A$-A- is:

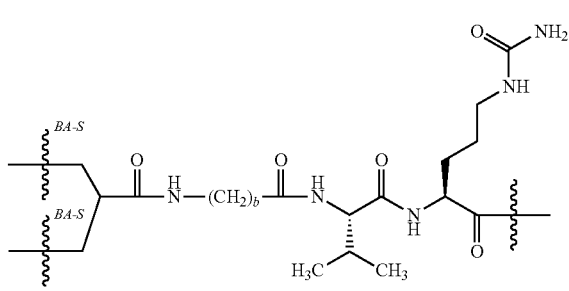

wherein:
the two bonds represented by

are bonds to cysteines of the immunoglobulin; and
b is an integer from 2 to 8.

In some embodiments, SP$^A$-A- is:

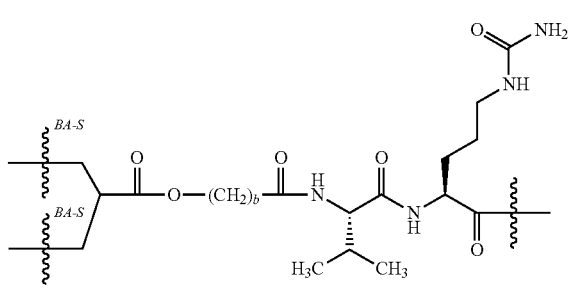

wherein:
the two bonds represented by

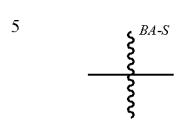

are bonds to cysteines of the immunoglobulin; and
b is an integer from 2 to 8.

In some embodiments, SP$^A$-A- is:

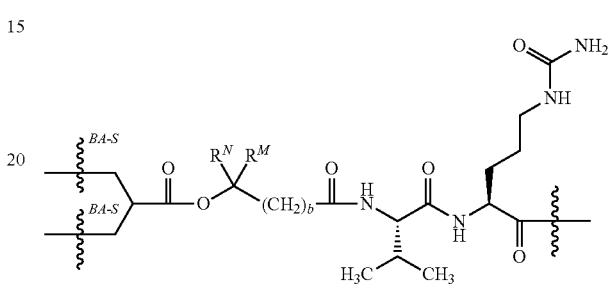

wherein:
$R^N$ is a hydrogen atom or alkyl;
$R^M$ is alkyl;
the two bonds represented by

are bonds to cysteienes of the immunoglobulin; and
b is an integer from 2 to 8.

In some embodiments, SP$^A$-A- is:

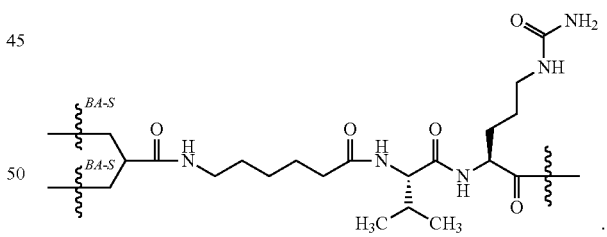

In some embodiments, SP$^A$-A- is:

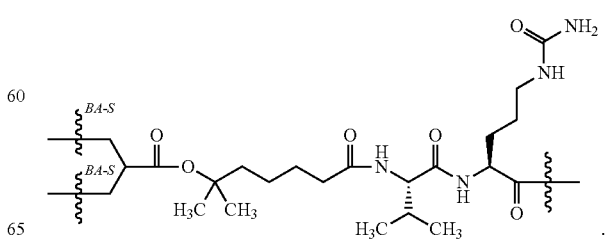

In some embodiments, $SP^A$-A- is:

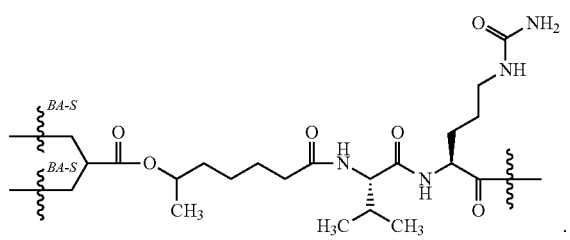

In some embodiments, SPA-A- is:

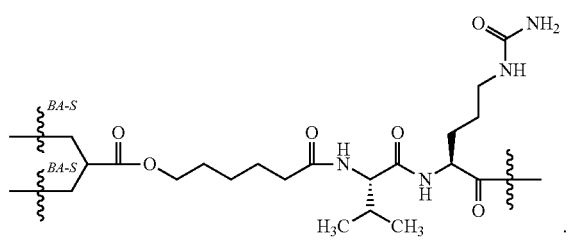 [SMILES: *CC(C*)C(=O)OCCCCCC(=O)N[C@H](C(=O)N[C@@H](CCCNC(N)=O)C(*)=O)C(C)C]

Provided herein are also antibody-drug conjugates comprising an antibody, or antigen binding fragment thereof, wherein the antibody or antigen binding fragment thereof is conjugated to at least one moiety of Formula (A):

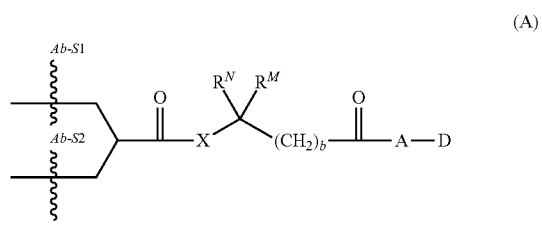

wherein:
Ab-S1 is a bond to a cysteine sulfur atom of the antibody or antigen binding fragment thereof;
Ab-S2 is a bond to a cysteine sulfur atom of the antibody or antigen binding fragment thereof;
X is $-N(R^A)-$ or $-O-$;
wherein $R^A$ is a hydrogen atom or alkyl;
$R^N$ and $R^M$ are each, independently, a hydrogen atom or alkyl;
A is absent, i.e., a bond, or a spacer comprising a peptide, wherein the peptide comprises 2-20 amino acids;
D is a biologically active molecule; and
b is an integer from 2 to 8.

In some embodiments, the antibody or antigen binding fragment thereof comprises at least one moiety of Formula (A) wherein Ab-S1 is a bond to a cysteine sulfur atom of a first heavy chain of the antibody or antigen binding fragment thereof and AB-S2 is a bond to a cysteine sulfur atom of a second heavy chain of the antibody or antigen binding fragment thereof.

In some embodiments, the antibody or antigen binding fragment thereof comprises at least one moiety of Formula (A) wherein Ab-S1 is a bond to a cysteine sulfur atom of a light chain of the antibody or antigen binding fragment thereof and AB-S2 is a bond to a cysteine sulfur atom of a heavy chain of the antibody of antigen binding fragment thereof.

In some embodiments, the antibody or antigen binding fragment thereof comprises:
(i) at least one moiety of Formula (A) wherein Ab-S1 is a bond to a cysteine sulfur atom of a first heavy chain of the antibody or antigen binding fragment thereof and AB-S2 is a bond to a cysteine sulfur atom of a second heavy chain of the antibody or antigen binding fragment thereof; and
i) (ii) at least one moiety of Formula (A) wherein Ab-S1 is a bond to a cysteine sulfur atom of a light chain of the antibody or antigen binding fragment thereof and AB-S2 is a bond to a cysteine sulfur atom of a heavy chain of the antibody of antigen binding fragment thereof.

In some embodiments, the antibody or antigen binding fragment thereof comprises two moieties of Formula (A) wherein Ab-S1 is a bond to a cysteine sulfur atom of a first heavy chain of the antibody or antigen binding fragment thereof and AB-S2 is a bond to a cysteine sulfur atom of a second heavy chain of the antibody or antigen binding fragment thereof.

In some embodiments, the antibody or antigen binding fragment thereof comprises:
(i) two moieties of Formula (A) wherein Ab-S1 is a bond to a cysteine sulfur atom of a first heavy chain of the antibody or antigen binding fragment thereof and AB-S2 is a bond to a cysteine sulfur atom of a second heavy chain of the antibody or antigen binding fragment thereof; and
(ii) two moieties of Formula (A) wherein Ab-S1 is a bond to a cysteine sulfur atom of a light chain of the antibody or antigen binding fragment thereof and AB-S2 is a bond to a cysteine sulfur atom of a heavy chain of the antibody of antigen binding fragment thereof.

In some embodiments, the antibody drug conjugate comprises an antibody.

In some embodiments, the antibody is an anti-PRLR antibody.

In some embodiments, X is $-N(R^A)-$. In certain embodiments, $R^A$ is a hydrogen atom.

In some embodiments, X is $-O-$.

In some embodiments, $R^N$ and $R^M$ are both hydrogen atoms. In some embodiments, $R^N$ is a hydrogen atom and $R^M$ is alkyl. In some embodiments, $R^N$ and $R^M$ are both alkyl.

In some embodiments, X is $-O-$ and $R^N$ and $R^M$ are both hydrogen atoms. In some embodiments, X is $-O-$, $R^N$ is a hydrogen atom, and $R^M$ is alkyl. In some embodiments, X is $-O-$ and $R^N$ and $R^M$ are both alkyl. In some embodiments, X is $-O-$, $R^N$ is a hydrogen atom, and $R^M$ is methyl. In some embodiments, X is $-O-$ and $R^N$ and $R^M$ are both methyl.

In some embodiments, b is an integer from 3-6. In some embodiments, b is 4. In some embodiments, $R^N$ and $R^M$ are both hydrogen atoms and b is 4.

In some embodiments, X is —O—, $R^N$ and $R^M$ are both hydrogen atoms, and b is 4. In some embodiments, X is —O—, $R^N$ and $R^M$ are both alkyl, and b is 4. In some embodiments, X is —O—, $R^N$ and $R^M$ are both methyl, and b is 4. In some embodiments, X is —O—, $R^N$ is alkyl, $R^M$ is a hydrogen atom, and b is 4.

In some embodiments, X is —N(H)—, $R^N$ and $R^M$ are both hydrogen atoms, and b is 4.

In some embodiments, $R^A$, $R^N$ and $R^M$ are each, independently is a hydrogen atom or $C_{1-6}$ alkyl.

In some embodiments, A is a spacer comprising a dipeptide. In some embodiments, the dipeptide is valine-citrulline. In some embodiments, A is:

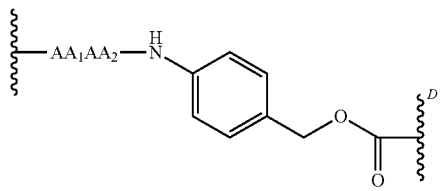

wherein

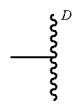

is the bond to D, and $AA_1$ and $AA_2$ are each, independently, an amino acid.

In some embodiments, $AA^1$-$AA^2$ is: valine-citrulline, citrulline-valine, lysine-phenylalanine, phenylalanine-lysine, valine-asparagine, asparagine-valine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, or asparagine-alanine.

In some embodiments, A is:

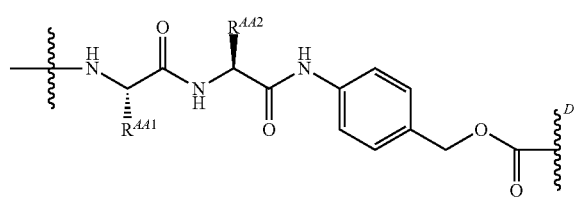

wherein

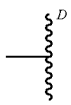

is the bond to D and $R^{AA1}$ and $R^{AA2}$ are each, independently, an amino acid side chain. As used herein, "amino acid side chain" refers the monovalent non-hydrogen substituent bonded to the α-carbon of an α-amino acid, including natural and non-natural amino acids. Exemplary amino acid side chains include, but are not limited to, the α-carbon substituent of alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, and citrulline.

In some embodiments, A is:

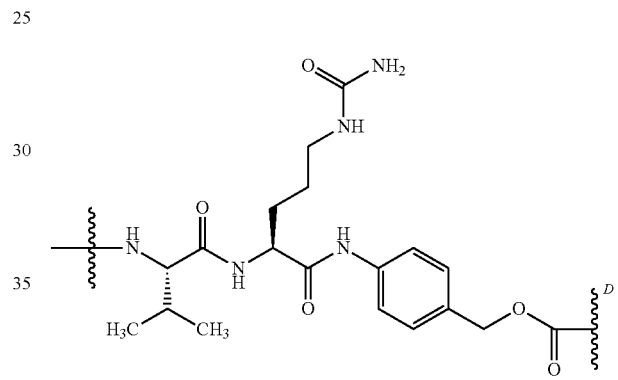

wherein

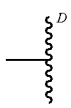

is the bond to D.

In some embodiments, A is absent.

In some embodiments, D is an auristatin or maytansinoid.

In some embodiments, D is an auristatin, wherein the auristatin is MMAE, MMAD, or MMAF.

In some embodiments, D is MMAF.

In some embodiments, D is a maytansinoid

In some embodiments, A is a spacer comprising a peptide comprising 2-20 amino acids and D is a maytansinoid.

In some embodiments, A is absent and D is an auristatin.

In some embodiments, A is represented by formula (I)(a) as biologically active macrolide:

(I)(a)

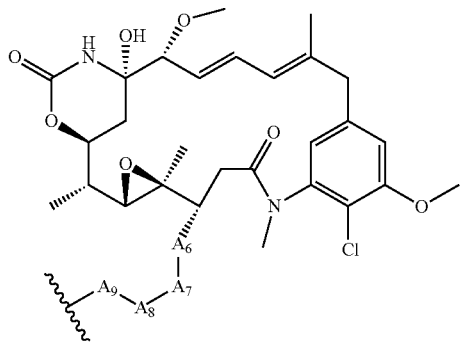

wherein $A_6$, $A_7$, $A_8$, $A_9$ are each independently absent, an amino acid, N-alkyl amino acid, a peptide having 2-20 amino acids, an alkyl, an alkenyl, an alkynyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—(CH$_x$)$_{p1}$—, —C(=O)—O—(CH$_x$)$_{p1}$—, —(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—NH—, —C(=S)—S—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, —C(=O)—N(R$_4$)—C(=O)—, —O—C(=O)—NR$_4$, further wherein alkyl, alkynyl, alkenyl, cycloalkyl, aryl, heteroaryl, and heterocyclyl are optionally substituted; and $R_4$, $R_5$, $R_6$ and $R_8$ are each independently H, or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In some embodiments, D is DM1 or DM4.
In some embodiments, D is:

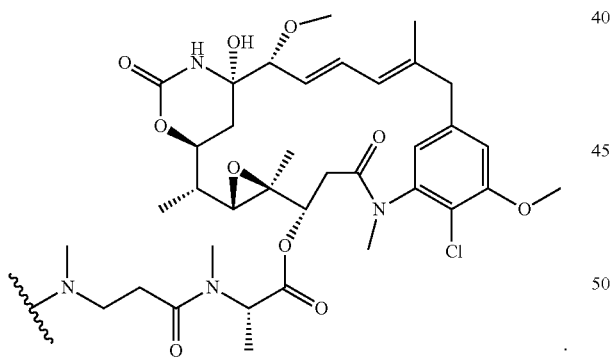

In some embodiments, D is:

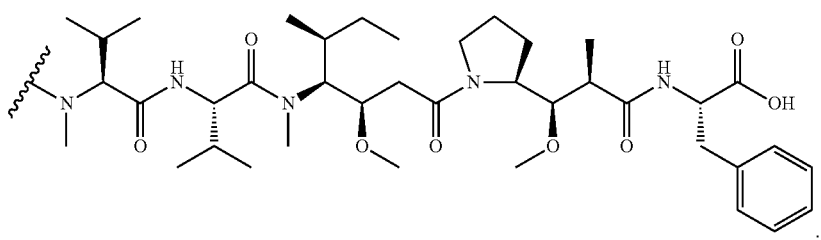 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

In some embodiments, the moiety of Formula (A) is:

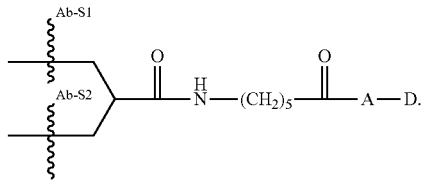

In some embodiments, the moiety of Formula (A) is:

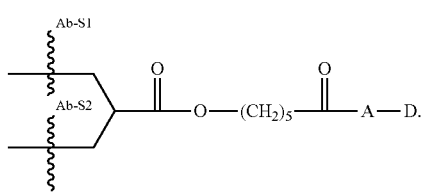

In some embodiments, the moiety of Formula (A) is:

wherein $R^N$ and $R^M$ are, independently, a hydrogen atom or $C_{1-6}$ alkyl.

In some embodiments, the moiety of Formula (A) is:
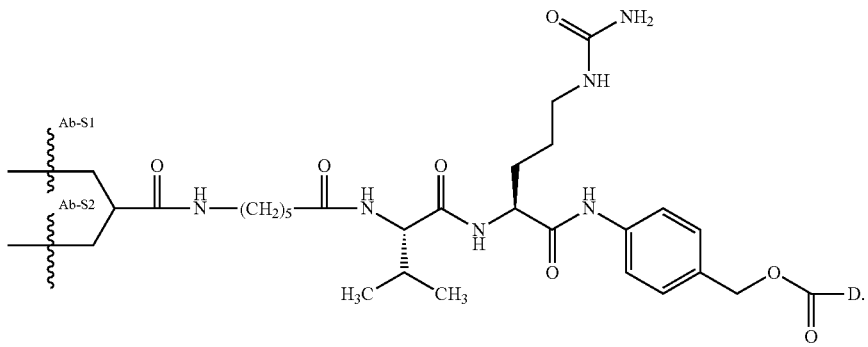
In some embodiments, the moiety of Formula (A) is:
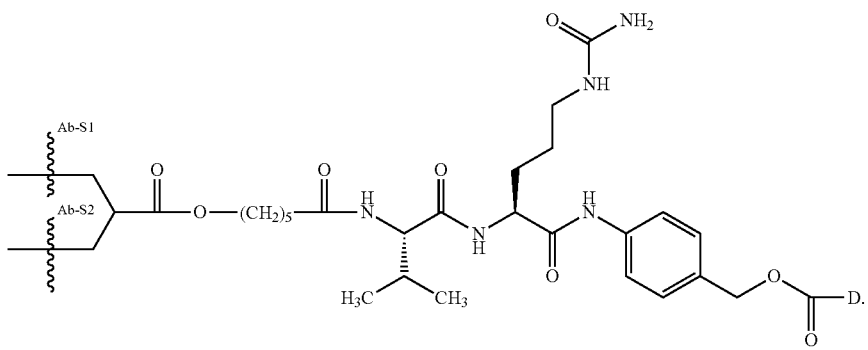
In some embodiments, the moiety of Formula (A) is:
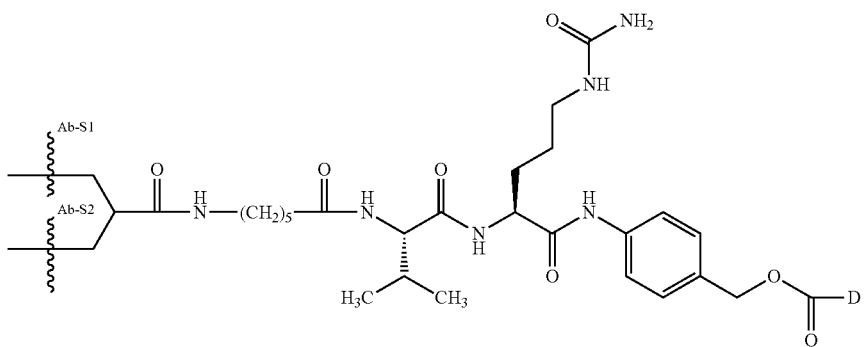
wherein D is a maytansinoid.
In some embodiments, the moiety of Formula (A) is:
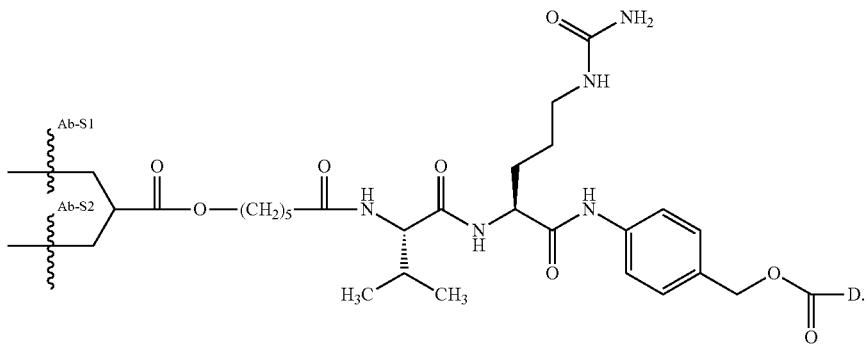
wherein D is a maytansinoid.

In some embodiments, the moiety of Formula (A) is:

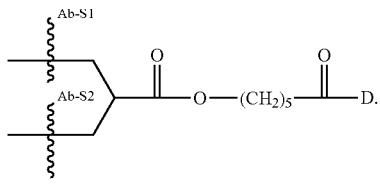

In some embodiments, the moiety of Formula (A) is:

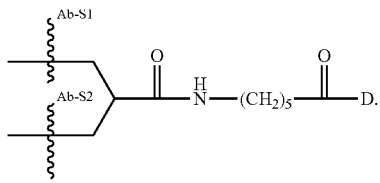

In some embodiments, the moiety of Formula (A) is:

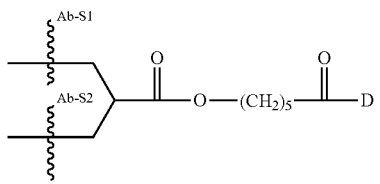

wherein D is an auristatin.

In some embodiments, the moiety of Formula (A) is:

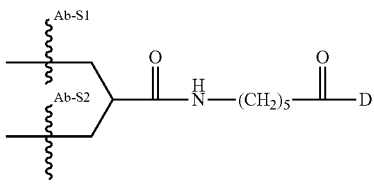

wherein D is an auristatin.

In some embodiments, the antibody or antigen binding fragment thereof further comprises a moiety of Formula (B1) or (B2):

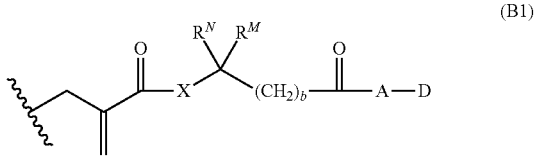

(B1)

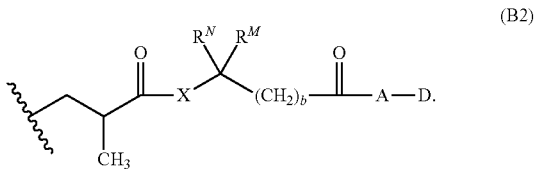

(B2)

In some embodiments, moiety of Formula (A) is:

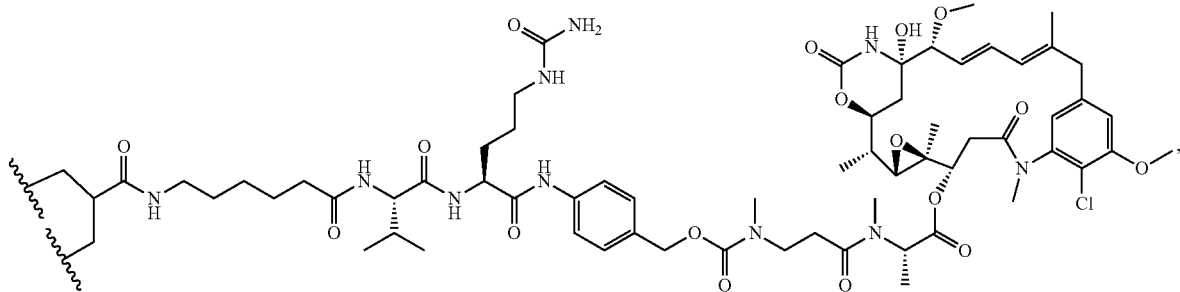

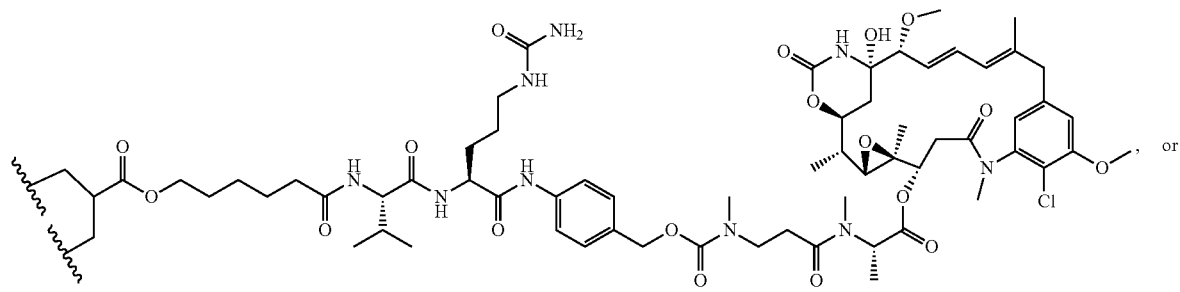

or

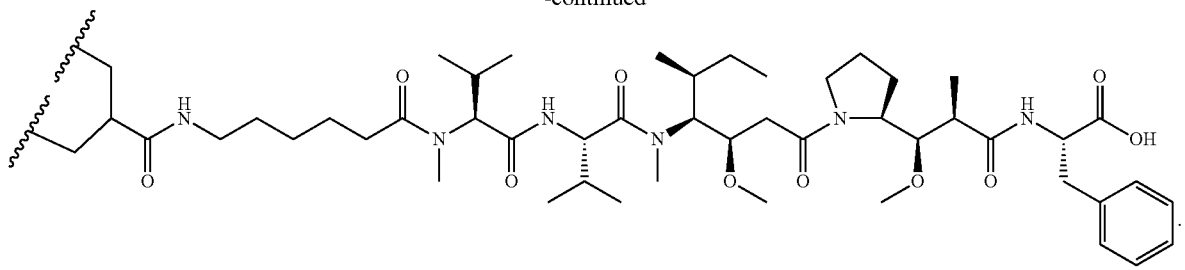

III. METHODS OF SYNTHESIZING CONJUGATES

A. Conjugation Methods

Figure 11:
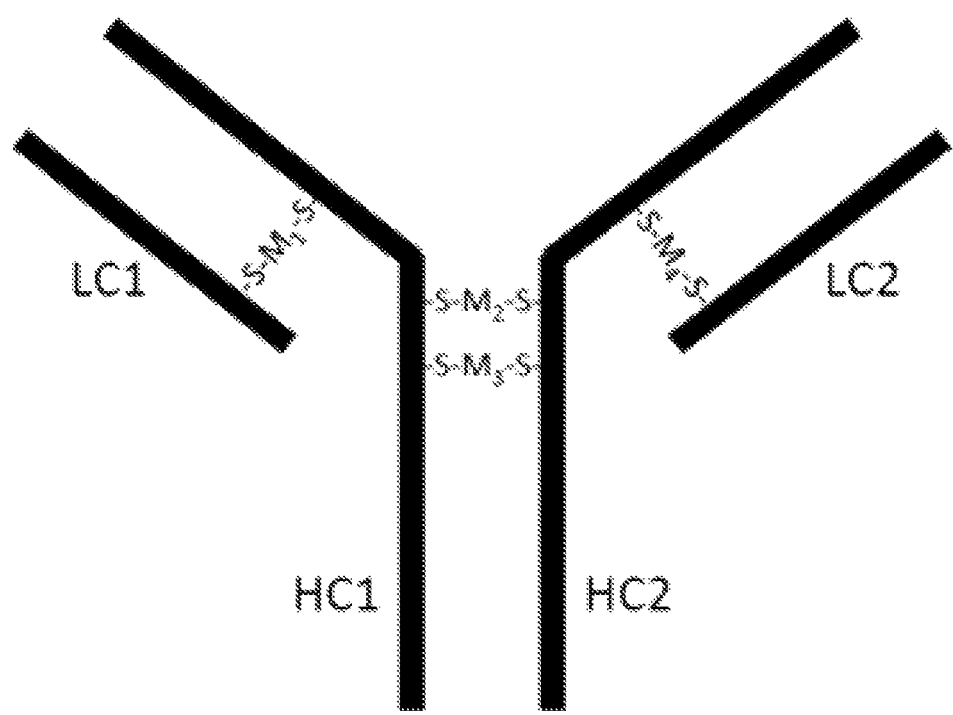
FIG. 11 provides a multimeric immunoglobulin conjugate.

The disclosure provides a method for preparing a multimeric immunoglobulin conjugate having the structure as set forth FIG. 11 wherein one or more $M_1$, $M_2$, $M_3$, and/or $M_4$ are each independently absent (i.e., the adjacent S atoms are directly connected to one another via a disulfide bond), or have the structure represented by formula (II)

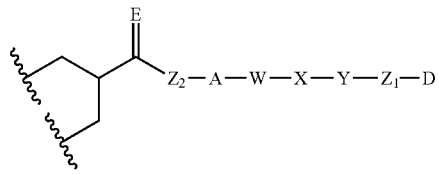

formula (II)

wherein
LC1 is a first antibody light chain,
LC2 is a second antibody light chain,
HC1 is a first antibody heavy chain, and
HC2 is a second antibody heavy chain;
  wherein LC1, LC2, HC1 and/or HC2 comprise at least one antigen-binding domain;
E is O, S, $NR_4$, or $CR_5R_6$;
D is a biologically active molecule;
$Z_1$ and $Z_2$ are each independently absent or a spacer;
A is absent, a natural or non-natural amino acid, or a peptide comprising 2-20 amino acids;
W is absent, —O—, —S—, —$CR_5R_6$—, or —$NR_4$—;
X is absent, aryl, heteroaryl, cycloalkyl, heterocyclyl,
  wherein aryl, heteroaryl, cycloalkyl, and heterocyclyl are optionally substituted;
Y is absent,

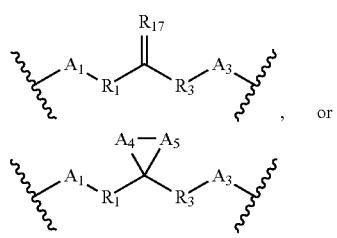

, or wherein $A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —(($CH_2)_{p2}$—O—$)_{p3}$—, —C(=S)—, —C(=S)—S—, —S—C(=S)—, —C(=S)—NH—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, or —O—C(=O)—$NR_4$—,
  wherein alkyl, alkynyl, alkenyl, cycloalkyl, aryl, heteroaryl, and heterocyclyl are optionally substituted;
$A_4$ and A5 are each independently —O—, —S—, —$NR_{18}$—, or —$CR_5R_6$—;
$R_{17}$ is O, S, $NR_{18}$, or $CR_5R_6$;
$R_{18}$ is H, alkyl, alkynyl, alkenyl, cycloalkyl, aryl, heteroaryl, heterocyclyl, or acyl,
  wherein alkyl, alkynyl, alkenyl, cycloalkyl, aryl, heteroaryl, heterocyclyl, and acyl are optionally substituted;
$R_4$, $R_5$, $R_6$ and $R_8$ are each independently H or a substituted or unsubstituted: alkyl, alkenyl, alkynyl, aryl, heteroaryl, or heterocyclyl;
p1, p2 and p3 are each independently 0, or an integer from 1 to 100;
x is 0, 1 or 2;
the method comprising the steps of
(a) reducing one or more disulfide bond between cysteine residues present in a multimeric immunoglobulin forming two sulfhydryl groups; and
(b) conjugating a reagent that forms a covalent bond with the sulfhydryl groups derived from step (a) wherein the reagent is represented by formula (III):

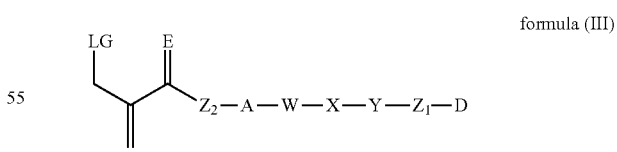

formula (III)

further wherein
LG is a leaving group;
E is O, S, $NR_4$, or $CR_5R_6$;
$Z_t$ and $Z_2$ are each independently absent or a spacer;
D is absent or a biologically active molecule;
A is absent, a natural or non-natural amino acid, or a peptide comprising 2-20 amino acids;
W is absent, —O—, —S—, —$CR_5R_6$—, or —$NR_4$—;
X is absent, aryl, heteroaryl, cycloalkyl, heterocyclyl, wherein aryl, heteroaryl, cycloalkyl, and heterocyclyl are optionally substituted; and
Y is absent,

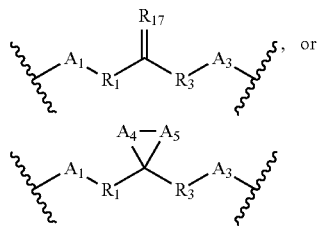

, or wherein $A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —$((CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —$N(R_4)C(=O)$—$N(R_8)$—, —$N(R_4)$—C(=O)O—, —$N(R_4)$—C(=O)—, —C(=O)—$N(R_4)$—, —C(=O)—$N(R_4)$—C(=O)—, or —OC(=O)—$NR_4$—,
  wherein alkyl, alkynyl, alkenyl, cycloalkyl, aryl, heteroaryl, and heterocyclyl are optionally substituted;
$A_4$ and $A_5$ are each independently —O—, —S—, —$NR_{18}$—, or —$CR_5R_6$—;
$R_{17}$ is O, S, $NR_{18}$, or $CR_5R_6$;
$R_{18}$ is H, alkyl, alkynyl, alkenyl, cycloalkyl, aryl, heteroaryl, heterocyclyl, or acyl,
  wherein alkyl, alkynyl, alkenyl, cycloalkyl, aryl, heteroaryl, heterocyclyl, and acyl are optionally substituted;
$R_4$, $R_5$, $R_6$ and $R_8$ are each independently H, or a substituted or unsubstituted: alkyl, alkenyl, alkynyl, aryl, heteroaryl, or heterocyclyl;
p1, p2 and p3 are each independently 0, or an integer from 1 to 100; and
x is 0, 1 or 2.

In an embodiment, the method for preparing a multimeric immunoglobulin conjugate further comprises purifying the product obtained in step (b) by chromatography, dialysis, ultra filtration, and/or tangential flow filtration.

In an embodiment, the disclosure provides a method for preparing a multimeric immunoglobulin conjugate, wherein $Z_2$ is represented by the following structural formula:

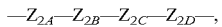

—$Z_{2A}$—$Z_{2B}$—$Z_{2C}$—$Z_{2D}$—, wherein:
$Z_{2A}$, $Z_{2B}$, $Z_{2C}$ and $Z_{2D}$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —$((CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, —O—C(=O)—$N(R_4)$, —O—C(=S)—$N(R_4)$—, or —C(=S)—$N(R_4)$—,
  wherein alkyl, alkynyl, alkenyl, cycloalkyl, aryl, heteroaryl, and heterocyclyl are optionally substituted and $R_4$, $R_5$, $R_6$ and $R_8$ are each independently H, or a substituted or unsubstituted: alkyl, alkenyl, alkynyl, aryl, heteroaryl, or heterocyclyl;
$Z_1$ is represented by the following structural formula:

—$Z_{1A}$—$Z_{1B}$—$Z_{1C}$—$Z_{1D}$—, 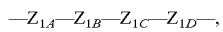

wherein:
$Z_{1A}$, $Z_{1B}$, $Z_{1C}$ and $Z_{1D}$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —$((CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, C(=O)—$N(R_4)$—C(=O)—, —O—C(=O)—$N(R_4)$, —O—C(=S)—$N(R_4)$—, or —C(=S)—$N(R_4)$—,
  wherein alkyl, alkynyl, alkenyl, cycloalkyl, aryl, heteroaryl, and heterocyclyl are optionally substituted and $R_4$, $R_5$, $R_6$ and $R_8$ are each independently H or a substituted or unsubstituted: alkyl, alkenyl, alkynyl, aryl, heteroaryl, or heterocyclyl;
p1, p2 and p3 are each independently 0, or an integer from 1 to 100; and
x is 0, 1 or 2.

In a further embodiment, the disclosure provides the method for preparing a multimeric immunoglobulin conjugate wherein the leaving group in the reagent represented by structural formula (III) is a halogen, tosyl, mesyl, OAc, OMe, triflate, nitrate, thiolate, phosphate, carboxylate, or phenoxide. In a further embodiment, the leaving group is bromo.

In an embodiment, the disclosure provides the method for preparing a multimeric immunoglobulin conjugate wherein formula (II) is represented by the following structure (II)(b):

(II)(b)

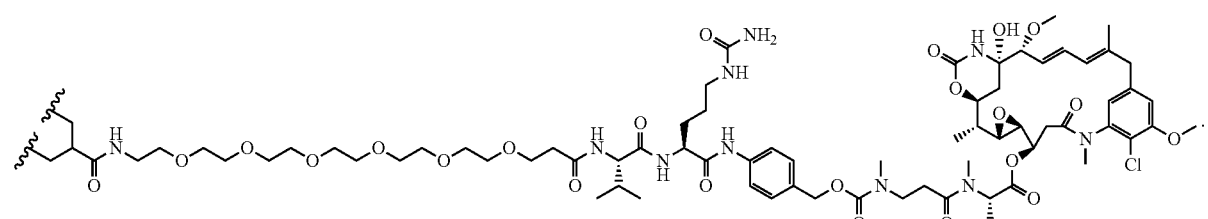

In a further embodiment, the disclosure provides the method for preparing a multimeric immunoglobulin conjugate wherein formula (III) is represented by the following structure (III)(b):

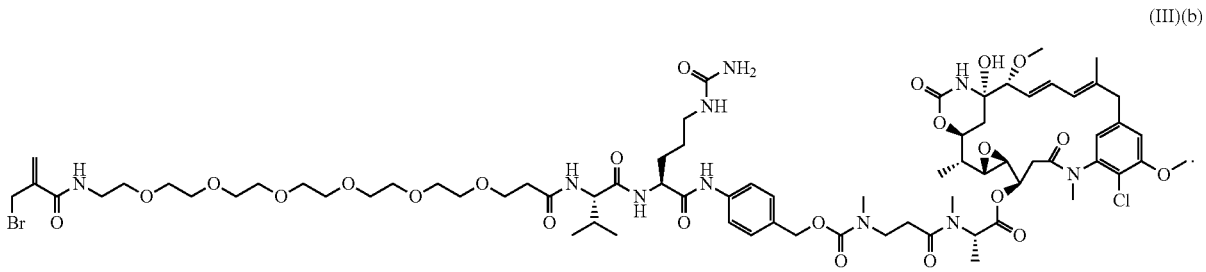 [SMILES: C=C(CBr)C(=O)NCCOCCOCCOCCOCCOCCOCCC(=O)N[C@H](C(=O)N[C@@H](CCCNC(N)=O)C(=O)Nc1ccc(COC(=O)N(C)CCC(=O)N(C)[C@@H](C)C(=O)O[C@@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@H]32)cc1)C(C)C]

(III)(b)

B. Linker-Payload Reagents

The disclosure also relates to a reagent represented by the following structural formula (III):

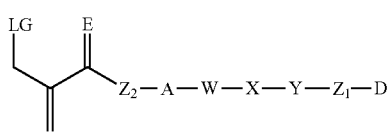

(III)

wherein:
LG is a leaving group;
E is O, S, NR$_4$, or CR$_5$R$_6$;
Z$_1$ and Z$_2$ are each independently absent or a spacer;
D is absent or a biologically active molecule;
A is absent, a natural or non-natural amino acid, or a peptide comprising 2-20 amino acids;
W is absent, —O—, —S—, —CR$_5$R$_6$—, or —NR$_4$—;
X is absent, aryl, heteroaryl, cycloalkyl, or heterocyclyl, wherein aryl, heteroaryl, cycloalkyl, and heterocyclyl are optionally substituted; and
Y is absent,

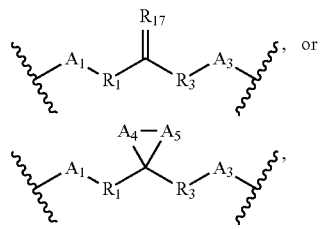

wherein
A$_1$, A$_3$, R$_1$ and R$_3$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(=O)—, —O—C(=O)—, —C(=O)—O—, —O—C(=O)—O—, —C(=O)—(CH$_x$)$_{p1}$—, —C(=O)—O—(CH$_x$)$_{p1}$—, —(CH$_x$)$_{p1}$—C(=O)—, —(CH$_x$)$_{p1}$—C(=O)—O—, —(O—CH$_2$)$_{p2}$—)$_{p3}$—, —((CH$_2$)$_{p2}$—O—)$_{p3}$—, —C(=S)—, —C(=S)—S—, —S—C(=S)—, —C(=S)—NH—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, —C(=O)—N(R$_4$)—C(=O)—, or —O—C(=O)—NR$_4$—, wherein alkyl, alkynyl, alkenyl, cycloalkyl, aryl, heteroaryl, and heterocyclyl are optionally substituted;
A$_4$ and A$_5$ are each independently —O—, —S—, —NR$_{18}$—, or —CR$_5$R$_6$—;
R$_{17}$ is O, S, NR$_{18}$, or CR$_5$R$_6$;
R$_{18}$ is H, alkyl, alkynyl, alkenyl, cycloalkyl, aryl, heteroaryl, heterocyclyl, or acyl,
wherein alkyl, alkynyl, alkenyl, cycloalkyl, aryl, heteroaryl, heterocyclyl, and acyl are optionally substituted;
R$_4$, R$_5$, R$_6$ and R$_8$ are each independently H, or a substituted or unsubstituted: alkyl, alkenyl, alkynyl, aryl, heteroaryl, or heterocyclyl;
p1, p2 and p3 are each independently 0, or an integer from 1 to 100; and
x is 0, 1 or 2.

In an embodiment, the disclosure provides a reagent represented by the structural formula (III), wherein Z$_2$ is represented by the following structural formula:

—Z$_{2A}$—Z$_{2B}$—Z$_{2C}$—Z$_{2D}$—, wherein:
Z$_{2A}$, Z$_{2B}$, Z$_{2C}$ and Z$_{2D}$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(=O)—, —O—C (=O)—, —C(=O)—O—, —O—C(=O))—O—, —C(=O)—(CH$_x$)$_{p1}$—, —C(=O)—O—(CH$_x$)$_{p1}$—, —(CH$_x$)$_{p1}$—C(=O)—, —(CH$_x$)$_{p1}$—C(=O)—O—, —(O—(CH$_2$)$_{p2}$—)$_{p2}$—, —((CH$_2$)$_{p2}$—O—)$_{p3}$—, —C(=S)—, —C(=S)—S—, —C(=S)—NH—, —S—C (=S)—, —S—C(=S)—S—, —S—, —SO—, —SO$_2$—, —NR$_4$—, —N(R$_4$)—C(=O)—N(R$_8$)—, —N(R$_4$)—C (=O)O—, —N(R$_4$)—C(=O)—, —C(=O)—N(R$_4$)—, —C(=O)—N(R$_4$)—C(=O)—, —O—C(=O)—N(R$_4$), —O—C(=S)—N(R$_4$)—, or —C(=S)—N(R$_4$)—,
wherein alkyl, alkynyl, alkenyl, cycloalkyl, aryl, heteroaryl, and heterocyclyl are optionally substituted and R$_4$, R$_5$, R$_6$ and R$_8$ are each independently H, or a substituted or unsubstituted: alkyl, alkenyl, alkynyl, aryl, heteroaryl, or heterocyclyl;
and Z$_1$ is represented by the following structural formula:

—Z$_{1A}$—Z$_{1B}$—Z$_{1C}$—Z$_{1D}$—, wherein:
Z$_{1A}$, Z$_{1B}$, Z$_{1C}$ and Z$_{1D}$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(=O)—, —O—C (=O)—, —C(=O)—O—, —O—C(=O)—O—, —C(=O)—(CH$_x$)$_{p1}$—, —C(=O)—O—(CH$_x$)$_{p1}$—, —(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—S—, —C(=S)—NH—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, C(=O)—N(R$_4$)—C(=O)—, —O—C(=O)—N(R$_4$), —O—C(=S)—N(R$_4$)—, or —C(=S)—N(R$_4$)—, wherein alkyl, alkynyl, alkenyl, cycloalkyl, aryl, heteroaryl, and heterocyclyl are optionally substituted and R$_4$, R$_5$, R$_6$ and R$_8$ are each independently H, or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In a further embodiment, the disclosure provides a reagent represented by structural formula (III), wherein the leaving group is a halogen, tosyl, mesyl, OAc, OMe, triflate, nitrate, thiolate, phosphate, carboxylate, phenoxide. In a further embodiment, the disclosure provides a reagent represented by structural formula (III), wherein the leaving group is bromo.

In an embodiment, the disclosure provides a reagent of formula (III) represented by the following structure (III)(b):

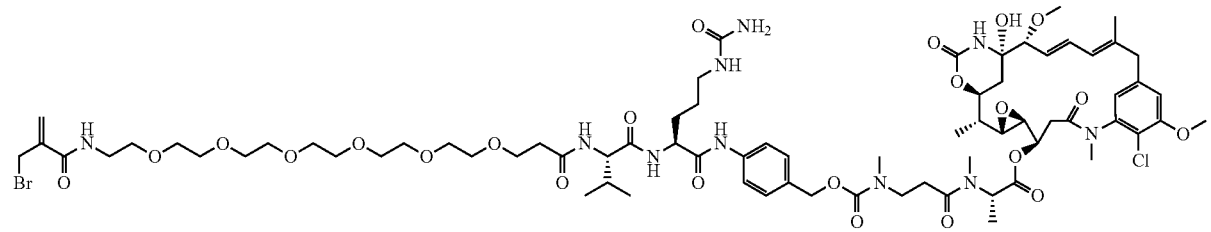 [SMILES: C=C(CBr)C(=O)NCCOCCOCCOCCOCCOCCOCCC(=O)N[C@H](C(=O)N[C@@H](CCCNC(N)=O)C(=O)Nc1ccc(COC(=O)N(C)CCC(=O)N(C)[C@@H](C)C(=O)O[C@@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@H]32)cc1)C(C)C]

In another embodiment, the compound has the formula (aa) or (bb):

M-Z$_2$-A-W-X-Y-Z$_1$-D    (aa)

M-A-D    (bb)

wherein M is:

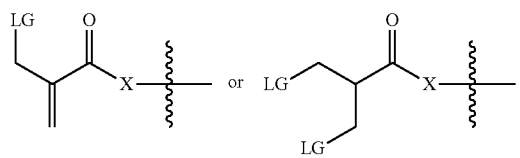

wherein X is —O— or —NH— and LG is a leaving group, e.g., Br;

and Z$_2$, A, W, X, Y, Z$_1$, and D are as defined herein.

In some embodiments, the
(i) M-Z2-A- of formula (aa) or
(ii) M-A- of formula (bb) is:

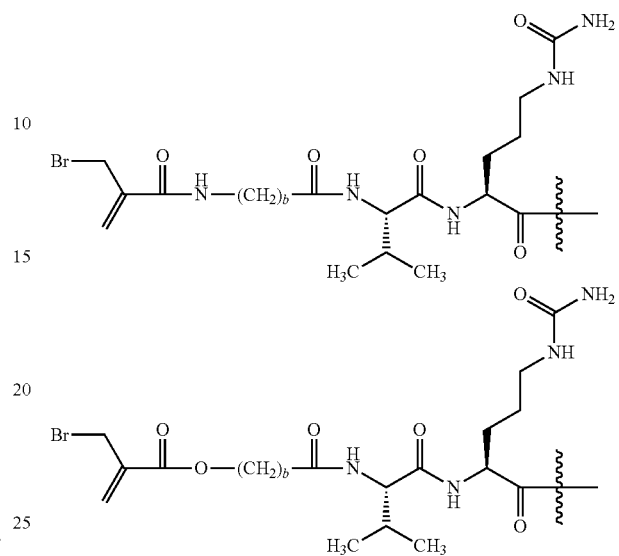

-continued

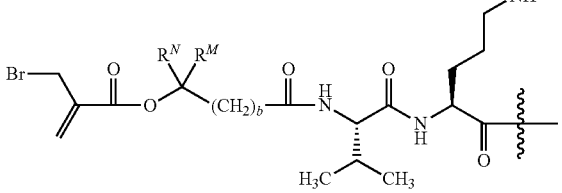

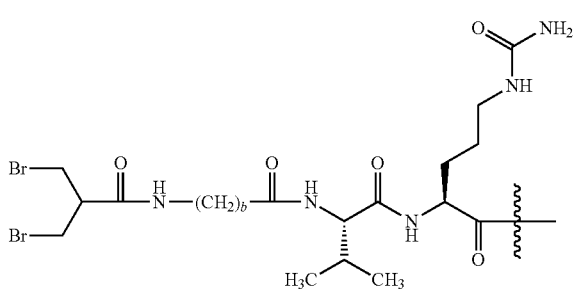

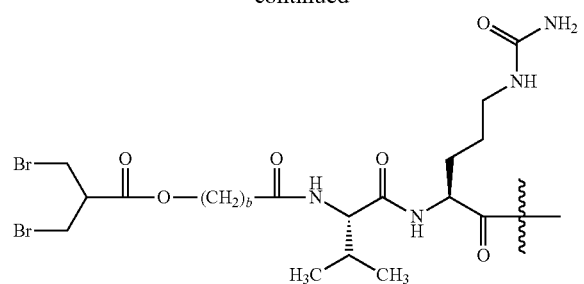

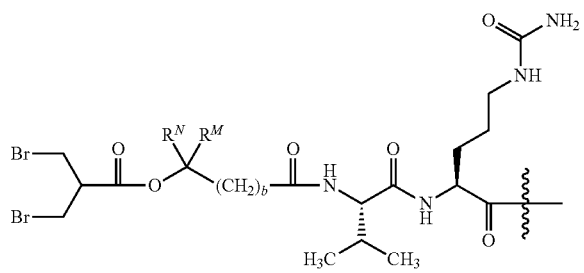

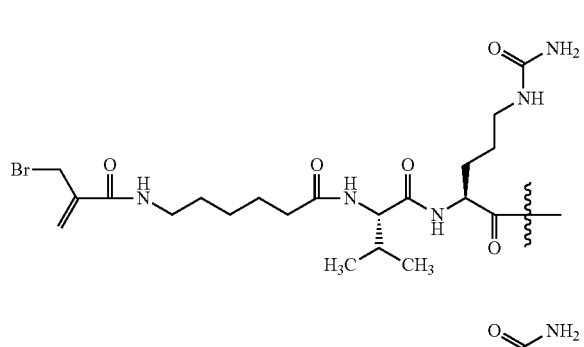

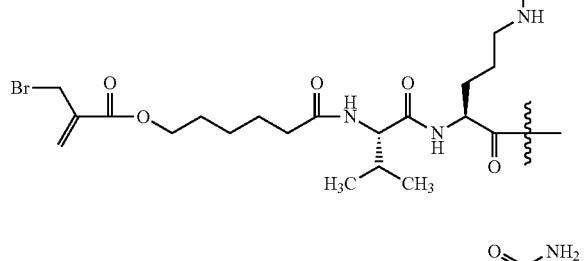

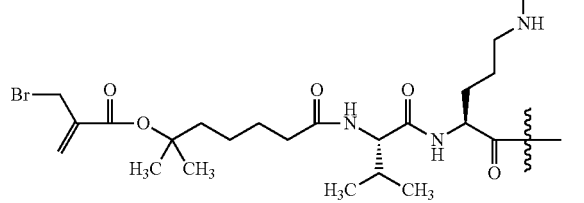

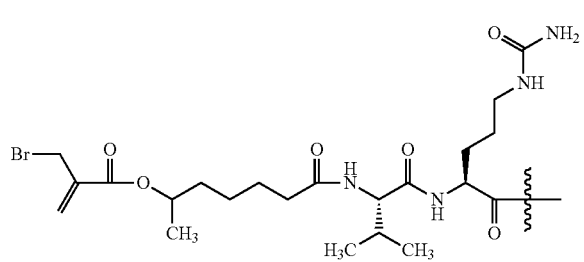

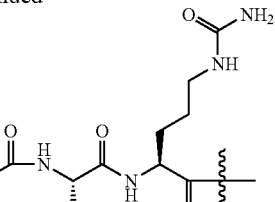

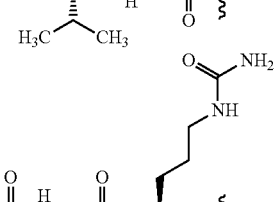

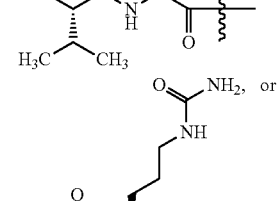

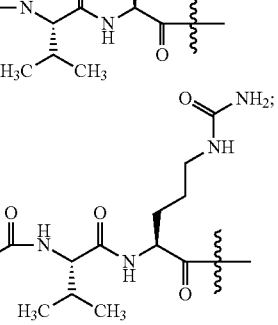

wherein b is an integer from 2 to 8, $R^N$ is a hydrogen atom or alkyl, and $R^M$ is alkyl.

Provided herein are also linker-payload compounds of Formula (L1):

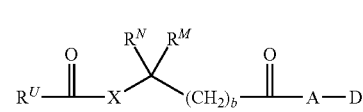

(L1)

wherein:
$R^U$ is

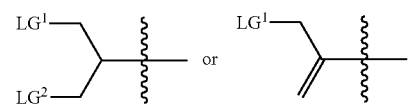

wherein $LG^1$ and $LG^2$, independently at each occurrence, is a leaving group;
X is —N($R^A$)— or —O—;
wherein $R^A$ is a hydrogen atom or alkyl;
$R^N$ and $R^M$ are each, independently, a hydrogen atom or alkyl;
A is absent, i.e., a bond, or a spacer comprising a peptide, wherein the peptide comprises 2-20 amino acids;
D is a biologically active molecule; and
b is an integer from 2 to 8.

In some embodiments, the leaving group is a halogen, tosyl, mesyl, OAc, OMe, triflate, nitrate, thiolate, phosphate, carboxylate, or phenoxide.

In some embodiments, the leaving group is —Br.

In some embodiments, X is —N(R$^A$)—. In certain embodiments, R$^A$ is a hydrogen atom.

In some embodiments, X is —O—.

In some embodiments, R$^N$ and R$^M$ are both hydrogen atoms. In some embodiments, R$^N$ is a hydrogen atom and R$^M$ is alkyl. In some embodiments, R$^N$ and R$^M$ are both alkyl.

In some embodiments, X is —O— and R$^N$ and R$^M$ are both hydrogen atoms. In some embodiments, X is —O—, R$^N$ is a hydrogen atom, and R$^M$ is alkyl. In some embodiments, X is —O— and R$^N$ and R$^M$ are both alkyl. In some embodiments, X is —O—, R$^N$ is a hydrogen atom, and R$^M$ is methyl. In some embodiments, X is —O— and R$^N$ and R$^M$ are both methyl.

In some embodiments, b is an integer from 3-6. In some embodiments, b is 4. In some embodiments, R$^N$ and R$^M$ are both hydrogen atoms and b is 4.

In some embodiments, X is —O—, R$^N$ and R$^M$ are both hydrogen atoms, and b is 4. In some embodiments, X is —O—, R$^N$ and R$^M$ are both alkyl, and b is 4. In some embodiments, X is —O—, R$^N$ and R$^M$ are both methyl, and b is 4. In some embodiments, X is —O—, R$^N$ is alkyl, R$^M$ is a hydrogen atom, and b is 4.

In some embodiments, X is —N(H)—, R$^N$ and R$^M$ are both hydrogen atoms, and b is 4.

In some embodiments, A is a spacer comprising a dipeptide. In some embodiments, the dipeptide is valine-citrulline. In some embodiments, A is:

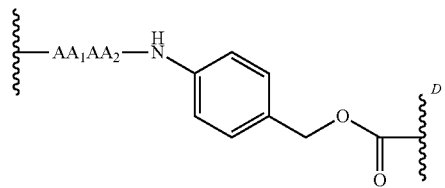

wherein

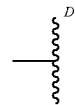

is the bond to D.

In some embodiments, A is:

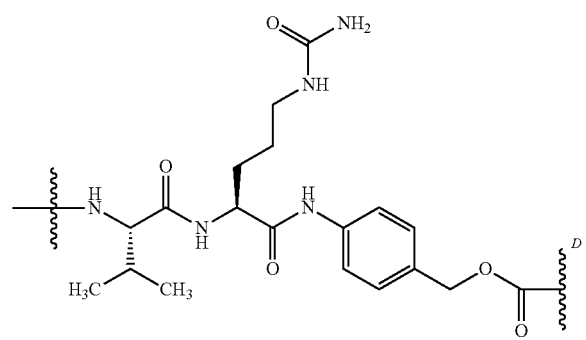

wherein

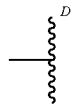

is the bond to D.

In some embodiments, A is absent.

In some embodiments, D is an auristatin or maytansinoid.

In some embodiments, D is an auristatin, wherein the auristatin is MMAE, MMAD, or MMAF.

In some embodiments, D is MMAF.

In some embodiments, D is a maytansinoid

In some embodiments, A is spacer comprising a peptide comprising 2-20 amino acids and D is a maytansinoid.

In some embodiments, A is absent and D is an auristatin.

In some embodiments, A is represented by formula (I)(a) as biologically active macrolide:

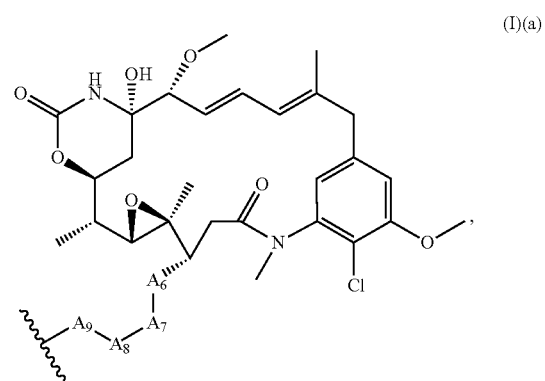

(I)(a)

wherein $A_6$, $A_7$, $A_8$, $A_9$ are each independently absent, an amino acid, N-alkyl amino acid, a peptide having 2-20 amino acids, an alkyl, an alkenyl, an alkynyl, a cycloalkyl, an aryl, a heteroaryl, a heterocyclyl, —CR$_5$R$_6$—, —O—, —C(=O)—, —O—C(=O)—, —C(=O)—O—, —O—C(=O)—O—, —C(=O)—(CH$_x$)$_{p1}$—, —C(=O)—O—(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—NH—, —C(=S)—S—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, —C(=O)—N(R$_4$)—C(=O)—, —O—C(=O)—NR$_4$, further wherein alkyl, alkynyl, alkenyl, cycloalkyl, aryl, heteroaryl, and heterocyclyl are optionally substituted; and R$_4$, R$_5$, R$_6$ and R$_8$ are each independently H, or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In some embodiments, D is DM1 or DM4.

In some embodiments, D is:
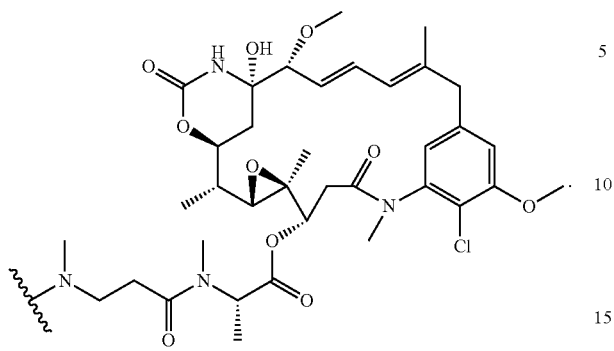
In some embodiments, D is:
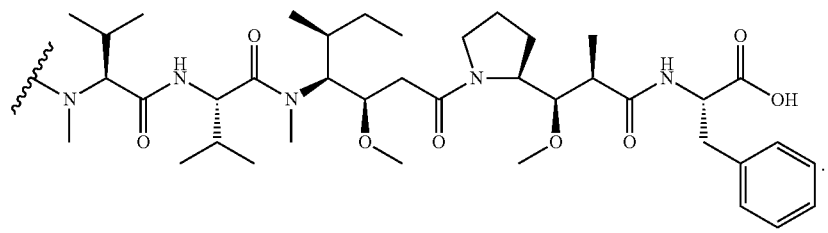 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]
In some embodiments, the compound of Formula (L1) is:
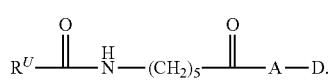
In some embodiments, the compound of Formula (L1) is:
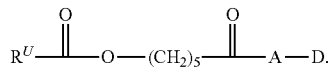
In some embodiments, the compound of Formula (L1) is:
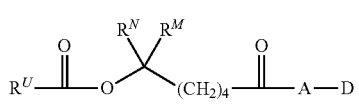
wherein $R^N$ and $R^M$ are, independently, a hydrogen atom or $C_{1-6}$ alkyl.
In some embodiments, compound of Formula (L1) is:
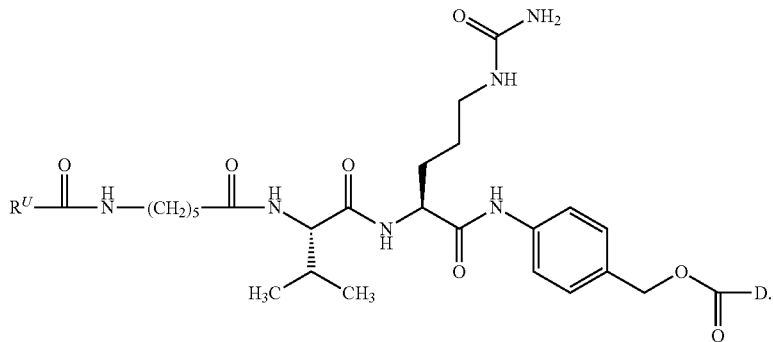

In some embodiments, the compound of Formula (L1) is:
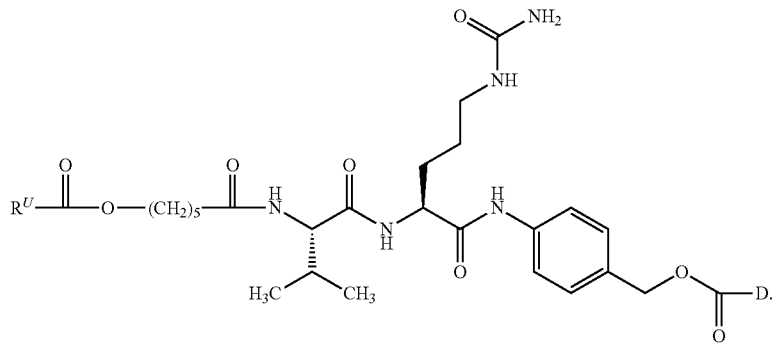
In some embodiments, the compound of Formula (L1) is:
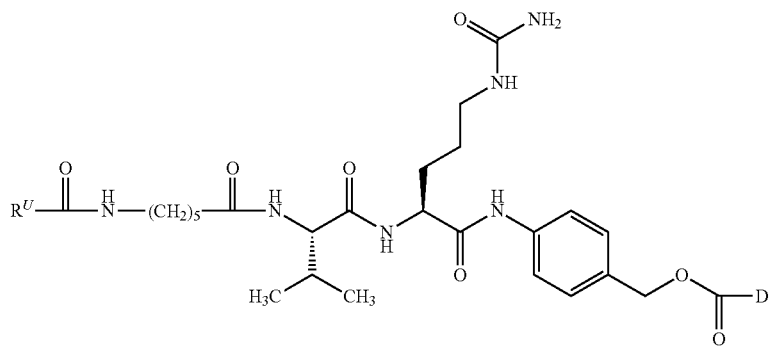
wherein D is a maytansinoid.
In some embodiments, the compound of Formula (L1) is:
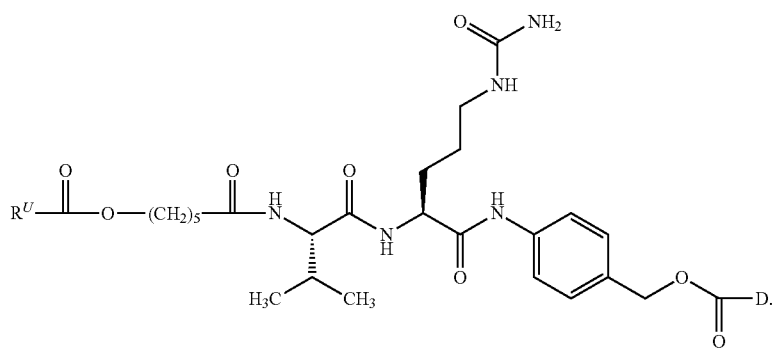
wherein D is a maytansinoid.
In some embodiments, the compound of Formula (L1) is:
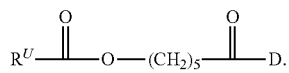
In some embodiments, the compound of Formula (L1) is:
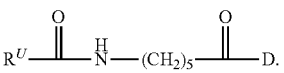

55
In some embodiments, the compound of Formula (L1) is:
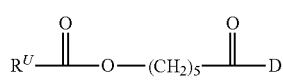
wherein D is an auristatin.
56
In some embodiments, the compound of Formula (L1) is:
wherein D is an auristatin.
In some embodiments, compound of Formula (L1) is:
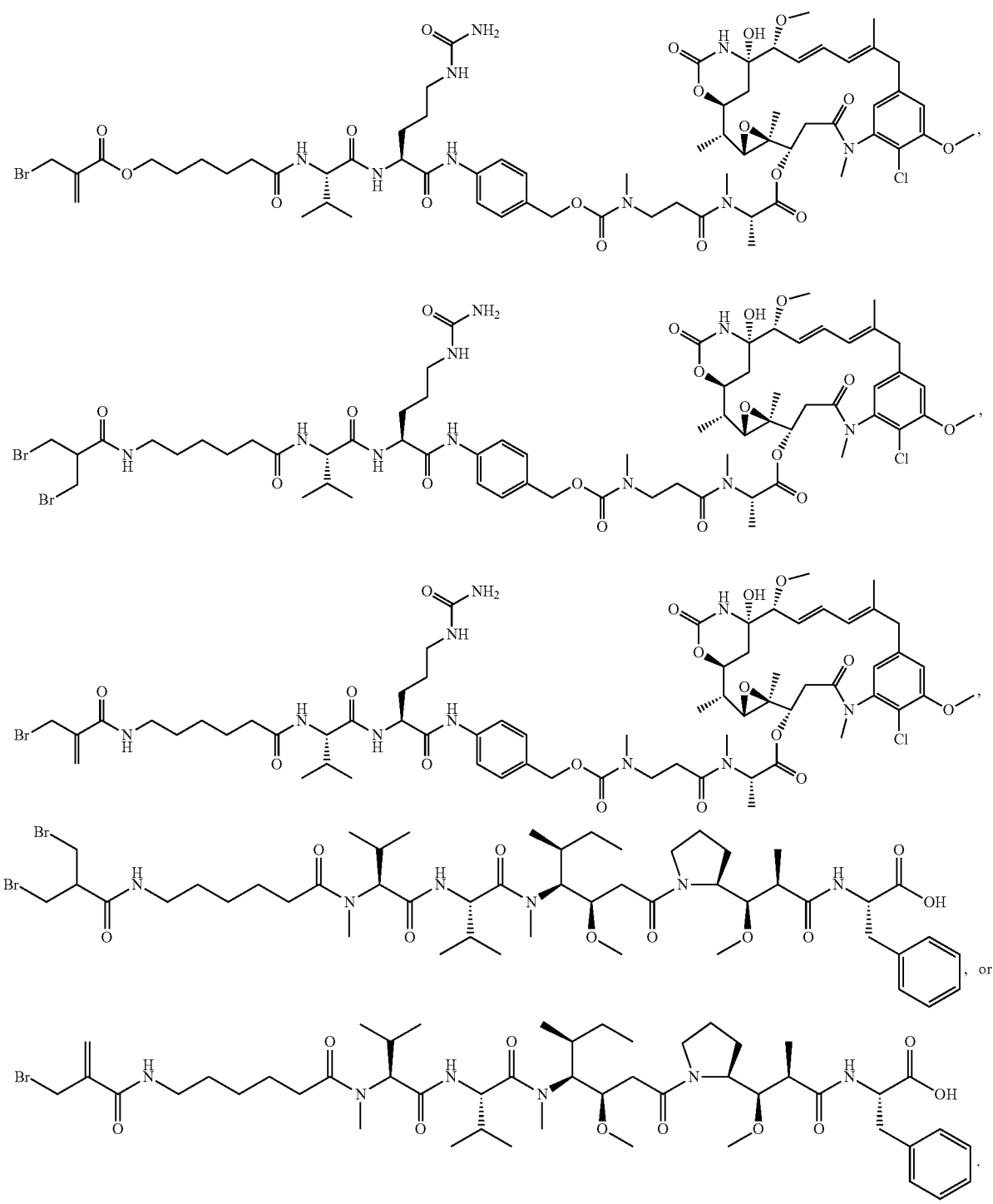

Linker payloads can be synthesized via carboxylic acid coupling conditions, e.g., as depicted below:

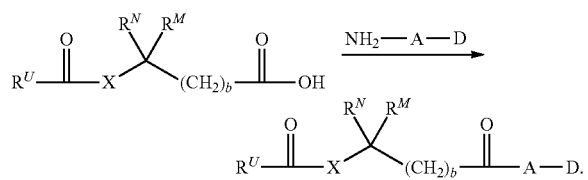

The carboxylic acid can be synthesized from acid halides, e.g., as depicted below:

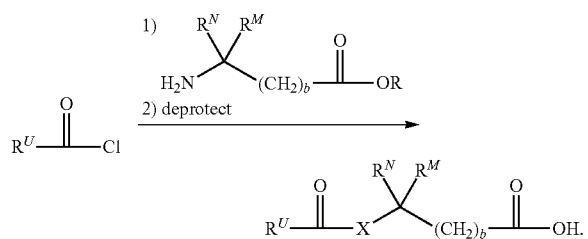

IV. PHARMACEUTICAL COMPOSITIONS AND METHODS OF USE

Embodiments here include compositions comprising the conjugates described herein, e.g., compounds of formula (I), FIG. 1), or formula (III) as well as mixtures thereof. In some aspects the compound is further represented by a compound of formula (I)(b), formula (II)(b), or formula (III)(b).

Compositions may be pharmaceutical compositions that further include one or more pharmaceutically acceptable carriers, diluents, and/or excipients. In some aspects the pharmaceutical composition is the pharmaceutically acceptable salt of the conjugates described herein, e.g., the compounds of formula (I), FIG. 1), and/or formula (III) or mixtures thereof.

Suitable pharmaceutical acceptable carriers, diluents and excipients are well known in the art and can be determined by one of ordinary skill in the art as the clinical situation warrants. Examples of suitable carriers, diluents and excipients include: buffers for maintenance of proper composition pH (e.g., citrate buffers, succinate buffers, acetate buffers, phosphate buffers, lactate buffers, oxalate buffers and the like), carrier proteins (e.g., human serum albumin), saline, polyols (e.g., trehalose, sucrose, xylitol, sorbitol, and the like), surfactants (e.g., polysorbate 20, polysorbate 80, polyoxalate, and the like), antimicrobials, and antioxidants.

If so desired, the pharmaceutical compositions herein may include a second or more therapeutic agent (e.g., an adjuvant to the formula (I), FIG. 1), and/or formula (III)). The second therapeutic agent can be included in the same composition as the compounds of, e.g., formula (I), FIG. 1), and/or formula (III), or can be administered separately from the compounds of, e.g., formula (I), FIG. 1), and/or formula (III) (by time, or type and location of administration).

One of skill in the art of biologically active molecules will understand that each of the compounds of, e.g., formula (I), FIG. 1), and/or formula (III) can be modified in such a manner that the resulting compound still retains specificity and/or activity similar to the starting compound. In this light, the biologically active molecule (D) of compounds of, e.g., formula (I), FIG. 1), and/or formula (III) can include any and all of the biologically active molecules' analogues and derivatives.

In one aspect, the disclosure provides the pharmaceutical composition comprising a therapeutically effective amount of a compound of, e.g., formula (I), FIG. 1), and/or formula (III), or a pharmaceutically acceptable salt thereof and one or more pharmaceutically acceptable carriers, diluents, or excipients.

In another aspect, the disclosure provides pharmaceutical composition comprising a therapeutically effective amount of a compound of, e.g., formula (I)(b), formula (II)(b), and/or formula (III)(b), or a pharmaceutically acceptable salt thereof and one or more pharmaceutically acceptable carriers, diluents, or excipients.

As described above, conjugate compounds of, e.g., formula (I), and/or FIG. 1), can be produced with various functional groups such that attachment of the multimeric immunoglobulin or the multimeric antigen-binding compound to the linker and thereby a biologically active molecule form a covalent conjugate. The multimeric immunoglobulin or the multimeric anti-binding compound specially targets the conjugate compound to the multimeric immunoglobulin or the multimeric anti-binding compound binding partner, typically a polypeptide or other like antigen. In an embodiment, the conjugate is designed to include a multimeric immunoglobulin or the multimeric anti-binding compound having a binding partner found on cells undergoing abnormal cell growth or cells involved in a proliferative disorder. In an embodiment, conjugate compounds of, e.g., formula (I), and/or FIG. 1) have been designed such that each compound's linker is catabolized inside the cell bound by the conjugate. As such, delivery of a biologically active molecule through the conjugate embodiments herein allows for delivery of biologically active molecules that would normally be too toxic to administer conventionally. The embodiments herein allow for highly selective and specific delivery of these conjugates to cells undergoing abnormal cell growth or cells involved in proliferative disorders (as compared to catabolism outside the cell, thereby releasing the biologically active compound into the blood or lymphatic system, for example).

As can be envisioned by one of skill in the art, the covalent conjugate compounds described herein can also be used to deliver any type of useful biologically active molecule and can be selectively targeted to any type of cell population, for example, the conjugate may be used to deliver anti-proliferative drugs to cells undergoing abnormal growth or anti-viral drugs to cells infected with a virus, as long as the selected multimeric immunoglobulin or the multimeric anti-binding compound recognizes a proper cell binding partner.

In this light, methods of use are provided for the conjugate compound embodiments described herein.

The pharmaceutical compositions described herein are useful in inhibiting, retarding and/or preventing abnormal cell growth or in the treatment of various proliferative disorders or disease states in mammals. In typical embodiments the mammal is a human (embodiments herein will be described in relation to humans). Other mammals include any mammal that can suffer from a detectable proliferative disorder, including primates, dogs, cats, horses, goats, sheep, cattle, camels, and the like. In addition, it is understood that the conjugate compounds of the pharmaceutical compositions are designed for selective targeting to the cells undergoing abnormal cell growth or for the treatment of the various proliferative disorders or disease states described herein.

As such, embodiments herein include methods of inhibiting abnormal cell growth or treatment of a proliferative disorder in a human comprising administering to the human a therapeutically effective amount of a pharmaceutical composition described herein.

Administration of a therapeutically effective amount of a pharmaceutical composition described herein may be effected in different ways, e.g., by intravenous, intraperitoneal, subcutaneous, intramuscular, topical, intradermal, intranasal, or intrabronchial administration. The pharmaceutical compositions herein may also be administered directly to an abnormal cell growth site (directly or indirectly contacting the abnormal cell growth) by, for example, biolistic delivery (biolistic delivery of the pharmaceutical compositions herein to a lung or brain tumor, for example). Dosage regiments for administration of the pharmaceutical compositions herein will be determined by the attending health care professional or other person of skill in the art as well as based on the particular clinical situation. As is well known in the pharmaceutical arts, dosages for any one human, i.e., patient, depends on a number of factors, including patient size, patient's body surface area, patient's age and general health, patient's sex, the time and route of administration, and presence of a second therapeutic agent. In some instances the conjugates described herein, e.g., compounds of formula (I), FIG. 1), and/or formula (III) may be present in amounts between 1 µg and 100 mg/kg body weight per dose (note that where continuous infusion is considered as an administration route, as little as 1 pg/kg body weight per minute may be considered). Pharmaceutical compositions can be administered one or more times a day and over a period of days, weeks, months, or years.

Treatment of proliferative disorder or disease, for example a tumor, includes methods of reducing a tumor size, causing necrosis or apoptosis in a tumor, killing a tumor, stopping a tumor from increasing in size and/or preventing invasiveness or metastasis of a tumor.

Examples of medical conditions that can be treated according to methods of inhibiting abnormal cell growth, or treating proliferative disorders include: malignancy of any type, e.g., cancer of the lung, colon, prostate, kidney, pancreas, liver, ovary, skin, lymphoma, leukemia and the like; autoimmune diseases, e.g., systemic lupus, rheumatoid arthritis, multiple sclerosis; viral infections, e.g., CMV infection, HIV infection, AIDS, Hepatitis, HPV infection; pain; mental disorders; and inflammatory diseases.

As noted above, pharmaceutical compositions described herein are also useful in the prevention or treatment of viral infections, pain, inflammatory diseases, autoimmune diseases, and the like in a mammal.

In one aspect, the disclosure provides a method of reducing, retarding or stopping an abnormal cell growth comprising contacting the abnormal cell with a conjugate described herein, e.g., a compound of formula (I), FIG. 1), and/or formula (III) in an amount sufficient to retard, reduce or stop the abnormal cell growth, and wherein the abnormal cell growth is retarded, reduced or stopped.

In one aspect, the disclosure provides a method of killing a cell, comprising contacting the cell with a conjugate described herein, e.g., a compound of formula (I), FIG. 1), and/or formula (III) in an amount sufficient to kill the cell, and wherein the cell is killed.

In one embodiment, the disclosure provides a method of killing a cell, comprising contacting the cell with a conjugate described herein, e.g., a compound of formula (I), FIG. 1), and/or formula (III) in an amount sufficient to kill the cell, and wherein the cell is killed and further wherein the cell is a tumor cell.

In one aspect, the disclosure provides a method of treatment of a medical disorder in an individual suffering from the medical disorder, comprising administering to the individual an effective amount of a composition comprising a conjugate described herein, e.g., a compound of formula (I), FIG. 1), and/or formula (III).

In one embodiment, the disclosure provides a method of treatment of a medical disorder in an individual suffering from the medical disorder comprising administering to the individual an effective amount of a composition comprising a conjugate described herein, e.g., a compound of formula (I), FIG. 1), and/or formula (III) and further comprising administering sequentially or consecutively an additional therapy.

In one embodiment, the disclosure provides methods, wherein additional therapy is radiation therapy, chemotherapy, surgery, or combinations thereof.

In one embodiment, the disclosure provides a method of treatment of a medical disorder in an individual suffering from the medical disorder comprising administering to the individual an effective amount of a composition comprising a conjugated described herein, e.g., a compound of formula (I), FIG. 1), and/or formula (III) and further comprising administering sequentially or consecutively an additional therapy and administering at least one additional therapeutic agent.

In an aspect, the medical disorder treated is selected from tumors, cancers, infectious diseases, neurodegenerative diseases, bone disorders, and cardiovascular diseases.

Finally, embodiments herein may include mixtures of the conjugates described herein, e.g., the compounds as represented by formula (I), FIG. 1), and/or formula (III).

While the disclosure has been particularly shown and described with reference to a number of embodiments, it would be understood by those skilled in the art that changes in the form and details may be made to the various embodiments disclosed herein without departing from the spirit and scope of the disclosure and that the various embodiments disclosed herein are not intended to act as limitations on the scope of the claims.

V. EXAMPLES

Experimental Details

The following examples are provided for illustrative purposes only and are not intended to limit the scope of the disclosure.

Proton NMR spectra were acquired on a Varian Inova 300 MHz or 500 MHz instrument, while mass spectra were collected on one of two Agilent LCMS instruments using electrospray ionization, either an 1100 series LC/MSD with a ion trap analyzer or a 1200 series LC/MSD with a single quadrupole analyzer. Conjugate mass spectra were acquired as detailed in the example. All starting materials were purchased commercially and used without purification, while solvents were purchased commercially and dried where necessary via methods well known in the art. The following is a list of the abbreviations used in the Examples, with their full chemical names in parentheses: Boc (N-tert-butoxycarbonyl), DCM (dichloromethane), DIEA (N,N-diisopropylethylamine), DMF (N,N-dimethylformamide), EtOAc (ethyl acetate), HATU (1-[Bis(dimethylamino)methylene]-1H-1,2,3-triazolo[4,5-b]pyridinium 3-oxid hexafluorophosphate), HCl (hydrochloric acid), HOAc (glacial acetic acid), HOAT (1-hydroxy-7-azabenzotriazole), HPLC (high-performance liquid chromatography), LCMS (tandem HPLC and mass spectrometry), MeCN (acetonitrile), MeMgI (methyl magnesium iodide), MMAF (monomethyl-auristatin F), NaHCO$_3$ (sodium bicarbonate), Na$_2$SO$_4$ (anhydrous sodium sulfate), NH$_4$Cl (ammonium chloride), t-BuOK (potassium tert-butoxide), TFA (trifluoroacetic acid), THF (tetrahydrofuran).

Example 1

The present Example illustrates the utility of conjugating a molecule to an antibody by bridging (i.e., rejoining) one or more disulfide bonds of the antibody with a linker compound of the present disclosure. In particular, a proof-of-concept linker molecule (i.e., 2-(bromo-methyl)acrylate (1) [Sigma Aldrich]), representative of the linker-drug molecules of the present disclosure, was conjugated to an antibody at cysteine residues on the antibody, and the resulting conjugate molecule was assessed for stability using SDS-PAGE under reducing conditions.

Conjugate Preparation and Characterization

Briefly, a test monoclonal antibody of Fc isotype IgG1 ("mAb1," 10 mg/ml) in 50 mM HEPES, 150 mM NaCl, pH 7.5, was reduced with 1 mM dithiothreitol (0.006 mg per mg of antibody) at 37° C. for 30 min. After gel filtration (G-25, pH 4.5 sodium acetate), the methyl 2-(bromo-methyl)acrylate (1, 1.2 equivalents/disulfide) in DMSO (10 mg/ml) was added to the reduced antibody, the mixture was adjusted to pH 7.0 with 1 M HEPES (pH 7.4), and allowed to react for 4 h. Immediately following the alkylation, the antibody was oxidized with 0.5 mM dehydroascorbic acid (dhAA) for 4 h. The conjugate was purified by size exclusion chromatography. Protein concentrations were determined by UV spectral analysis. Size-exclusion HPLC established that all conjugates were >95% monomeric. Conjugates were analyzed by reduced and non-reduced SDS-PAGE (FIG. 2).

Figure 2:
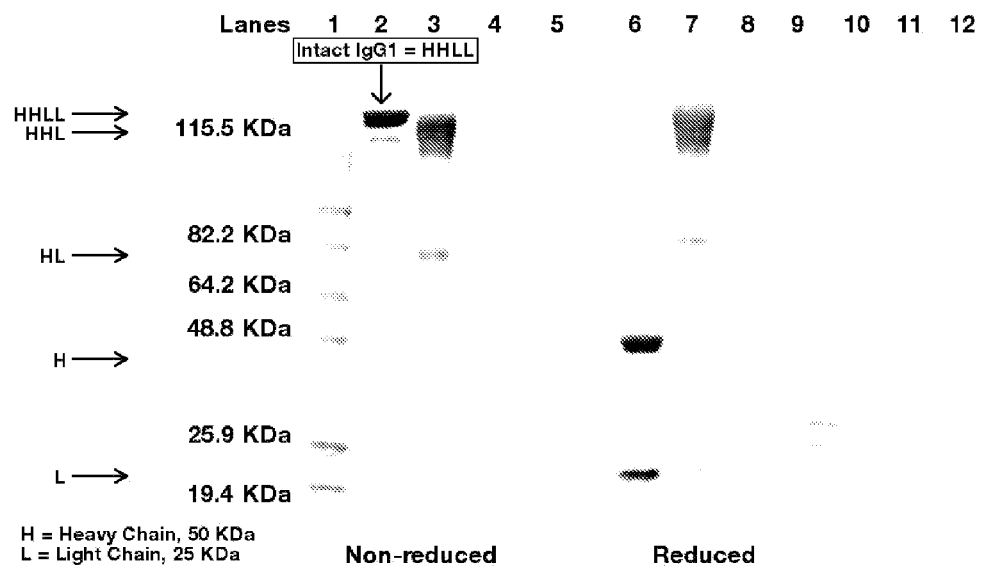
FIG. 2 shows a SDS-PAGE (sodium dodecyl sulfate-polyacrylamide gel electrophoresis) of an IgG1 Antibody-bromomethylacrylate (1) conjugate under reducing and non-reducing conditions.

Lane 1 in FIG. 2 shows molecular weight markers (KDaltons). Lane 2 in FIG. 2 is an intact mAb1 (unconjugated, non-reduced). Lane 3 in FIG. 2 is mAb1-1 conjugate treated with dhAA (conjugated, oxidized, non-reduced). The minor band in Lane 3 around 75 KDa is believed to represent heavy-light chain "half-antibody" molecules (represented in FIG. 2 as "HL"). Lanes 4 and 5 in FIG. 2 are blank. Lane 6 in FIG. 2 is mAb1 under reducing condition, which manifests as separate heavy chain and light chain bands. Lane 7 in FIG. 2 is mAb1-1 conjugate treated with dhAA under reducing condition. Lanes 8, 9, 10, 11, and 12 are blank. As shown in FIG. 2, Lane 7, the mAb1-1 conjugate remained substantially intact under reducing conditions, suggesting that the disulfide linkages formed by the bromomethacrylate compound served to stabilize the antibody and prevent dissociation of the immunoglobulin heavy and light chains under reducing conditions.

Without being bound by any theory, the results of these experiments as analyzed by reduced and non-reduced SDS-PAGE suggests that mAb1 forms a stable conjugate after the free sulfhydryl groups obtained via reducing the disulfide bonds between the cysteine residues on mAb1 reacts with compound 1. Further, the compound 1 tethers the two free sulfhydryl groups on mAb1 via covalent bonds. Therefore, mAb1-1 conjugate maintains its structure under reducing conditions.

This proof-of-concept experiment therefore demonstrates that the linker-drug compounds of the present disclosure, which are analogous to the compound 1 test compound used in this Example, can be used to conjugate a variety of drugs, toxins and other molecules to antibodies via cysteine residues, while maintaining the structural integrity of the resulting antibody-drug conjugate.

Example 2

Other proof-of-concept linker molecules (i.e., methyl 3-bromo-2-(bromomethyl)propanoate (2) [Sigma Aldrich]), representative of the linker-drug molecules of the present disclosure, were conjugated to a reduced IgG1 antibody at cysteine residues on the antibody, and the resulting conjugate molecule was assessed using SDS-PAGE under non-reducing and reducing conditions as in Example 1 (Tris/Glycine 4-12%, Coomassie Stain).

2-Bromomethyl-N-(1-phenyl-ethyl)-acrylamide (6)

2-Bromomethyl-acrylic acid (2.0 g; 12.12 mmol) was dissolved in thionyl chloride (2.6 mL; 4.3 g; 36.36 mmol) in a 50 mL 3-neck round bottom flask equipped with a magnetic stirrer, thermocouple, condenser and nitrogen inlet. This clear brown solution was refluxed at 90-92° C. for 3 hours and then concentrated in vacuo to afford 2.01 grams (90.5% yield) of the corresponding acid chloride 4.

To another 50 mL 3-neck round bottom flask equipped with a magnetic stirrer, addition funnel, thermocouple and nitrogen inlet was charged R-1-phenyl-ethylamine (275 mg; 2.27 mmol), cat. DMAP (28 mg; 0.23 mmol, 0.1 eq) and DCM (10 mL). This solution was chilled to 0° C. via an ice bath. The 2-Bromomethyl-acryloyl chloride 4 (500 mg; 2.73 mmol, 1.2 eq) was also diluted with DCM (10 mL), chilled to 0° C. and slowly added to the reaction mixture via addition funnel. The reaction was stirred in the ice bath and slowly warmed to room temperature overnight. The reaction was diluted with ethyl acetate and washed with Na$_2$SO$_4$, filtered and concentrated in vacuo to dryness, the crude product was dissolved in minimum amount of DCM and purified on silica gel (0-100% EtOAc in hexane). The cleanest fractions (by LC) were combined and concentrated to dryness giving the title compound as white solid (0.12 g, 20%). $^1$H-NMR (300 MHz, CDCl$_3$): 7.39-7.25 (m, 5H), 6.27 (br s, 1H), 5.84 (s, 1H), 5.68 (s, 1H), 5.24-5.13 (m, 1H), 4.33-4.31 (app. d, 2H), 1.56-1.54 (d, 3H)

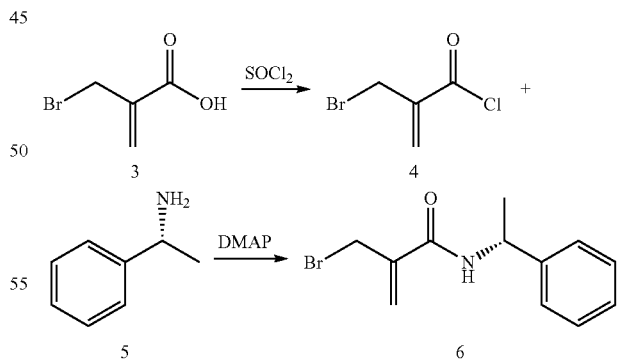

3-Bromo-2-bromomethyl-N-(1-phenyl-ethyl)-propionamide (9)

3-Bromo-2-bromomethyl-propionic acid (1.0 g; 4.07 mmol) was dissolved in thionyl chloride (0.9 mL; 1.45 g; 12.2 mmol) in a 25 mL 3-neck round bottom flask equipped with a magnetic stirrer, thermocouple, condenser and nitrogen inlet. This clear brown solution was refluxed at 90-92° C. for 3 hours and then concentrated in vacuo to afford 0.89 grams (83% yield) of the corresponding acid chloride. ¹H-NMR (300 MHz, CDCl₃): δ 3.85-3.75 (m, 4H), 3.60 (pentet, 1H, J=9 Hz).

To another 50 mL 3-neck round bottom flask equipped with a magnetic stirrer, addition funnel, thermocouple and nitrogen inlet was charged R-1-phenyl-ethylamine (149 mg; 1.23 mmol), cat. DMAP (18 mg; 0.15 mmol, 0.1 eq) and DCM (10 mL). This solution was chilled to 0° C. via an ice bath. The 3-Bromo-2-bromomethyl-propionyl chloride 8 (390 mg; 1.48 mmol, 1.2 eq) was also diluted with DCM (10 mL), chilled to 0° C. and slowly added to the reaction mixture via addition funnel. The reaction was stirred in the ice bath and slowly warmed to room temperature overnight. The reaction was diluted with ethyl acetate and washed with Na₂SO₄, filtered and concentrated in vacuo to dryness, the crude product was dissolved in minimum amount of DCM and purified on silica gel (0-100% EtOAc in hexane). The cleanest fractions (by LC) were combined and concentrated to dryness giving the title compound as white solid (0.13 g, 24%). ¹H-NMR (300 MHz, CDCl₃): 7.36-7.25 (m, 5H), 6.03-6.01 (d, 1H), 5.22-5.13 (m, 1H), 3.65-3.45 (m, 4H), 2.92-2.82 (m, 1H), 1.55-1.53 (d, 3H)

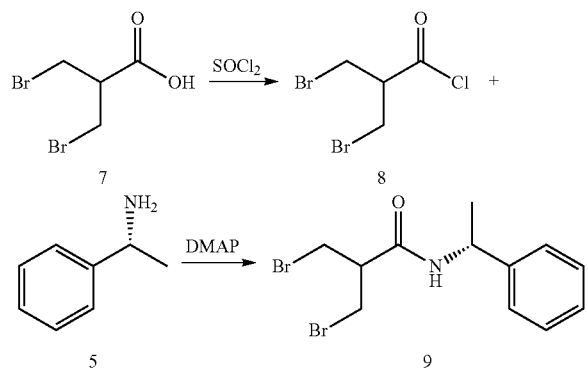

Conjugate Preparation and Characterization

Figure 3:
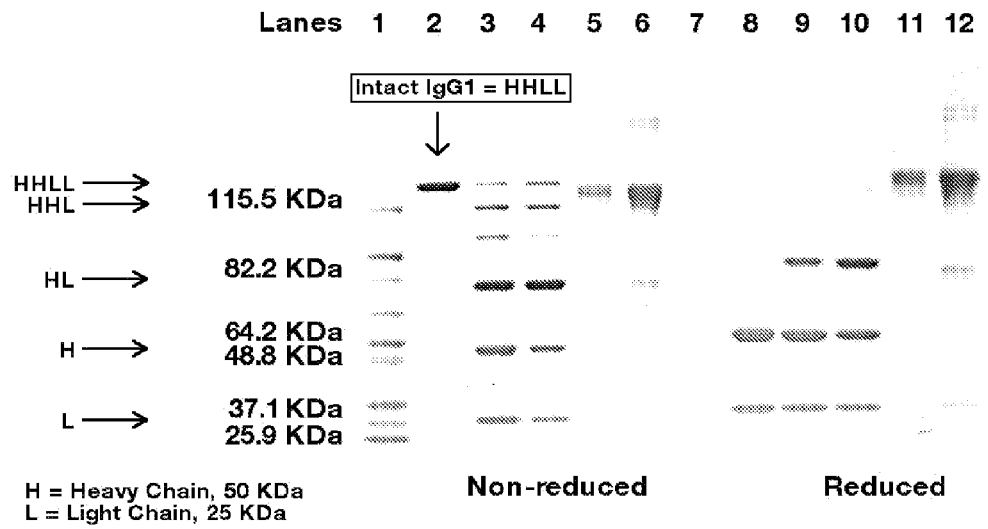
FIG. 3 shows a SDS-PAGE of an IgG1 antibody conjugated to exemplary small molecule conjugates 1, 2, 6, and 9 under reducing and non-reducing conditions.

Briefly, a test monoclonal antibody of Fc isotype IgG1 ("mAb1," 10 mg/ml) in 50 mM HEPES, 150 mM NaCl, pH 7.5, was reduced with 1 mM dithiothreitol (0.006 mg per mg of antibody) at 37° C. for 30 min. After gel filtration (G-25, pH 4.5 sodium acetate), the reunion reagent 1, 2, 6, or 9 (1.2 equivalents/disulfide) in DMSO (10 mg/ml) was added to the reduced antibody, the mixture was adjusted to pH 7.0 with 1 M HEPES (pH 7.4), and allowed to react for 4 h. Immediately following the alkylation, the antibody was oxidized with 0.5 mM dehydroascorbic acid (dhAA) for 4 h. The conjugate was purified by size exclusion chromatography. Protein concentrations were determined by UV spectral analysis. Size-exclusion HPLC established that all conjugates were >95% monomeric. FIG. 3 contains the reduced and non-reduced SDS-PAGE gel of the conjugates (Tris/Glycine 4-12%, Coomassie Stain).

Lane 1 in FIG. 3 shows molecular weight markers (KDaltons). Lane 2 in FIG. 3 is an intact mAb1 (unconjugated, non-reduced). Lanes 3 and 4 are mAb1-6 and mAb1-9 conjugates, respectively. The major band in Lanes 3 and 4 around 75 KDa corresponds to the heavy-light chain "half-antibody" molecules (represented in FIG. 3 as "HL"). Lanes 5 and 6 in FIG. 3 are mAb1-2 and mAb1-1 conjugates, respectively. The major band around 150 KDa for both conjugates corresponds to the intact antibody. Lane 7 is a blank. Lane 8 in FIG. 3 is mAb1 under reducing conditions, which manifests as separate heavy chain and light chain bands. Lanes 9 and 10 are mAb1-6 and mAb1-9 conjugates, respectively, under reducing conditions. In those lanes, 3 bands are present that correspond to light chain (25 KDa), heavy chain (50 KDa), and heavy-light chain or "half-antibody" molecules. Lanes 11 and 12 in FIG. 3 are mAb1-2 and mAb1-1 conjugates, respectively, under reducing conditions. The major band around 150 KDa for both conjugates corresponds to the intact antibody. As shown in FIG. 3, Lanes 11 and 12, the mAb1-2 and mAb1-1 conjugates remained substantially intact under reducing conditions, suggesting that the disulfide linkages formed by the disulfide reunion compounds served to stabilize the antibody and prevent dissociation of the immunoglobulin heavy and light chains under reducing conditions.

Without being bound by any theory, the results of these experiments as analyzed by reduced and non-reduced SDS-PAGE suggests that mAb1 forms a stable conjugate after the free sulfhydryl groups obtained via reducing the disulfide bonds between the cysteine residues on mAb1 reacts with the disulfide reunion compounds. Further, the tethers formed on the two free sulfhydryl groups on mAb1 are covalent bonds. Therefore, mAb1-6 and mAb1-9 conjugates maintain a majority of their structure under reducing conditions and in the mAb1-2 and mAb1-1 conjugates approximately all of the IgG structure remains intact.

This additional proof-of-concept experiment therefore demonstrates that the linker-drug compounds of the present disclosure, which are analogous to compounds 1, 2, 6, and 9 used in this Example, can be used to conjugate a variety of drugs, toxins and other molecules to antibodies via cysteine residues, while maintaining the structural integrity of the resulting antibody-drug conjugate.

Example 3

Linker Synthesis

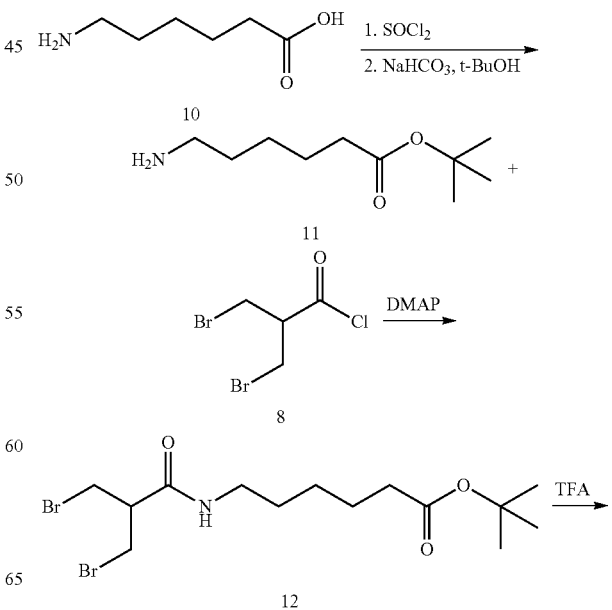

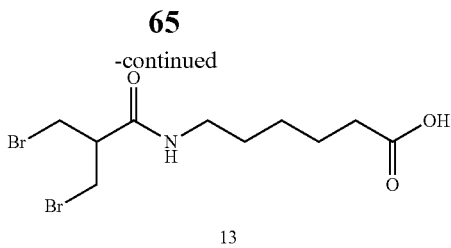

13

-(3-Bromo-2-bromomethyl-propionylamino)-hexanoic acid (13)

Step 1: Preparation of 6-Amino-hexanoic acid tert-butyl ester (11)

To a 50 mL round bottom flask equipped with a magnetic stirrer and nitrogen inlet was charged 6-aminohexanoic acid (2.0 g; 15 mmol) and thionyl chloride (5.0 mL; 69 mmol; 4.5 equiv.). This solution was stirred at or below 30° C. for 2 hours and concentrated in vacuo to dryness. To the tan semi-solid a slurry of sodium bicarbonate (2.6 g; 30 mmol; 2.0 equiv.) in t-BuOH (5.0 mL; 87 mmol; 5.7 equiv.) was added and the slurry was stirred at ambient temperature for another 2 h. The butanol was removed in vacuo at 40° C. The thick white slurry was diluted with ethyl acetate and washed with 4 portions of 1 N NaOH, 3 portions of $H_2O$, 1 portion of brine. The organics were dried over $Na_2SO_4$, filtered and concentrated to afford 2.2 g (77% yield) as a colorless oil. MS (ESI, pos.): calc'd for $C_{10}H_{21}NO_2$, 187.3; found 188.4 (M+H), $^1$H-NMR (300 MHz, $CDCl_3$): δ 2.68-2.64 (m, 2H), 2.21-2.16 (m, 2H), 1.62-1.52 (m, 2H), 1.48-1.38 (m, 9H), 1.36-1.20 (m, 2H), 1.09 (m, 2H).

Step 2: Preparation of 6-(3-Bromo-2-bromomethyl-propionylamino)-hexanoic acid tert-butyl ester (12)

To a 50 mL round bottom flask equipped with a magnetic stirrer and nitrogen inlet was charged 6-aminohexanoic acid tert-butyl ester 11 (0.50 g; 2.7 mmol) and dimethylaminopyridine (0.03 g; 0.27 mmol; 0.10 equiv.) in DCM (5.0 mL). This solution was chilled to 0° C. via an ice bath. 3-Bromo-2-bromomethyl-propionyl chloride 8 (0.90 g; 3.4 mmol; 1.2 equiv.) was dissolved in DCM (5 mL) and slowly added to the reaction mixture at 0° C. Stir and slowly warm to ambient temperature overnight. Dilute reaction mixture with ethyl acetate, wash the organic mixture with $H_2O$, 5% $NaHCO_3$ and brine. The organics were dried over $Na_2SO_4$, filtered, concentrated and purified on a silica gel column eluting with 0-100% ethyl acetate in hexanes to afford 0.49 g (42% yield) as a clear yellow oil. $^1$H-NMR (300 MHz, $CDCl_3$): δ 5.92 (br s, 1H), 3.64-3.58 (m, 2H), 3.54-3.48 (m, 2H), 3.36-3.29 (m, 2H), 2.89-2.83 (m, 1H), 2.24-2.20 (m, 2H), 1.65-1.51 (m, 4H), 1.44-1.35 (m, 11H).

Step 3: Preparation of 6-(3-Bromo-2-bromomethyl-propionylamino)-hexanoic acid (13)

To a 50 mL round bottom flask equipped with a magnetic stirrer and nitrogen inlet was charged 6-(3-Bromo-2-bromomethyl-propionylamino)-hexanoic acid tert-butyl ester 12 (0.26 g; 0.62 mmol) and trifluoroacetic acid (0.70 mL; 9.3 mmol; 15 equiv.) in DCM (10 mL). This solution was stirred at ambient temperature overnight, concentrated to dryness, dissolved in acetonitrile and $H_2O$ (1.0 mL each), frozen and lyophilized to afford 0.22 g (100%) as a solid. MS (ESI, pos.): calc'd for $C_{10}H_{17}Br_2NO_3$, 359.0 found 358.0, 360.0, 362.0 (M+H), 380.0, 382.0, 384.0 (M+Na), 356.0, 358.0, 360.0 (M−H). $^1$H-NMR (300 MHz, $CDCl_3$): δ 11.97 (s, 1H), 8.20-8.16 (m, 1H), 3.58-3.56 (d, 4H), 3.11-3.04 (m, 2H), 3.02-2.97 (m, 1H), 2.21-2.16 (m, 2H), 1.54-1.37 (m, 4H), 1.33-1.29 (m, 2H).

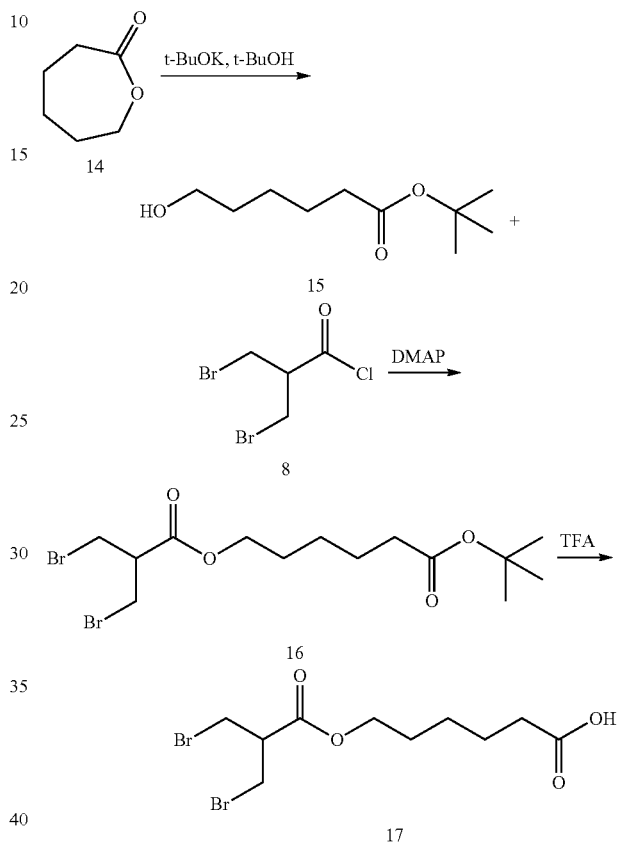

6-(3-Bromo-2-bromomethyl-propionyloxy)-hexanoic acid (17)

Step 1: Preparation of 6-Hydroxy-hexanoic acid tert-butyl ester (15)

To a 250 mL round bottom flask equipped with a magnetic stirrer, thermocouple, condenser and nitrogen inlet was charged 6-hexanolactone 14 (3.7 g; 32 mmol) and t-BuOH (100 mL) in DCM followed by t-BuOK (3.9 g; 35 mmol; 1.1 equiv.). This solution was stirred and heated to reflux for 3 hours. The solution was diluted with toluene, washed with water and brine, dried over $Na_2SO_4$, filtered and concentrated to afford 4.8 g (80% yield) as a clear yellow oil. $^1$H-NMR (500 MHz, $CDCl_3$): δ 3.65-3.62 (m, 2H), 2.32-2.29 (m, 1H), 2.23-2.20 (m, 2H), 1.66-1.55 (m, 4H), 1.43 (s, 9H), 1.41-1.35 (m, 2H).

Step 2: Preparation of 6-(3-Bromo-2-bromomethyl-propionyloxy)-hexanoic acid tert-butyl ester (16)

To a 50 mL round bottom flask equipped with a magnetic stirrer and nitrogen inlet was charged 6-Hydroxy-hexanoic acid tert-butyl ester 15 (0.50 g; 2.7 mmol) and dimethylaminopyridine (0.03 g; 0.27 mmol; 0.10 equiv.) in DCM (5.0 mL). This solution was chilled to 0° C. via an ice bath. 3-Bromo-2-bromomethyl-propionyl chloride 8 (0.90 g; 3.4 mmol; 1.3 equiv.) was dissolved in DCM (5.0 mL) and slowly added to the reaction mixture at 0° C. The mixture was stirred and slowly warmed to ambient temperature overnight. The reaction mixture was diluted with ethyl acetate, wash the organic mixture with $H_2O$, 5% $NaHCO_3$ and brine. The organics were dried over $Na_2SO_4$, filtered, concentrated and purified on a silica gel column eluting with 0-100% ethyl acetate in hexanes to afford 0.75 g (78% yield) as a clear yellow oil. $^1$H-NMR (300 MHz, CDCl$_3$): δ 4.21-4.15 (m, 2H), 3.80-3.68 (m, 4H), 3.21-3.15 (m, 1H), 2.40-2.31 (m, 2H), 1.71-1.59 (m, 4H), 1.42-1.37 (m, 11H).

Step 3: Preparation of 6-(3-Bromo-2-bromomethyl-propionyloxy)-hexanoic acid (17)

To a 50 mL round bottom flask equipped with a magnetic stirrer and nitrogen inlet was charged 6-(3-Bromo-2-bromomethyl-propionyloxy)-hexanoic acid tert-butyl ester 16 (0.70 g; 1.7 mmol) and trifluoroacetic acid (1.3 mL; 17 mmol; 10 equiv.) in DCM (10 mL). This solution was stirred at ambient temperature overnight, concentrated and purified on a silica gel column eluting with 0-100% ethyl acetate in hexanes to afford 0.34 g (56% yield) as a clear colorless oil. MS (ESI, pos.): calc'd for $C_{10}H_{16}Br_2O_4$, 360.0; found 380.8, 382.8, 384.8 (M+Na), 276.0, 278.0 (M–H). $^1$H-NMR (300 MHz, CDCl$_3$): δ 4.21-4.16 (m, 2H), 3.80-3.67 (m, 4H), 3.22-3.16 (m, 1H), 2.40-2.35 (m, 2H), 1.75-1.63 (m, 4H), 1.50-1.39 (m, 2H).

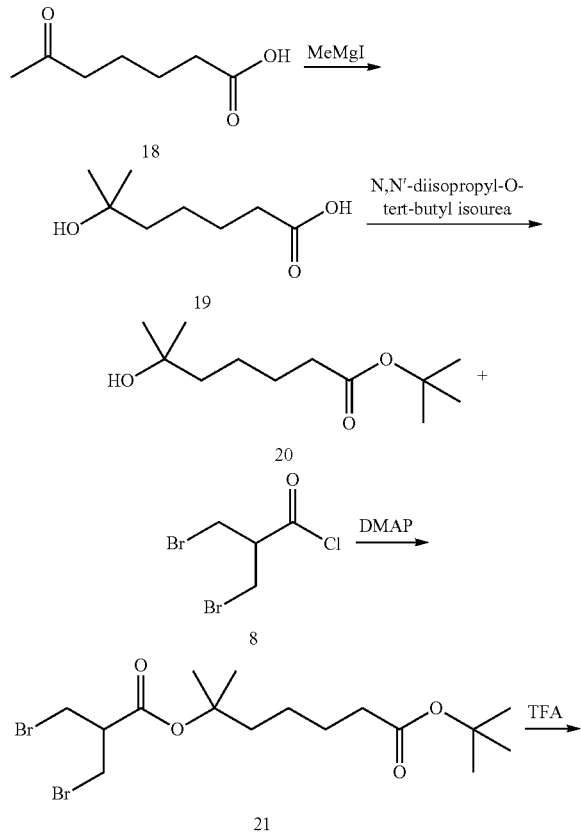

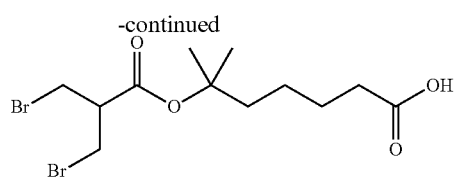

6-((3-bromo-2-(bromomethyl)propanoyl)oxy)-6-methylheptanoic acid (22)

Step 1: Preparation of 6-Hydroxy-6-methyl-heptanoic acid (19)

To a 250 mL 3-neck round bottom flask equipped with a magnetic stirrer, addition funnel, condenser, thermocouple and nitrogen inlet was charged 5-acetylvaleric acid 18 (1.0 g; 6.9 mmol) and anhydrous THF (50 mL). This solution was stirred and chilled to –78° C. via dry ice/acetone bath. To this cold solution 1.4 M MeMgI in THF/toluene (29 mL; 40 mmol; 5.8 eq) was added slowly via addition funnel over 15 min. The reaction was stirred at –78° C. for 2 h, then slowly warmed to –10° C. and saturated aq. $NH_4Cl$ solution was added to quench the excess Grignard. The biphasic mixture was warmed to ambient temperature, diluted with ethyl acetate, the organic layer was discarded. The aqueous layer was acidified with 1 M HCl and extracted with ethyl acetate (3×50 mL). The organic phases were combined, washed with brine, dried over $Na_2SO_4$, filtered and concentrated to afford 0.63 g (57% yield) as a clear colorless oil. $^1$H-NMR (500 MHz, CDCl$_3$): δ 2.39-2.36 (m, 2H), 1.68-1.62 (m, 2H), 1.51-1.47 (m, 2H), 1.45-1.40 (m, 2H), 1.21 (s, 6H).

Step 2: 6-Hydroxy-6-methyl-heptanoic acid tert-butyl ester (20)

To a 100 mL 3-neck round bottom flask equipped with a magnetic stirrer, addition funnel, condenser, thermocouple and nitrogen inlet was charged 6-Hydroxy-6-methyl-heptanoic acid 19 (0.68 g; 4.2 mmol) and DCM (30 mL). This solution was stirred at ambient temperature and the N,N'-diisopropyl-O-tert-butyl isourea (2.6 g; 13 mmol) was added dropwise via addition funnel. The reaction was stirred overnight and then heated to 40° C. for 3 h. The solvent was removed and the crude product was purified on a silica gel flash column eluting with 0-50% ethyl acetate in hexanes, and product fractions evaporated in vacuo giving the title compound as a clear colorless oil (0.28 g, 30% yield). $^1$H-NMR (500 MHz, CDCl$_3$): δ 2.25-2.21 (t, 2H), 1.63-1.57 (q, 2H), 1.49-1.46 (m, 2H), 1.44 (m, 9H), 1.41-1.36 (m, 2H), 1.21 (s, 6H).

Steps 3-4: Preparation of Compounds 21 and 22

Compound 20 can be acylated with compound 8 using DMAP to yield compound 21 and trifluoroacidic acid removal of the t-butyl protecting group would furnish the desired hindered functionalized acid linker 22 that can be couple to payloads and linker payloads.

Example 4

Maytansinoid Linker Payloads

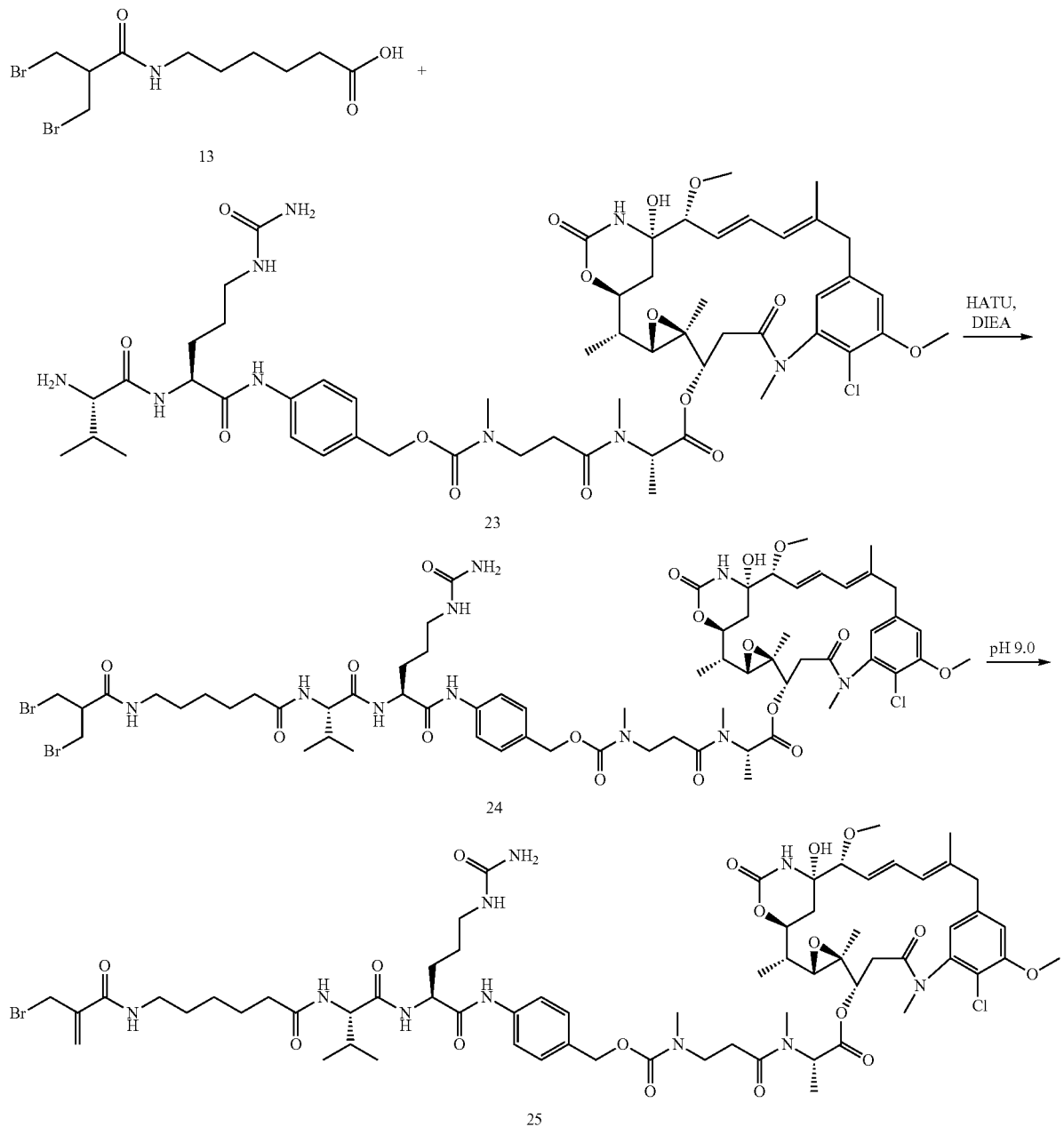

Compound 23 was prepared as a white solid (0.074 g, 63%) according to the method described in WO2014145090. MS (ESI, pos.): calc'd for $C_{55}H_{78}ClN_9O_{15}$, 1139.5; found 1141.4 (M+H).

6-(3-Bromo-2-bromomethyl-propanamido)-caproamido-L-valine-L-citrulline-p-amino-benzyl-carbamoyl-N-methyl-beta-alanine-N-methyl-L-alanine-maytansine-3-ester (24)

Compound 23 (0.016 g, 0.013 mmol), compound 13 (0.016 g, 0.045 mmol) and HATU (0.024 g, 0.063 mmol) were weighed into a dry round-bottom flask, dissolved in DMF (3.0 mL), and treated with DIEA (0.010 mL, 0.057 mmol) via syringe. The flask was purged with argon, sealed with a rubber septum, and stirred at ambient temperature for 22 h. The reaction was diluted with water and purified on a 100 g C18 Aq RediSep Gold column via ISCO CombiFlash system (20-80% MeCN in water, 0.05% HOAc both, over 15 mins, 50 mL/min), and the cleanest fractions frozen and lyophilized giving the title compound as a white solid (0.015 g, 75%). MS (ESI, pos.): calc'd for $C_{65}H_{93}Br_2ClN_{10}O_{17}$, 1480.5/1481.5 (most abundant isotopes); found 1481.5/1483.6 (M+H).

71

2-(Bromomethyl)-acrylamido-6-caproamido-L-valine-L-citrulline-p-aminobenzylcarbamoyl-N-methyl-beta-alanine-N-methyl-L-alanine-maytansine-3-ester (25)

Compound 24 (0.021 g, 0.014 mmol) was dissolved in MeCN (4.0 mL), treated with pH 9.00 buffer (4.0 mL, Fisher Chemical #SB114-500), the flask purged with argon, sealed with a rubber septum, and stirred at ambient temperature for 20 h. The reaction was frozen on dry ice, lyophilized to a solid, dissolved in 1:1 MeCN/water, and purified on a 50 g C18 Aq RediSep Gold column via ISCO CombiFlash system (20-80% MeCN in water, 0.05% HOAc both, over 12 mins, 40 mL/min), and the cleanest fractions frozen and lyophilized giving the title compound as a white solid (0.013 g, 65%). MS (ESI, pos.): calc'd for $C_{65}H_{92}BrClN_{10}O_{17}$, 1400.6 (most abundant isotope); found 1401.5 (M+H).

72

2-(Bromomethyl)-acrylato-6-caproamido-L-valine-L-citrulline-p-aminobenzylcarbamoyl-N-methyl-beta-alanine-N-methyl-L-alanine-maytansine-3-ester (26)

Compound 17 (0.022 g, 0.061 mmol), compound 23 (0.024 g, 0.020 mmol), and HATU (0.038 g, 0.10 mmol) were weighed into a dry round-bottom flask, dissolved in DMF (3.0 mL), and treated with DIEA (0.02 mL, 0.12 mmol) via syringe. The flask was purged with argon, sealed with a rubber septum, and stirred at ambient temperature for 24 h. The reaction was concentrated in vacuo to an oil, dissolved in 1:1 MeCN/water, treated with 1 drop of 10% aq. HOAc, and purified on a 50 g C18 Aq RediSep Gold column via ISCO CombiFlash system (20-80% MeCN in water, 0.05% HOAc both, over 12 mins, 40 mL/min), and the cleanest fractions frozen and lyophilized giving the title

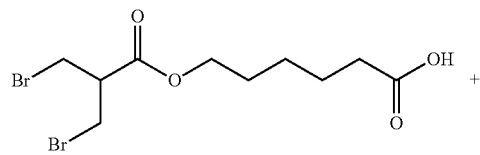

17

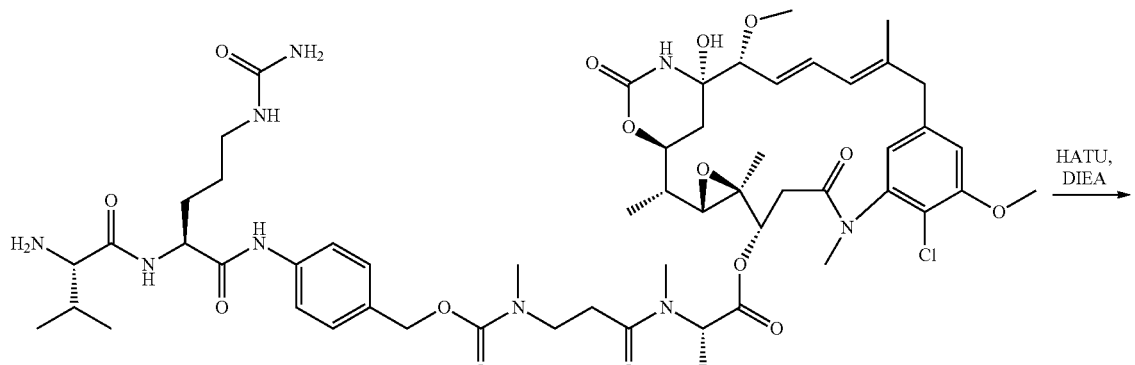

23

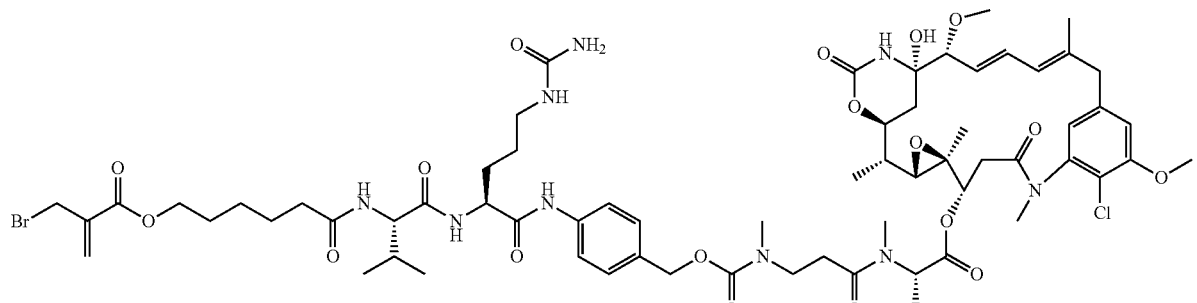

26 compound as a white solid (0.012 g, 43%). MS (ESI, pos.): calc'd for $C_{65}H_{91}BrClN_9O_{18}$, 1401.5 (most abundant isotope); found 1402.6 (M+H).

Example 5

Auristatin Linker Payloads

2-(Bromomethyl)-acrylamido-6-caproamido-monomethylauristatin F (29)

Compound 28 (0.013 g, 0.012 mmol) was dissolved in MeCN (2.0 mL), treated with pH 9.00 buffer (2.0 mL, Fisher Chemical #SB114-500), the flask purged with argon, sealed with a rubber septum, and stirred at ambient temperature for

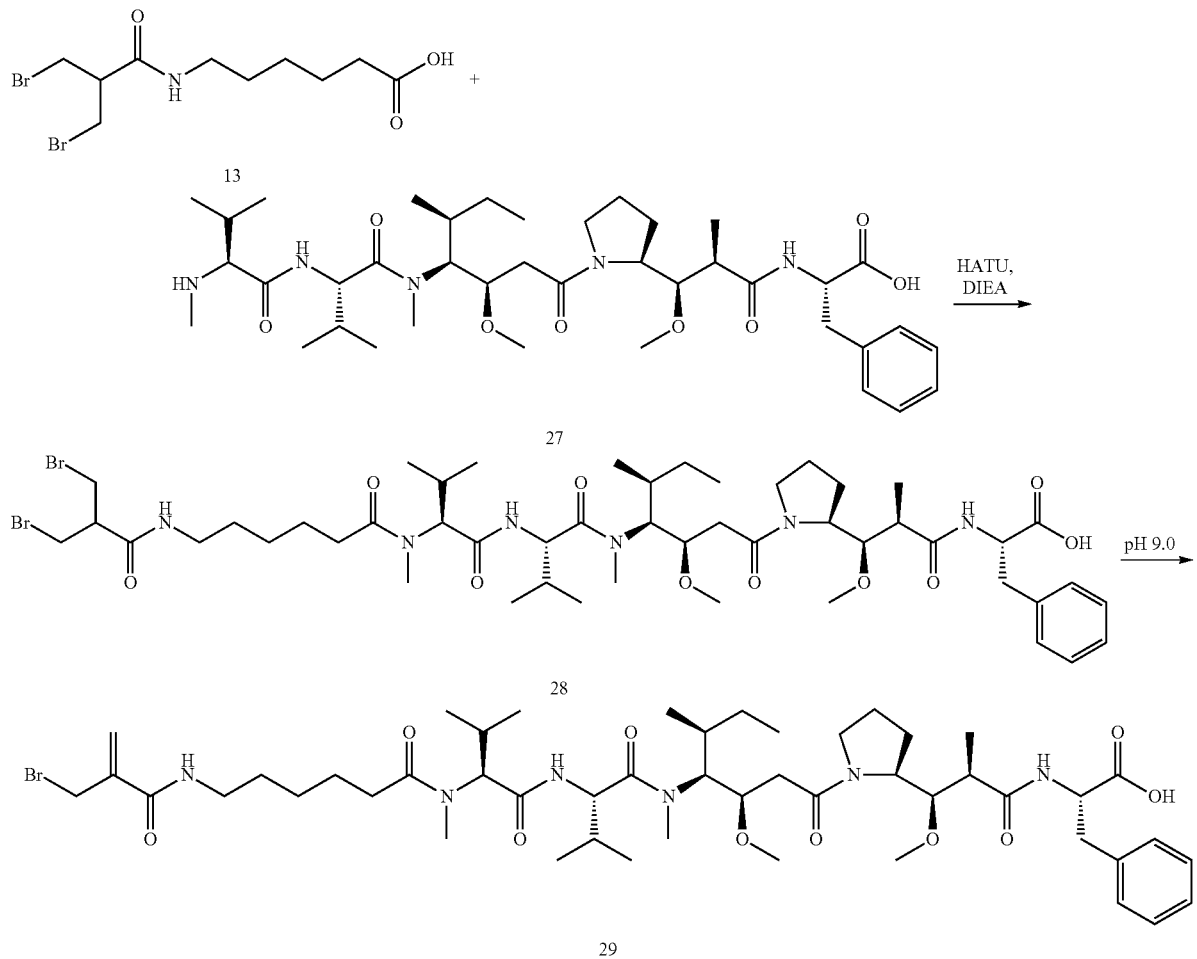

6-(3-Bromo-2-bromomethyl-propanamido)-caproamido-monomethylauristatin F (28)

Compound 13 (0.040 g, 0.11 mmol) and HATU (0.033 g, 0.087 mmol) were weighed into a dry round-bottom flask, dissolved in DMF (2.0 mL), and treated with DIEA (0.030 mL, 0.17 mmol) via syringe. The flask was purged with argon, sealed with a rubber septum, and stirred at ambient temperature for 0.5 h. A solution of Monomethyl Auristatin F 27 (0.034 g, 0.046 mmol) in DMF (1.0 mL) was then added, the flask purged again with argon and resealed, and the reaction stirred another 18 h. The reaction was diluted with water (3 mL) and purified on a 100 g C18 Aq RediSep Gold column via ISCO CombiFlash system (20-80% MeCN in water, 0.05% HOAc both, over 17 mins, 50 mL/min). The product-containing fractions by LCMS were combined, frozen in a dry ice/acetone bath, and lyophilized giving the title compound as a white solid (0.024 g, 44%). MS (ESI, pos.): calc'd for $C_{49}H_{80}Br_2N_6O_{10}$, 1072.4 (most abundant isotope); found 1073.5 (M+H).

40 h. The reaction showed only 56% conversion to product by LCMS, so saturated aq. NaHCO3 was added to bring the pH up to 8.5 and the reaction stirred another 7 h at ambient temperature. The reaction was acidified with 10% aq. HOAc (1.0 mL) and purified on a 50 g C18 Aq RediSep Gold column via ISCO CombiFlash system (20-80% MeCN in water, 0.05% HOAc both, over 12 mins, 40 mL/min). The product-containing fractions by LCMS were combined, frozen in a dry ice/acetone bath, and lyophilized giving the title compound as a white solid (9 mg). This was only 85% pure by HPLC, so it was repurified on a 30 g C18 Aq RediSep Gold column via ISCO CombiFlash system (20-80% MeCN in water, 0.05% HOAc both, over 12 mins, 30 mL/min), and the cleanest fractions frozen and lyophilized giving the title compound as a white solid (0.005 g, 42%). MS (ESI, pos.): calc'd for $C_{55}H_{78}ClN_9O_{15}$, 990.5/992.5 (most abundant isotopes); found 991.5/993.5 (M+H).

Conjugate Preparation and Characterization

An anti-PRLR monoclonal antibody from US20150056222 (WO2015026907), H1H6765P, and a nontargeting monoclonal antibody both with Fc isotype IgG1 (10 mg/ml) in 50 mM HEPES, 150 mM NaCl, pH 7.5, was reduced with 1 mM dithiothreitol (0.006 mg per mg of antibody) at 37° C. for 30 min. After gel filtration (G-25, pH 4.5 sodium acetate), one of the compounds 26, 28, or 29 (1.2 equivalents/disulfide) in DMSO (10 mg/ml) was added to the reduced antibody, the mixture was adjusted to pH 7.0 with 1 M HEPES (pH 7.4), and allowed to react for 4 h. Immediately following the alkylation, the antibody was oxidized with 0.5 mM dehydroascorbic acid (dhAA) for 4 h or allowed to air oxidized. The conjugate was purified by size exclusion chromatography. Protein concentrations were determined by UV spectral analysis. Size-exclusion HPLC established that all conjugates were >95% monomeric. Drug to antibody ratios (DAR) for the maytansinoid conjugates of 26 were determined using the extinction coefficients 280 nm =8115 cm$^{-1}$ M$^{-1}$ and 252 nm=49407 cm$^{-1}$ M$^{-1}$, which yielded a DAR of 2. The auristatin conjugate DARs were not determined. Conjugates were analyzed by reduced and non-reduced SDS-PAGE and FIG. 4 contains the gel (Tris/Glycine 4-12%, Coomassie Stain).

Figure 4:
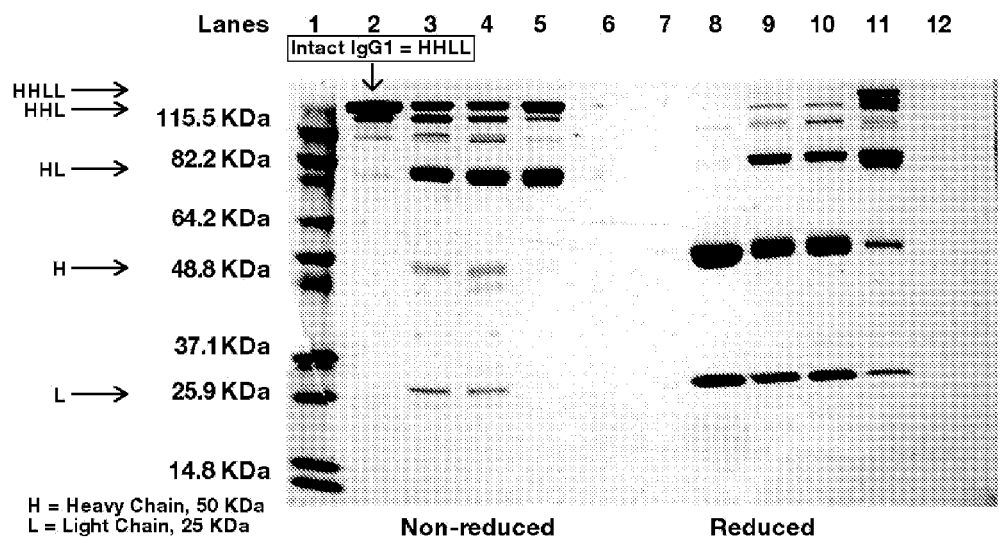
FIG. 4 shows a SDS-PAGE of an anti-PRLR antibody conjugated to exemplary linker payloads H1H6765P-26, H1H6765P-28 and H1H6765P-29 under reducing and non-reducing conditions.

Lane 1 in FIG. 4 shows molecular weight markers (KDaltons). Lane 2 in FIG. 4 contains intact H1H6765P antibody (unconjugated, non-reduced). In lanes 3 and 4 are H1H6765P-28 and H1H6765P-29 conjugates, respectively. Three major bands are present in Lanes 3 and 4 around 75, 125, and 150 KDa corresponding to the heavy-light chain "half-antibody," heavy-heavy-light antibody, and intact antibody conjugates. In Lane 5 of FIG. 4 is H1H6765P-26 with only major bands around 75 and 150 KDa corresponding to the heavy-light chain "half-antibody," and intact antibody conjugates respectively. Lanes 6 and 7 are blank. Lane 8 in FIG. 4 contains H1H6765P under reducing conditions, which manifests as separate heavy chain and light chain bands. Lanes 9 and 10 are H1H6765P-28 and H1H6765P-29 conjugates, respectively, under reducing conditions. In those lanes, 3 major bands around 25, 50, and 75 KDa correspond to the light chain, heavy chain, and heavy-light chain "half-antibody" conjugates, respectively. Lane 11 in FIG. 4 contains conjugate H1H6765P-26 under reducing conditions. In that lane, the bands present around 75, 125, and 150 KDa correspond to the heavy-light chain "half-antibody," heavy-heavy-light antibody, and intact antibody conjugates. As shown in FIG. 4, Lanes 9-10 the conjugates remained partially intact under reducing conditions. In lane 11 the H1H6765P-26 remained substantially intact suggesting that the disulfide linkages formed by the disulfide reunion linker payload served to stabilize the antibody and prevent dissociation of the immunoglobulin heavy to light and heavy to heavy chains under reducing conditions.

Conjugate Analysis by Mass Spectrometry

Conjugates H1H6765P-28 and H1H6765-26 were analyzed by ESI-MS on a Thermo Q-Exactive (Hybrid Quadrupole-Orbitrap) equipped with a Shimadzu HPLC with prominence LC-20AD pump, SIL-20AC HT autosample and SPD-20A UV detector.

Each conjugate was diluted with MilliQ water to 1 mg/mL. PNGase F (P0704L, New England Biolabs) was diluted with MilliQ water to 75,000 U/mL. 5 uL of the diluted PNGase F was added to 50 uL of each sample and the samples were incubated at 37° C. with shaking (500 RPM) overnight. 5 uL of each sample was injected to LC-MS system.

Chromatographic separation was achieved by a LC gradient composing of mobile phase A (0.1% formic acid in water) and mobile phase B (0.1% formic acid in acetonitrile) with the gradient shown in Table 1. Flow rate was set at 0.4 ml/min. Waters BEH C18 column (50×2.1 mm 1.7 um particle size) was kept at 60° C. during the analysis. The flow between 3-14 min was directed to MS and others were directed to waste.

TABLE 1

LC gradient

| Minute | | | | | | |
|---|---|---|---|---|---|---|
| 0.01 | 3 | 13.9 | 14 | 16 | 17 | 24 |
| % B  10 | 10 | 90 | 95 | 95 | 10 | 10 |

Mass Spectrometric Setting

Thermo Q-Exactive with HESI ionization source was used to detect eluents from LC. The other major parameters are listed in Table 2.

TABLE 2

Q-Exactive parameters for intact mass analysis

| Parameter | Scan Range | Resolution | AGC | Maximum IT | In source CID |
|---|---|---|---|---|---|
| Value | 700-4000 Da | 17,500 | 5e6 | 200 ms | 80.0 eV |
| Parameter | Spray Voltage | Aug gas | Spare gas | Capillary temperature | |
| Value | 4400 V | 10 | 8 | 250° C. | |

Collected mass spectrum was deconvoluted by using Thermo Protein Deconvolution software. Manual ReSpect™ was selected as the Experiment Types. Noise rejection was set to 95% confidence and mass tolerance was set to 25 ppm.

Figure 5:
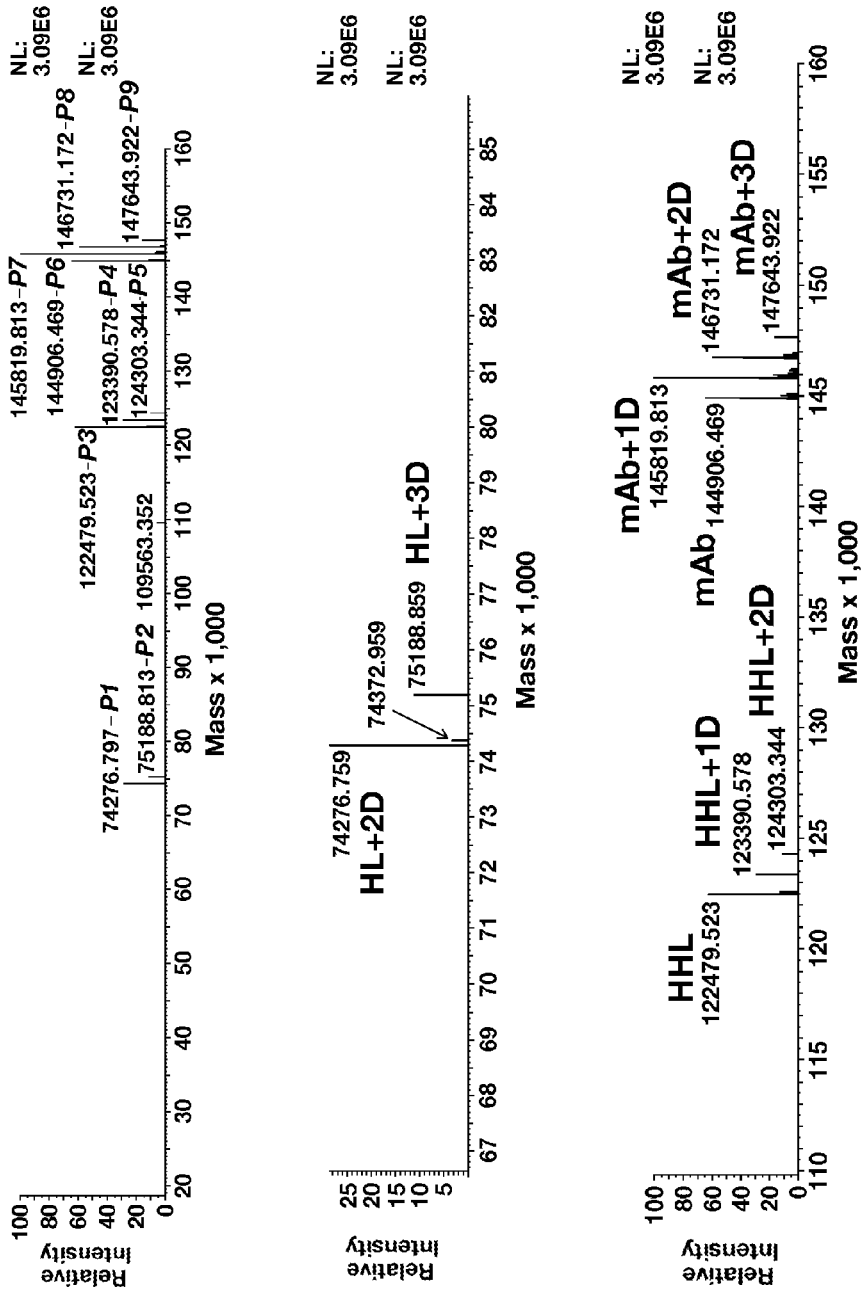
FIG. 5 shows an ESI MS (electro spray ionization mass spectrometry) spectrum of the conjugate H1H6765P-28.

FIG. 5 contains the mass spectrum of the deglycosylated conjugate of H1H6765-28. The mass peaks are consistent with either an intact, heavy-heavy-light, or "half-antibody" by disulfide reunion provided by linker payload 28 or oxidation. The degree in which 28 has made covalent bonds between the sulfhydryls manifests as discreet mass increases corresponding to reacted linker-payload (993 Da, −1 Bromine or 913 Da, −2 Bromines). The mass spectrum is summarized in Table 3.

TABLE 3

| Peak (in FIG. 5) | Mass (Da) | Mass Difference from adjacent peak of the same species (Da) | Matched Components* |
|---|---|---|---|
| P1 | 74276.797 |  | HL |
| P2 | 75188.813 | 912.0 | HL + 1 drug |
| P3 | 122479.523 |  | HHL |
| P4 | 123390.578 | 911.1 | HHL + 1 drug |
| P5 | 124303.344 | 912.8 | HHL + 2 drugs |
| P6 | 144906.469 |  | HHLL |
| P7 | 145819.813 | 913.3 | HHLL + 1 drug |
| P8 | 146731.172 | 911.4 | HHLL + 2 drugs |
| P9 | 147643.922 | 912.8 | HHLL + 3 drugs |

*Note: H refers to heavy chain of mAb; L for light chain of mAb; HL for half mAb; HHL refers to two heavy chains with one light chain; HHLL refers to the full mAb. The increase of mass from addition of one drug is 913 Da.

Figure 6:
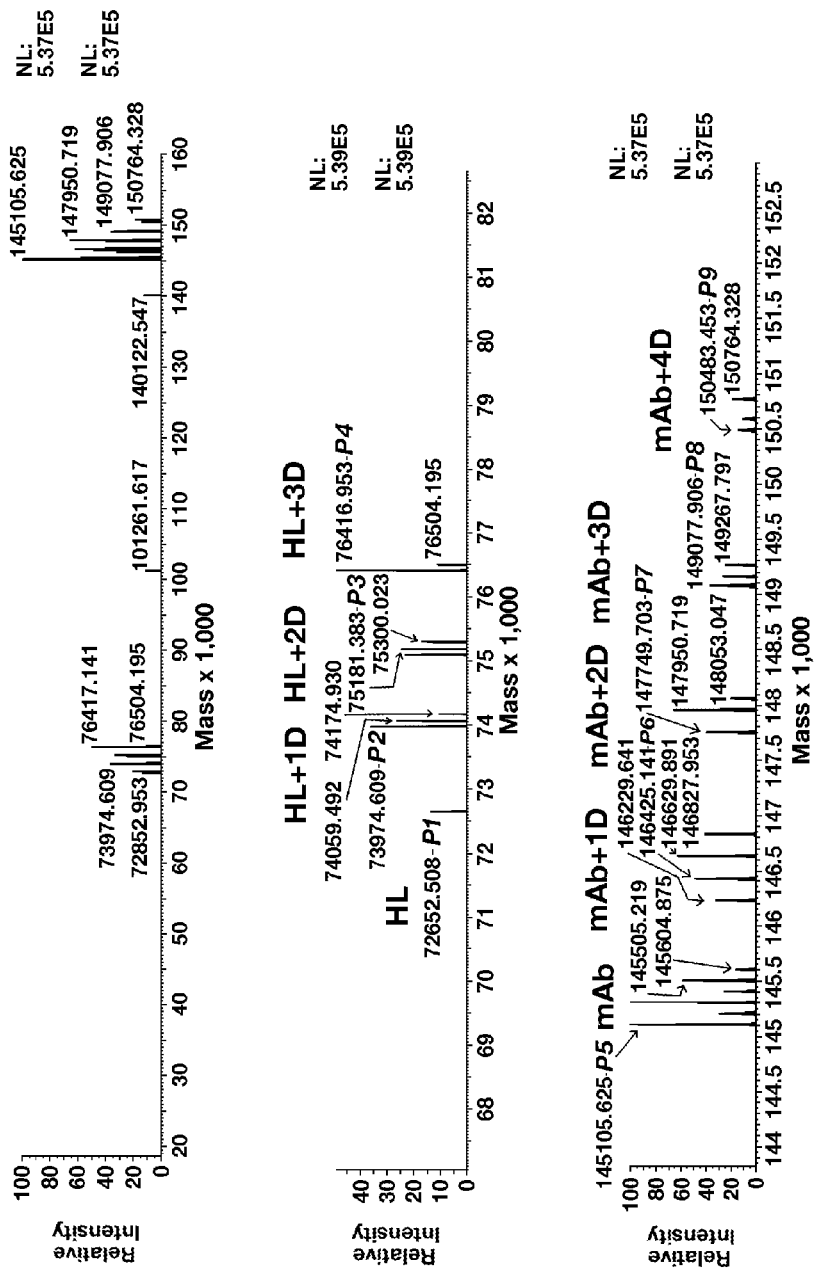
FIG. 6 shows an ESI MS spectrum of the conjugate H1H6765P-26.

FIG. 6 contains the mass spectrum of the deglycosylated conjugate of H1H6765-26. The mass peaks are consistent with either an intact or "half-antibody" by disulfide reunion provided by linker payload 26 or oxidation. The degree in which 26 has made covalent bonds with the sulfhydryls manifests as discreet mass increases corresponding to reacted linker-payload (1323 Da). The mass spectrum is summarized in Table 4.

TABLE 4

| Peak (in FIG. 6) | Mass (Da) | Mass Difference from adjacent peak of the same species (Da) | Matched Components* |
|---|---|---|---|
| P1 | 72652.508 | | HL |
| P2 | 73974.609 | 1122.2 | HL + 1 drug |
| P3 | 75181.383 | 1206.8 | HL + 2 drugs |
| P4 | 76416.953 | 1235.6 | HL + 3 drugs |
| P5 | 145105.625 | | HHLL |
| P6 | 146425.141 | 1319.5 | HHLL + 1 drug |
| P7 | 147749.703 | 1324.6 | HHLL + 2 drug |
| P8 | 149077.906 | 1328.2 | HHLL + 3 drug |
| P9 | 150483.453 | 1405.5 | HHLL + 4 drug |

*Note: H refers to heavy chain of mAb; L for light chain of mAb; HL for half mAb; HHL refers to two heavy chains with one light chain; HHLL refers to the full mAb. Due to the heterogeneity of each species, the increase of mass from addition of one drug may be different from the nominal 1322.9 Da

Example 6

In Vitro Cytotoxicity Assays

In this Example, the ability of various antibody-drug conjugates to kill antigen-expressing tumor cells in vitro was assessed.

Cells were seeded in Nunclon Delta Surface 96 well plates at 1000 (HEK293 and HEK293/PRLR) or 6000 (T47D) cells per well, and cells were grown overnight in complete growth media. For cell viability curves, serially diluted conjugates or free representative payloads were added to the cells at final concentrations ranging from 100 nM to 5 pM and incubated for 3 days. To measure viability, cells were incubated with CCK8 (Dojindo) for the final 1-3 hours and the absorbance at 450 nm (OD450) was determined on a Victor X4 (PerkinElmer). Background OD450 levels (CCK8) from digitonin (40 nM) treated cells were subtracted from all wells and viability is expressed as a percentage of the untreated controls. IC50 values were determined from a four-parameter logistic equation over a 10-point response curve (GraphPad Prism). Maytansinoid conjugate curves and IC50 values are corrected for payload equivalents based on the UV DAR value. For the auristatin (MMAF) conjugate, the IC50 values are assigned a DAR of 1 (i.e., equal to antibody concentration) since a good estimate cannot be obtained by UV or mass spectrometry.

Figure 7:
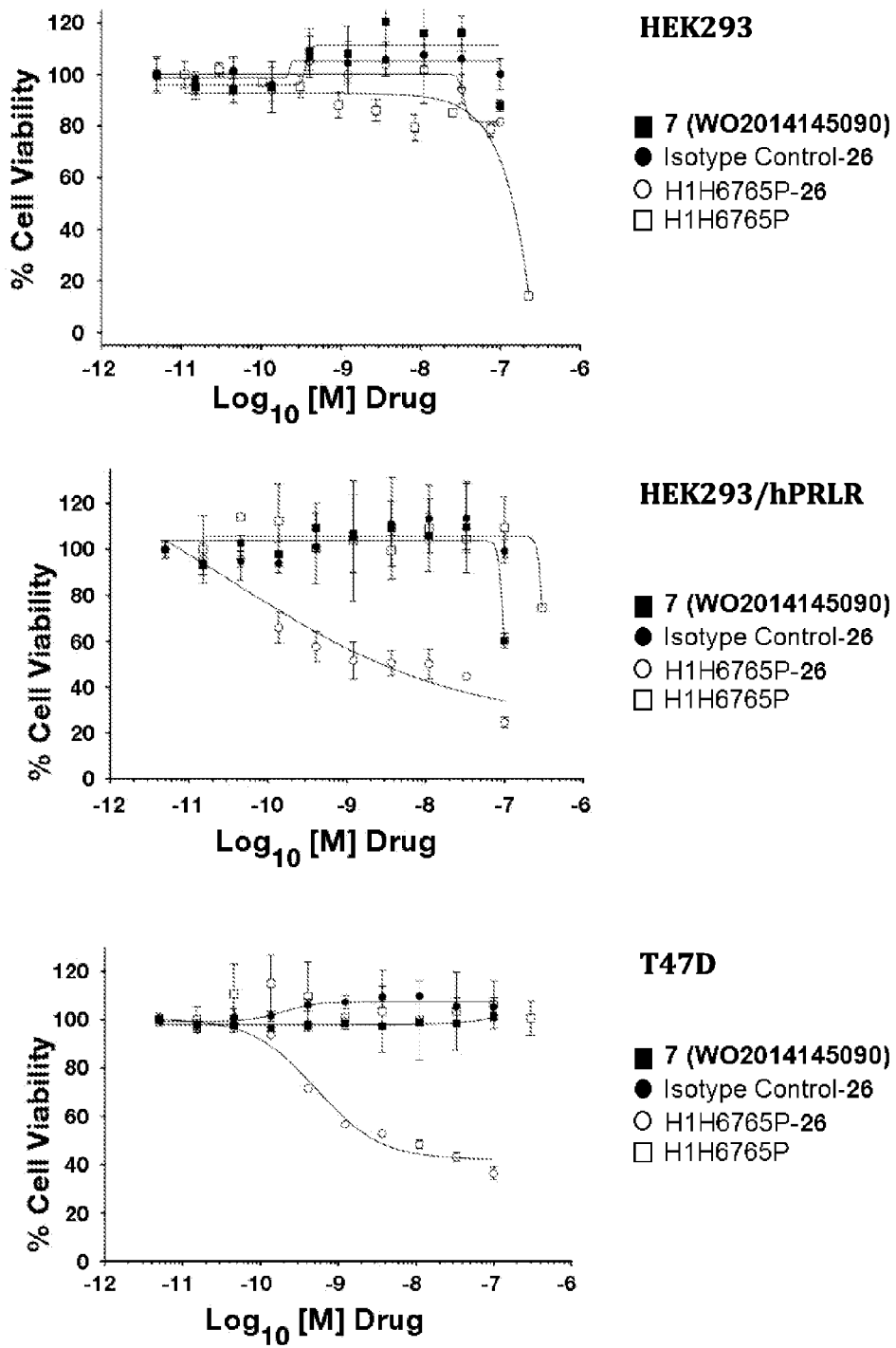
FIG. 7 shows the selective anti-proliferation ability of conjugate H1H6765P-26 in HEK293, HEK293/hPRLR, and T47D.

In FIG. 7, the maytansinoid payload (compound 7 from WO2014145090) was not active up to 100 nM in any of the cell lines assayed as expected. The isotype control cathepsin B cleavable conjugate, Isotype Control-26, was similarly inactive. However, the targeted cathepsin B cleavable H1H6765P-26 conjugate was active with an IC50 of ~4 nM in the engineered cell line HEK293/hPRLR and 0.52 nM in the endogenous cell line T47D. H1H6765P-26 was not active up to 100 nM in the native cell line HEK293 (no target expressed) as expected. The unconjugated H1H6765P was devoid of activity in these assays.

Figure 8:
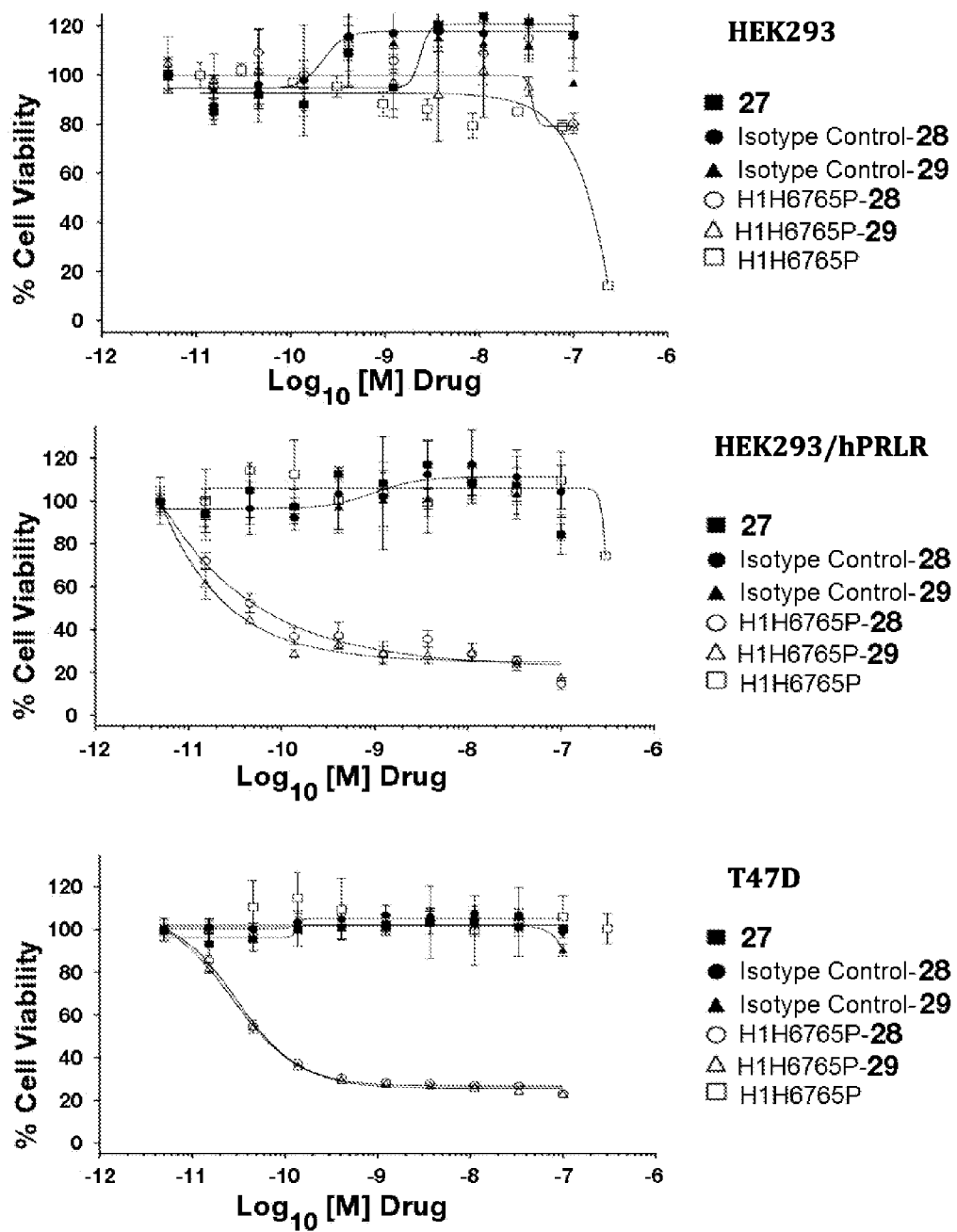
FIG. 8 shows the selective anti-proliferation ability of conjugate H1H6765P-28 and H1H6765P-29 in HEK293, HEK293/hPRLR, and T47D.

In FIG. 8, compound 27 (MMAF) payload was not active up to 100 nM in any of the cell lines assayed as expected. The control non-cleavable conjugates, Isotype Control-28 or Isotype Control-29, were similarly inactive. However, the targeted non-cleavable conjugates, H1H6765P-28 or H1H6765P-29, were active with IC50 values of ~0.04 and ~0.03 nM, respectively, in the engineered cell line HEK293/hPRLR and 0.03 and 0.03 nM, respectively, in the endogenous cell line T47D. Neither H1H6765P-28 or Control-29 were active up to 100 nM in the native cell line HEK293 (no target expressed) as expected. The unconjugated H1H6765P was devoid of activity in these assays.

What is claimed is:

1. An antibody-drug conjugate comprising an antibody, or antigen binding fragment thereof, wherein the antibody or antigen binding fragment thereof is conjugated to at least one moiety of Formula (A):

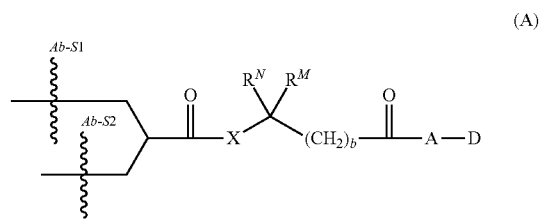

(A)

wherein:
Ab-S1 is a bond to a cysteine residue of the antibody or antigen binding fragment thereof;
Ab-S2 is a bond to a cysteine residue of the antibody or antigen binding fragment thereof;
X is —N($R^A$)— or —O—;
  wherein $R^A$ is a hydrogen atom or alkyl;
$R^N$ and $R^M$ are each, independently, a hydrogen atom or alkyl;
A is absent or a spacer comprising a peptide,
  wherein the peptide comprises 2-20 amino acids;
D is a biologically active molecule; and
b is an integer from 2 to 8.

2. The conjugate of claim 1, wherein the antibody or antigen binding fragment thereof comprises at least one moiety of Formula (A) wherein Ab-S1 is a bond to a cysteine residue of a first heavy chain of the antibody or antigen binding fragment thereof and Ab-S2 is a bond to a cysteine residue of a second heavy chain of the antibody or antigen binding fragment thereof.

3. The conjugate of claim 1, wherein the antibody or antigen binding fragment thereof comprises:
  (i) two moieties of Formula (A) wherein each Ab-S1 is a bond to a cysteine residue of a first heavy chain of the antibody or antigen binding fragment thereof and each Ab-S2 is a bond to a cysteine residue atom of a second heavy chain of the antibody or antigen binding fragment thereof; and
  (ii) two moieties of Formula (A) wherein each Ab-S1 is a bond to a cysteine residue of a light chain of the antibody or antigen binding fragment thereof and each Ab-S2AB is a bond to a cysteine residue of a heavy chain of the antibody of antigen binding fragment thereof.

4. The conjugate of claim 1, wherein the conjugate comprises an anti-PRLR antibody.

5. The conjugate of claim 1, wherein X is —NH—.

6. The conjugate of claim 1, wherein X is —O—.

7. The conjugate of claim 1, wherein X is —NH— or —O— and $R^N$ and $R^M$ are both hydrogen atoms.

8. The conjugate of claim 7, wherein b is 4.

9. The conjugate of claim 1 wherein A is:

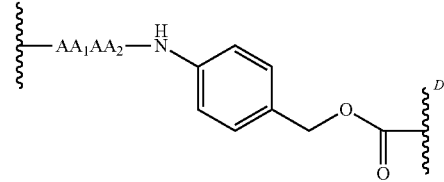

wherein

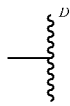

is the bond to D, and AA₁ and AA₂ are each, independently, an amino acid residue.

10. The conjugate of claim 9, wherein A is:

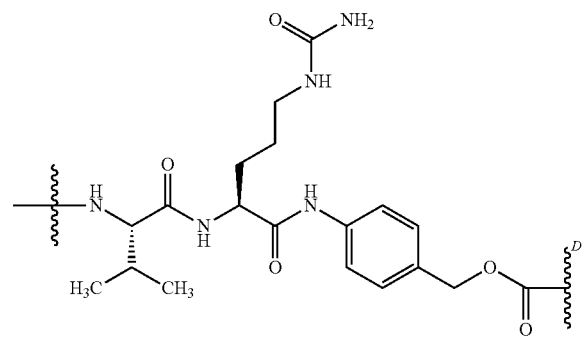

wherein

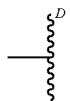

is the bond to D.

11. The conjugate of claim 1, wherein A is absent.

12. The conjugate of claim 1, wherein D is an auristatin or a maytansinoid.

13. The conjugate of claim 1, wherein D is MMAE, MMAD, or MMAF.

14. The conjugate of claim 1, wherein D is a maytansinoid.

15. The conjugate of claim 1, wherein D is DM1, DM4, or a derivative thereof.

16. The conjugate of claim 1, wherein D is:

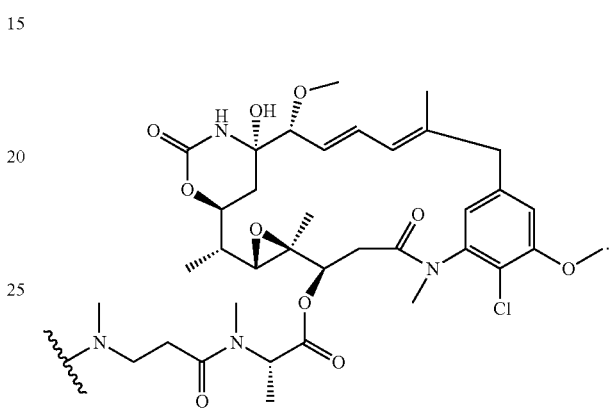

17. The conjugate of claim 1, wherein D is:

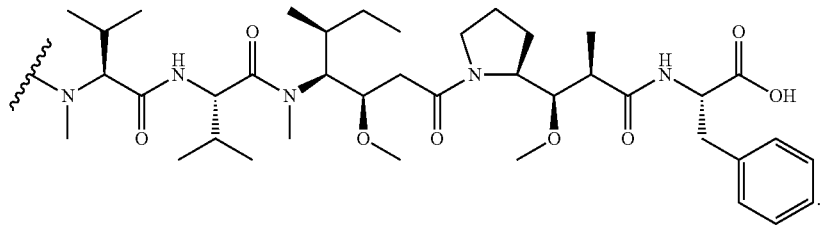 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

18. The conjugate of claim 1, wherein the moiety of Formula (A) is:

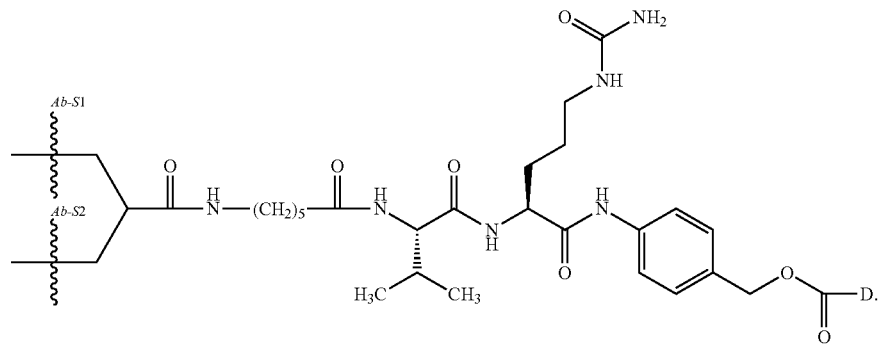

19. The conjugate of claim 1, wherein the moiety of Formula (A) is:

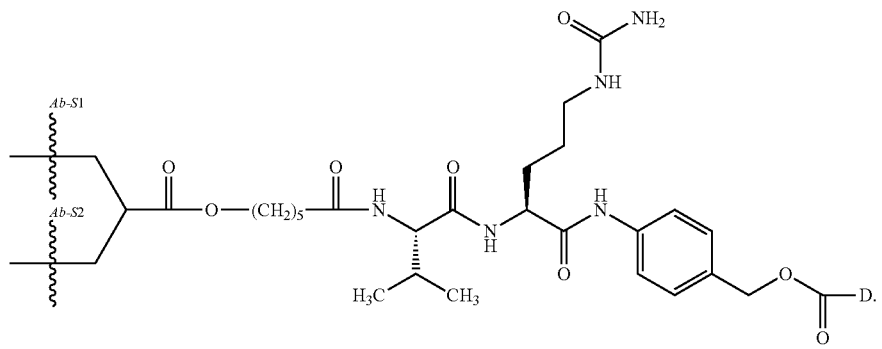

20. The conjugate of claim 1, wherein the moiety of Formula (A) is:

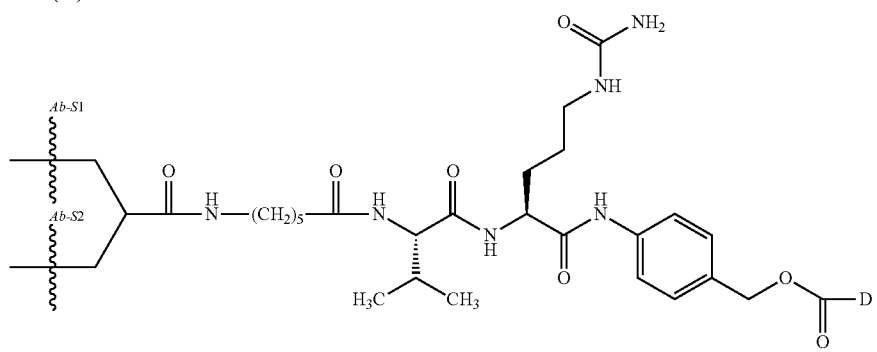

wherein D is a maytansinoid.

21. The conjugate of claim 1, wherein the moiety of Formula (A) is:

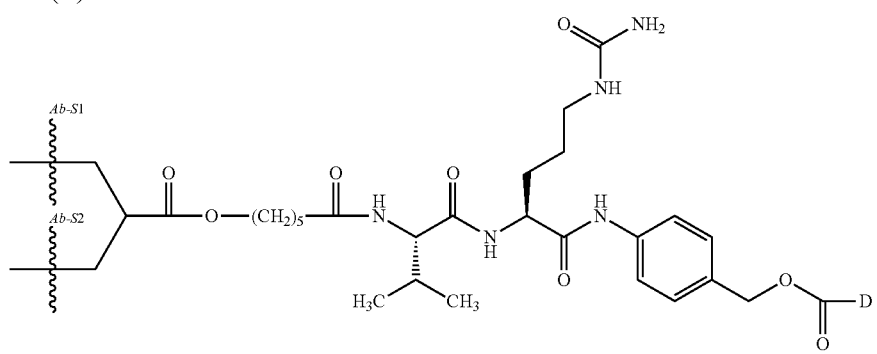

wherein D is a maytansinoid.

22. The conjugate of claim 1, wherein the moiety of Formula (A) is:

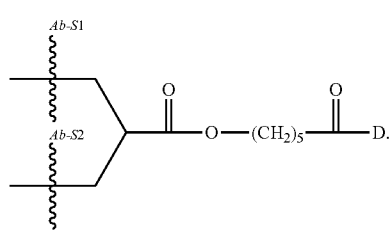

23. The conjugate of claim 1, wherein the moiety of Formula (A) is:

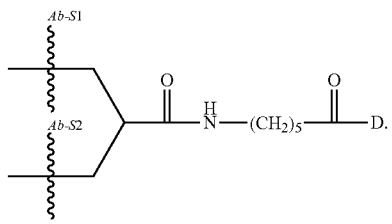

24. The conjugate of claim 1, wherein the moiety of Formula (A) is:

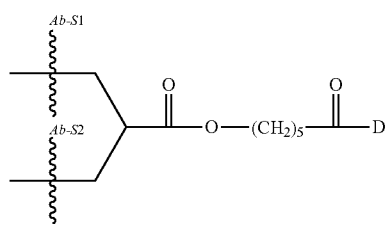

wherein D is an auristatin.

25. The conjugate of claim 1, wherein the moiety of Formula (A) is:

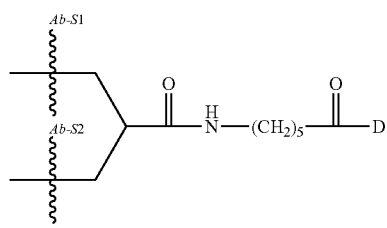

wherein D is an auristatin.

26. The conjugate of claim 1, wherein the moiety of Formula (A) is:

27. A compound of Formula (L1):

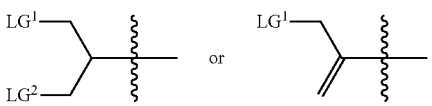

wherein:
$R^U$ is $$\begin{array}{c}LG^1 \\ LG^2\end{array} \quad \text{or} \quad \begin{array}{c}LG^1\end{array}$$

wherein $LG^1$ and $LG^2$, independently at each occurrence, are a leaving group;
X is —N($R^A$)— or —O—;
wherein $R^A$ is a hydrogen atom or alkyl;
$R^N$ and $R^M$ are each, independently, a hydrogen atom or alkyl;
A is absent or a spacer comprising a peptide, wherein the peptide comprises 2-20 amino acids;
D is a biologically active molecule; and
b is an integer from 2 to 8.

28. A pharmaceutical composition comprising a therapeutically effective amount of a conjugate of claim 1 or a

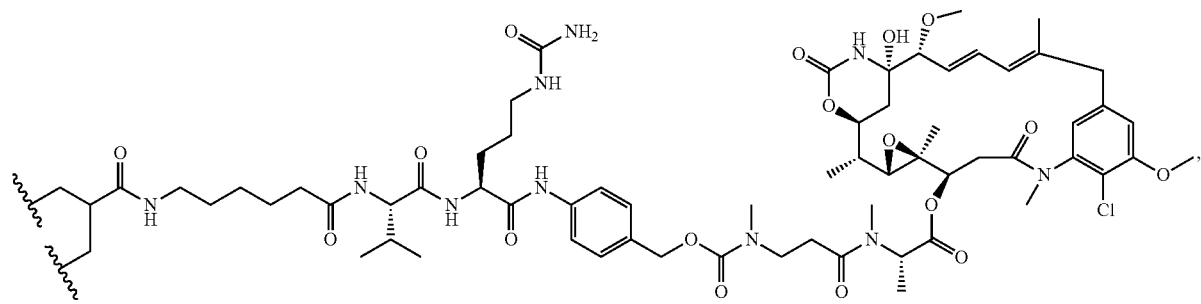

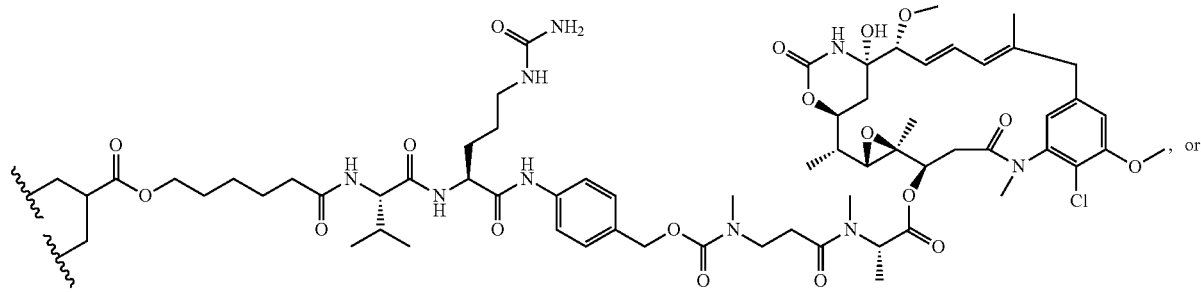

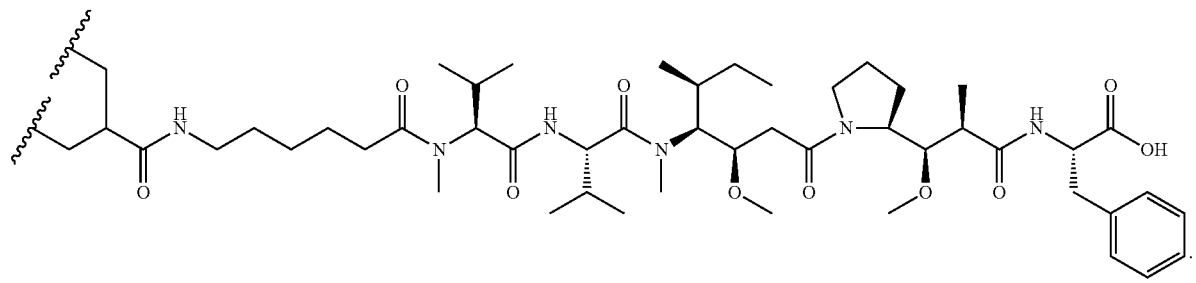

pharmaceutically acceptable salt thereof and one or more pharmaceutically acceptable carriers, diluents, or excipients.

29. A method of reducing, retarding or stopping an abnormal cell growth comprising contacting the abnormal cell with a conjugate of claim 1, in an amount sufficient to retard, reduce or stop the abnormal cell growth, and wherein the abnormal cell growth is retarded, reduced or stopped.

30. A method of killing a cell, comprising contacting the cell with a conjugate of claim 1, in an amount sufficient to kill the cell, and wherein the cell is killed.

31. A method of treating a medical disorder in an individual suffering from the medical disorder, comprising administering to the individual an effective amount of a composition comprising a conjugate of claim 1.

32. The compound of claim 27, wherein the leaving group is a halide.

33. The compound of claim 27, wherein X is —NH—.

34. The compound of claim 27, wherein X is —O—.

35. The compound of claim 27, wherein $R^N$ and $R^M$ are both hydrogen atoms.

36. The compound of claim 27, wherein b is an integer from 3-6.

37. The compound of claim 27, wherein $R^N$ and $R^M$ are both hydrogen atoms and b is 4.

38. The compound of claim 27, wherein A is:

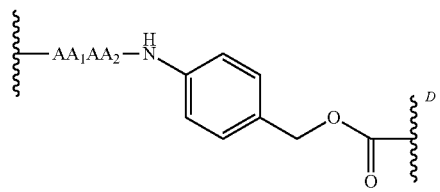

wherein

is the bond to D and AA1 and AA1 are each, independently, an amino acid residue.

39. The compound of claim 27, wherein A is:

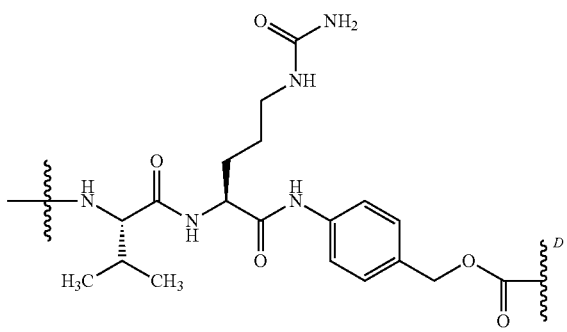

wherein

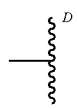

is the bond to D.

40. The compound of claim 27, wherein A is absent.

41. The compound of claim 27, wherein D is an auristatin or a maytansinoid.

42. The compound of claim 27, wherein D is MMAE, MMAD, or MMAF.

43. The compound of claim 27, wherein D is a maytansinoid.

44. The compound of claim 27, wherein D is:

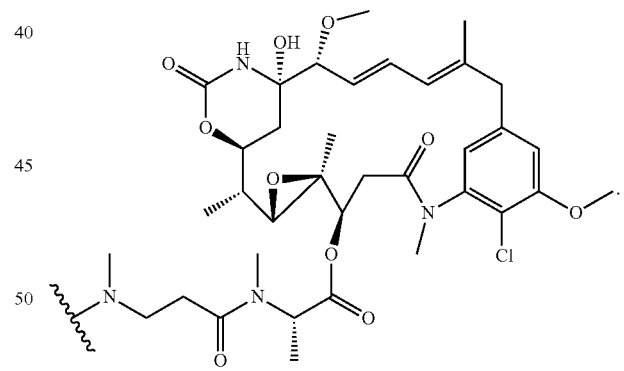

45. The compound of claim 27, wherein D is:

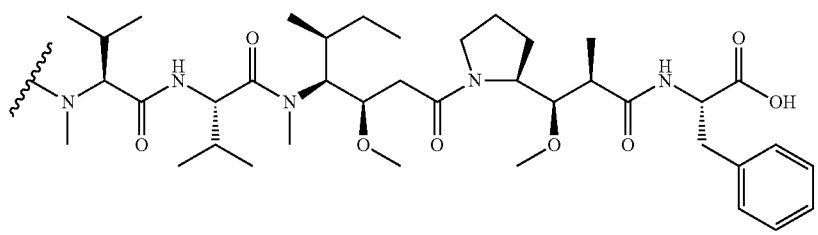

46. The compound of claim 27, wherein the compound is:
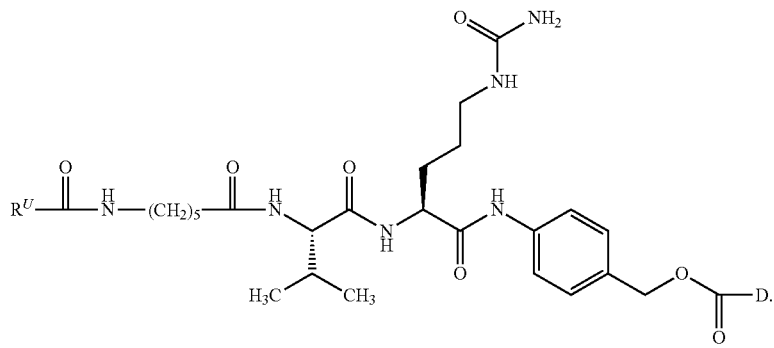
47. The compound of claim 27, wherein the compound is:
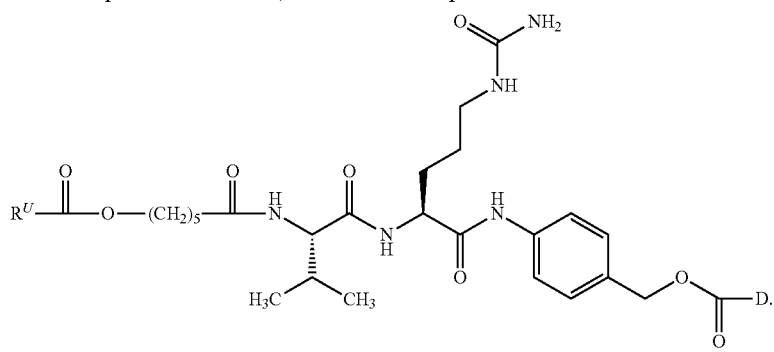
48. The compound of claim 27, wherein the compound is:
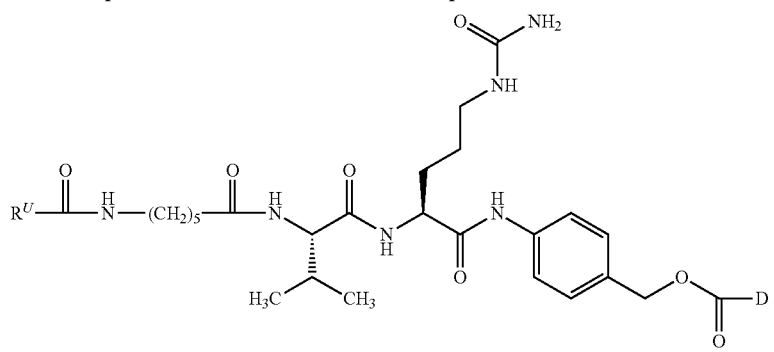
wherein D is a maytansinoid.
49. The compound of claim 27, wherein the compound is:
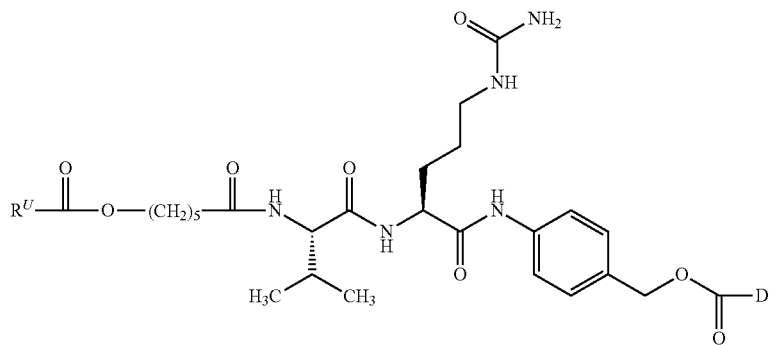
wherein D is a maytansinoid.

50. The compound of claim 27, wherein the compound is:
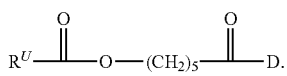
51. The compound of claim 27, wherein the compound is:
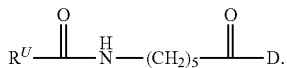
52. The compound of claim 27, wherein the compound is:
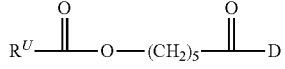
wherein D is an auristatin.
53. The compound of claim 27, wherein the compound is:
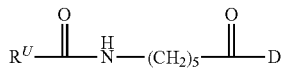
wherein D is an auristatin.
54. The compound of claim 27, wherein the compound is:
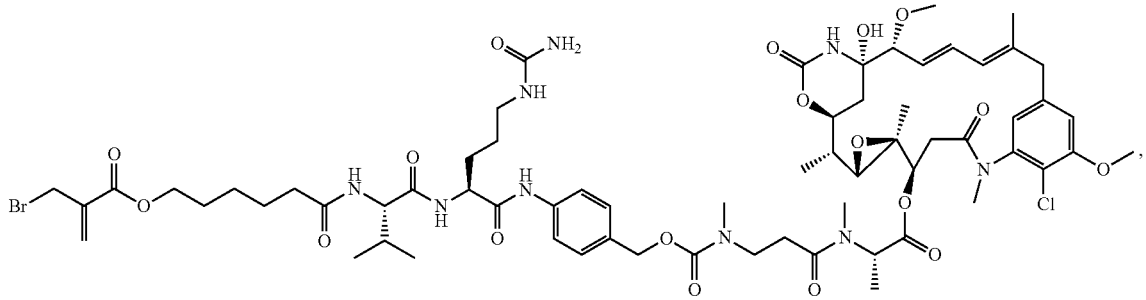
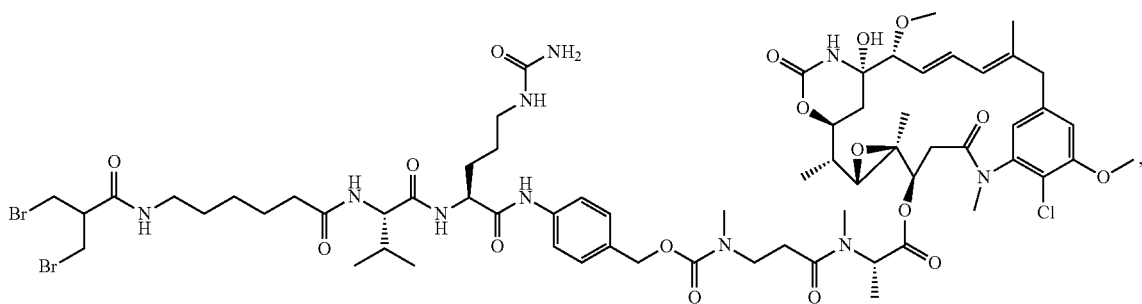
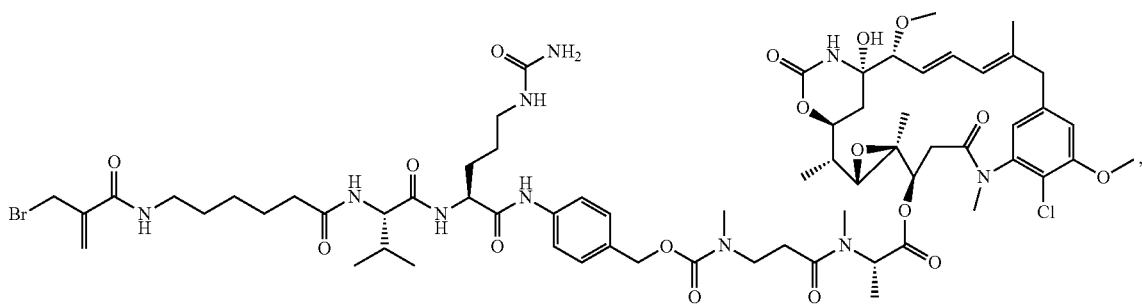

91
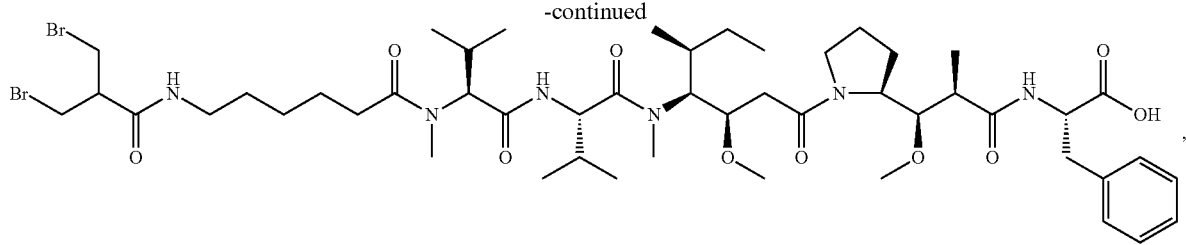
-continued
92
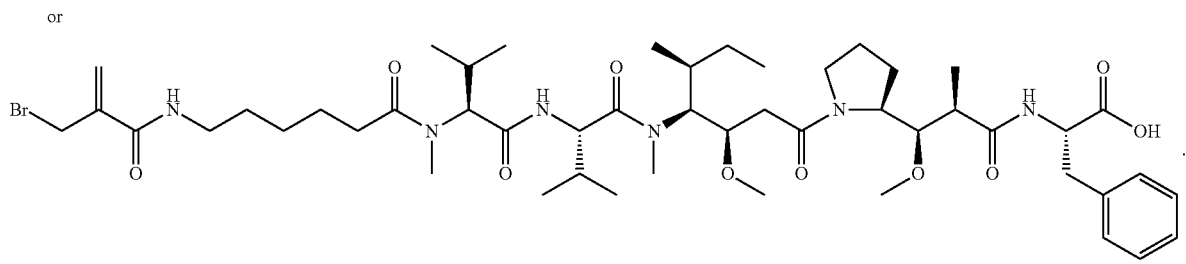
or
* * * * *